US008067456B2

(12) United States Patent
Paulini et al.

(10) Patent No.: US 8,067,456 B2
(45) Date of Patent: *Nov. 29, 2011

(54) TETRAHYDROCARBAZOLE DERIVATIVES HAVING IMPROVED BIOLOGICAL ACTION AND IMPROVED SOLUBILITY AS LIGANDS OF G-PROTEIN COUPLED RECEPTORS (GPCPS)

(75) Inventors: Klaus Paulini, Maintal (DE); Matthias Gerlach, Brachttal (DE); Eckhard Gunther, Maintal (DE); Emmanuel Polymeropoulos, Frankfurt am Main (DE); Silke Baasner, Schöneck (DE); Peter Schmidt, Schöneck (DE); Ronald Kühne, Berlin (DE); Arvid Söderhäll, Spanga (SE)

(73) Assignee: AEterna Zentaris GmbH, Frankfurt am Main (DE)

( * ) Notice: Subject to any disclaimer, the term of this patent is extended or adjusted under 35 U.S.C. 154(b) by 505 days.

This patent is subject to a terminal disclaimer.

(21) Appl. No.: 12/070,214

(22) Filed: Feb. 14, 2008

(65) Prior Publication Data

US 2008/0280965 A1  Nov. 13, 2008

Related U.S. Application Data

(62) Division of application No. 11/172,142, filed on Jun. 30, 2005, now Pat. No. 7,375,127.

(60) Provisional application No. 60/587,969, filed on Jul. 14, 2004, provisional application No. 60/683,178, filed on May 20, 2005.

(30) Foreign Application Priority Data

Jul. 14, 2004 (DE) .......................... 10 2004 033 902

(51) Int. Cl.
*A61K 31/403* (2006.01)
*C07D 209/82* (2006.01)
(52) U.S. Cl. ....................... 514/411; 548/448
(58) Field of Classification Search .................. 514/411; 548/448
See application file for complete search history.

(56) References Cited

U.S. PATENT DOCUMENTS

| 3,970,757 | A | 7/1976 | Cross |
| 5,708,187 | A | 1/1998 | Flaugh |

FOREIGN PATENT DOCUMENTS

| DE | 101 64 564 A1 | 6/2003 |
| EP | 0 239 306 B1 | 9/1987 |
| EP | 0 679 642 B1 | 11/1995 |
| EP | 0 603 432 B1 | 10/1998 |
| WO | WO 95/28405 | 10/1995 |
| WO | WO 96/24597 | 8/1996 |
| WO | WO 97/14682 | 4/1997 |
| WO | WO 97/14697 | 4/1997 |
| WO | WO 97/21435 | 6/1997 |
| WO | WO 97/21703 | 6/1997 |
| WO | WO 97/41126 | 11/1997 |
| WO | WO 98/55116 | 12/1998 |
| WO | WO 98/55470 | 12/1998 |
| WO | WO 98/55479 | 12/1998 |
| WO | WO 99/01764 | 1/1999 |
| WO | WO 99/21553 | 5/1999 |
| WO | WO 99/51231 | 10/1999 |
| WO | WO 99/51596 | 10/1999 |
| WO | WO 00/04013 | 1/2000 |
| WO | WO 00/53178 | 9/2000 |
| WO | WO 00/53602 | 9/2000 |
| WO | WO 02/11732 | 2/2002 |
| WO | WO 03/011839 | 2/2003 |
| WO | WO 03/013528 | 2/2003 |
| WO | WO 03/051837 | 6/2003 |
| WO | WO 03/078398 | 9/2003 |
| WO | WO 2005/033099 | 4/2005 |

OTHER PUBLICATIONS

Giron, D. J. Therm. Anal. Cal. 2001, 64, pp. 37-60.*
Giron, D. J. Therm. Anal. Cal. 2002, 68, pp. 335-357.*
B. Rodriquez-Spong et al. Advanced Drug Delivery Reviews, 2004, 56, pp. 241-274.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Discovery Heatlh (http://health.discovery.com/centers/womens/endometriosis/prevention.html), accessed Mar. 18, 2010.*
WebMD (http://women.webmd.com/endometriosis/endometriosis-prevention), Aug. 1, 2007.*
MayoClinic.com (http://www.mayoclinic.com/health/endometriosis/DS00289/DSECTION=prevention), Sep. 11, 2008.*
Merriam-Webster Online Dictionary entry for "derivative", (http://www.merriam-webster.com/dictionary/derivative), last accessed May 12, 2010.*
Merriam-Webster Online Dictionary entry for "analogue", (http://www.merriam-webster.com/dictionary/analogue), last accessed May 12, 2010.*
Schoneberg et al. Pharmacology & Therapeutics, 2004, 104, 173-206.*

(Continued)

*Primary Examiner* — Joseph Kosack
*Assistant Examiner* — Matthew Coughlin
(74) *Attorney, Agent, or Firm* — Goodwin Procter LLP

(57) ABSTRACT

The present invention provides novel tetrahydrocarbazole derivatives which have improved properties and which can be employed as inhibitors of GPCRs. This results in the possibility of using the novel compounds to treat pathological conditions whose severity depends on the pathobiochemical effect of GPCRs. The compounds of the invention act in particular via an antagonistic inhibition of the LHRH receptor. The invention further provides medicaments which comprise one or more of the novel compounds as active ingredient. The medicaments are suitable in particular to be employed in an oral dosage form for a mammal, in particular a human.

9 Claims, 5 Drawing Sheets

OTHER PUBLICATIONS

Luo et al. Cell, 2009, 136, pp. 823-837.*
Herbst, K. Current Opinion in Pharmacology, 2003, 3, 660-666.*
Quartara et al. Neuropeptides 1998, 32, 1-49.*
Ahlstedt et al. Biochemical Pharmacology 2008, 76, 576-471.*
Y.-F. Zhu et al., Expert Opin. Therap. Patents 14(2),187-199 (2004).
Y.-F. Zhu et al., Ann. Rep. Med. Chem. (39), 99-110 (2004).
F.C. Tucci et al., Curro Opin. Drug Discovery & Development 7(6),832-847 (2004).
R.E. Armer, Curr. Med. Chem. 11, 3017-3028 (2004).
M.V. Chengalvala et al., Curro Med. Chem.—Anti-Cancer Agents, 3, 399-410(2003).
N. Cho etal., in J. Med. Chem. 41, 4190-4195 (1998).
S. Sasaki et al., in J. Med. Chem 46, 113-124 (2003).
Z. Guo et al., in J. Med. Chem. 47,1259-1271 (2004).
J. T. Randolph et al., in J. Med. Chem. 47(5), 1085-1097 (2004).
D. J. Davies et al. describe in J. Med Chem. 41, 451-467 (1998).
S. J. Shuttleworth et al., in Bioorg. Med. Chem Lett. 14,3037-3042 (2004).
R Millet et al., describe in Letters in Peptide Science 6,221-223 (1999).
Koppitz et al., THL 46(6),911-914 (2005).
G. Giardina et al., IDrugs 6(8), 758-772 (2003).
V. Leroy et al., Expert Opinion on Investigational Drugs 9(4), 735-746 (2000).
C. Swain et al., Annual Reports in Medicinal Chemistry 34,51-60 (1999).
RM. Navari et al., Cancer Investigation 22(4) 569-576 (2004).
RG. Hill et al., describe in Pain, 523-530 (2003).
A. von Sprecher et al. in IDrugs 1(1), 73-91 (1998).
Y. Fang et al., DDT 8(16), 755-761 (2003).
Y.-F. Zhu et al., Expert Opin. Therap. Patents 14(2), 187-199 (2004).
Y.•F. Zhu et al., Ann. Rep. Med. Chem. (39), 99-110 (2004).
Z. Guo et al., J. Med. Chem. 47, 1259-1271 (2004).
V. Leroy et al., Expert Opinion on Investigational Drugs 9(4), 735-746 (2000).
Ullman's Encyclopedia of Technical Chemistry, vol. 4, (1953)1 39.
Schally et al. Science 173, 1036-1038 (1971).
S.J. Shuttleworth et al., Bioorg. Med. Chem. Lett. 14, 3037-3042 (2004).
S. Sasaki et al., J. Med. Chem. 46, 113-124 (2003).
R.M. Navari et al., Cancer Investigation 22(4) 569-576 (2004).
R.G. Hill et al., Pain, 523-530 (2003).
M.V. Chengalvala et al., Curr. Med. Chem.—Anti-Cancer Agents, 3, 399-410 (2003).
R.E. Armer, Curr. Med. Chem. 11, 3017-3028 (2004).
R. Millet et al., Letters in Peptide Science 6, 221-233 (1999).
R. P. Millar et al., British Med. Bull. 56, 761-772 (2000).
R. E. Felberbaum et al., Mol. Cell. Endocrinology 166, 9-14 (2000).
N. Cho et al. in J. Med. Chem. 41, 4190-4195 (1998).
Mitsunobu et al., J. Am. Chem. Soc. 1972, 94, 679.
Majer et al. Biochem & Biophys. Res. Commun. 1988, 150, 1017.
Koppitz et al.,Tetrahedron Letters 46(6), 911-914 (2005).
K. L. Pierce et al., Nat. Rev. Mol. Cell Biol. 3, 639-650 (2002).
Spiegel AJ et al., Journal of Pharmaceutical Sciences, vol. 52 (1963), 917-927.
J.R. Cashman et al., J. Org. Chem., 1982, 47 (24), 4645-4650.
J. T. Randolph et al., in J. Med. Chem. 47(5), 1085.1097 (2004).
Halmos et al., Proc. Natl. Acad. Sci. USA, 1996, 93, 2398.
H. V. Czetsch-Lindenwald, "Hilfsstoffe für Pharmazie and angrenzende Gebiete"; Pharm. Ind. 2, 1961, 72 et seq.
H. Takahata (J. Org. Chem. 1989, 54, 4812).
F.C. Tucci et al., Curr. Opin. Drug Discovery & Development 7(6), 832-847 (2004).
F. Haviv et al. (Integration of Pharmaceutical Discovery and Development: Case Studies, Chapter 7, ed. Borchardt et al., Plenum Press, New York (1998)).
E. Heuillet et al., J. Neurochem., 60: 868-876 (1993).
Dr. H.P. Fiedler, „Lexikon der Hilfsstoffe für Pharmazie, Kosmetik and angrenzende Gebiete, Cantor KG, Aulendorf in Württemberg, 1971.
D. K. Vassilatis et al., PNAS 100(8), 4903-4908 (2003).
D. J. Davies et al. (J. Med. Chem. 41, 451-467 (1998)).
D.M. Ziegler, Biochem. Soc. Trans., 1978, 6(1), 94-96.
D. Aharony et al. Mol. Pharmacol, 44: 356-363 (1993).
Casarett & Doull's "Toxicology, the Basic Science of Poisons", Chapter 6: Biotransformation of Xenobiotics, C. D. Klaassen Ed., McGraw-Hill 2001.
C. Swain et al., Annual Reports in Medicinal Chemistry 34, 51-60 (1999).
Maki et al., Chem. Pharm. Bull. 1973, 21, 240.
Britten & Lockwood , J. Chem. Soc. Perkin Trans. I 1974, 1824.
A. von Sprecher et al. (IDrugs 1(1), 73-91 (1998)).

* cited by examiner

FIGURE 1 (COMPOUND 7)
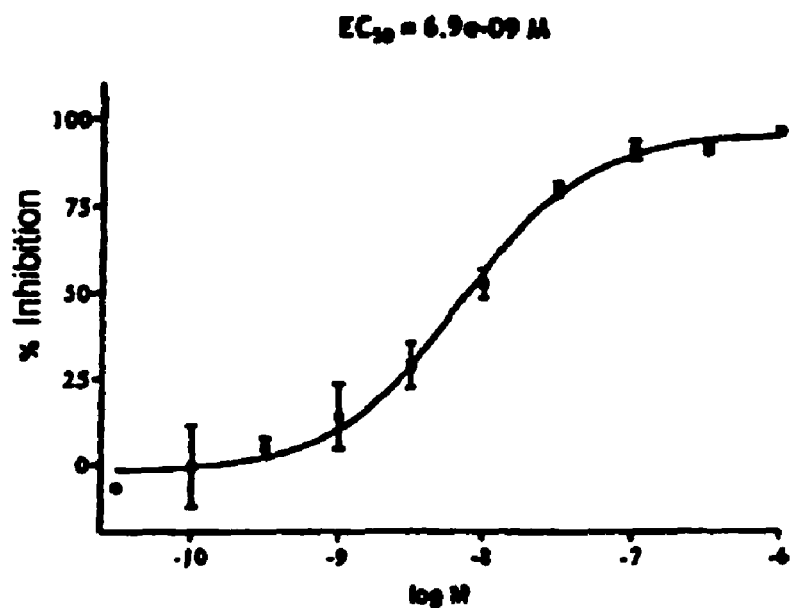
FIGURE 2 (COMPOUND 48)
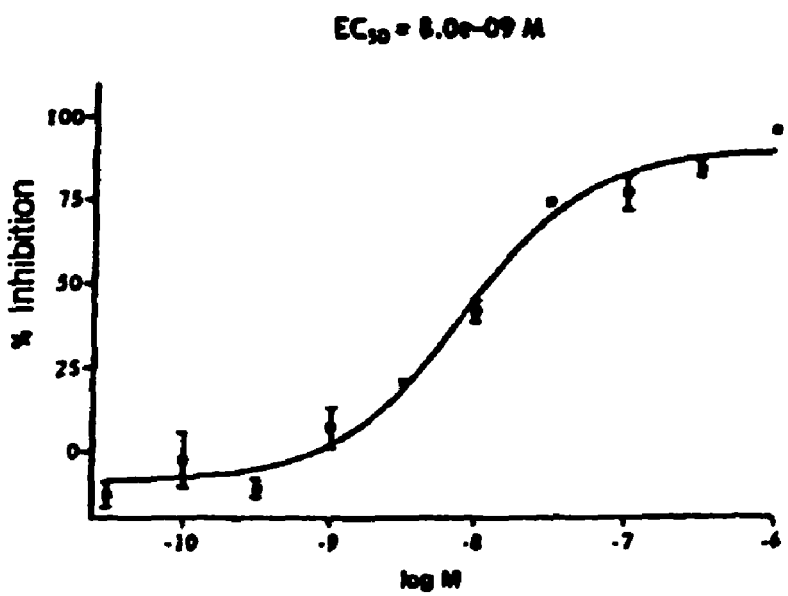

FIGURE 3 (COMPOUND 66)
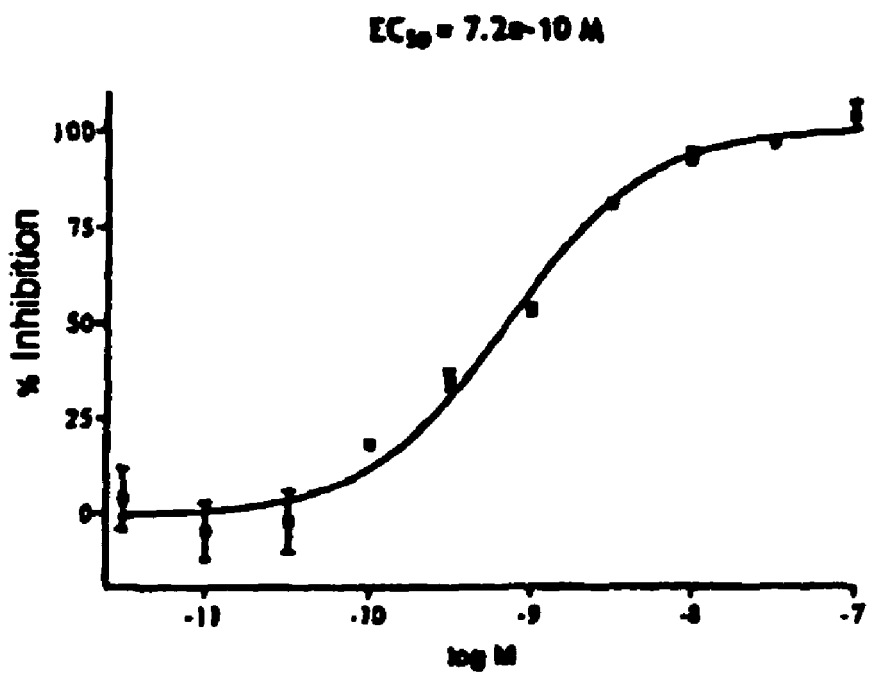
FIGURE 4 (COMPOUND 67)
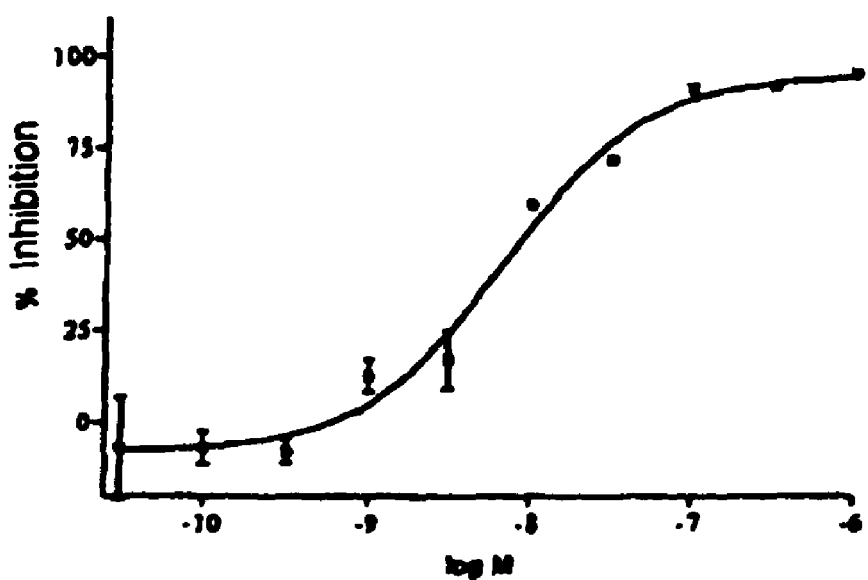

FIGURE 5 (COMPOUND 65)
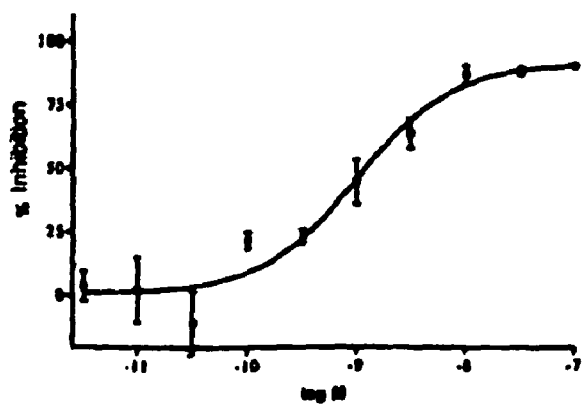
FIGURE 6 (COMPOUND 75)
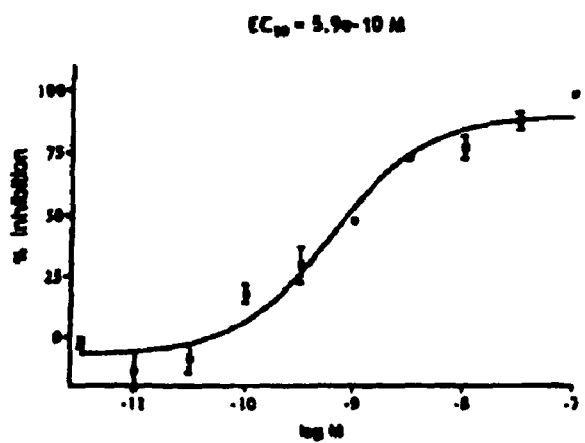
FIGURE 7 (COMPOUND 76)
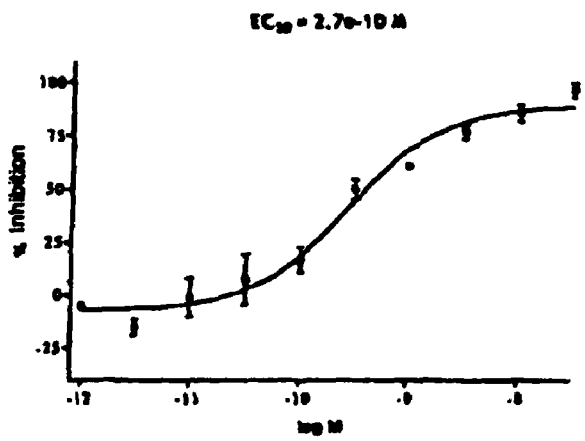

FIGURE 8: Competition plot for compound 68 on the human NK1 receptor
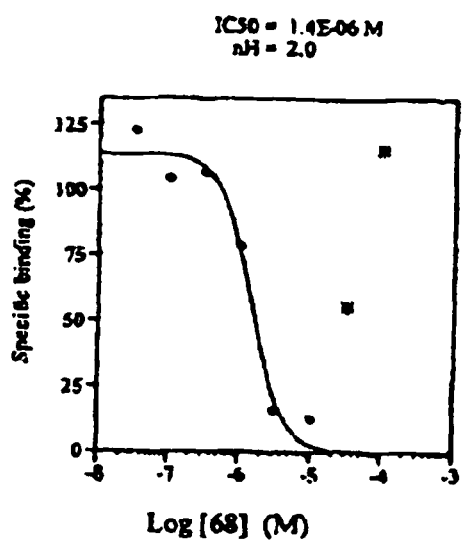
FIGURE 9: Competition plot for compound 68 on the human NK2 receptor
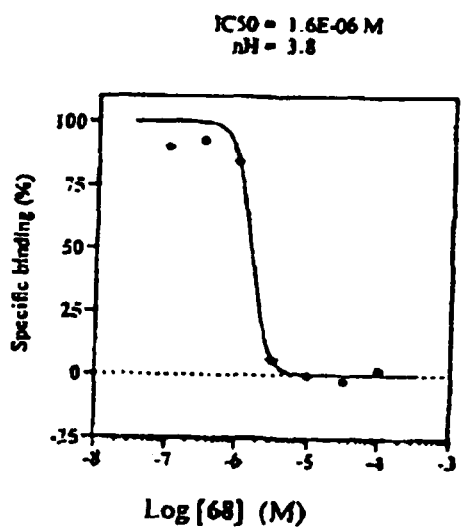

FIGURE 10: Competition plot for compound 76 on the human NK1 receptor
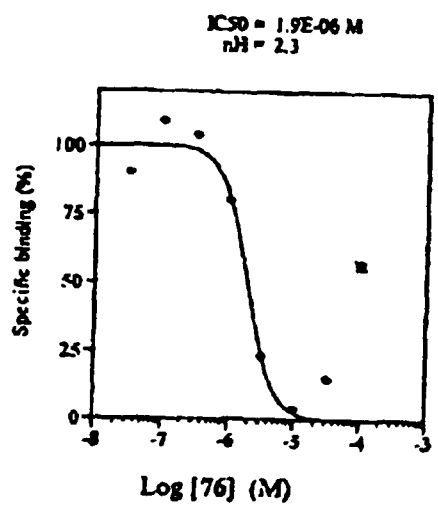
FIGURE 11: Competition plot for compound 76 on the human NK2 receptor
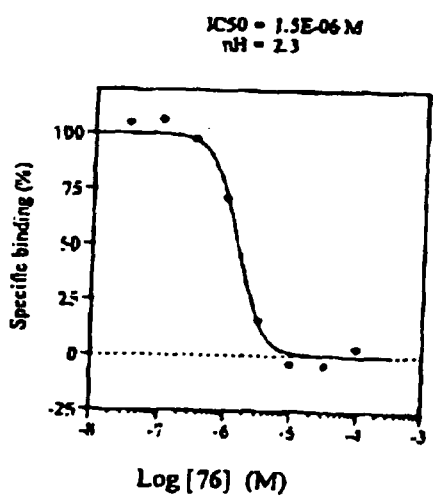

TETRAHYDROCARBAZOLE DERIVATIVES HAVING IMPROVED BIOLOGICAL ACTION AND IMPROVED SOLUBILITY AS LIGANDS OF G-PROTEIN COUPLED RECEPTORS (GPCPS)

CROSS REFERENCE TO RELATED APPLICATIONS

This application is a divisional of application Ser. No. 11/172,142 filed on Jun. 30, 2005, which has now issued as U.S. Pat. No. 7,375,127 on May 20, 2008, and which claims the benefit of priority of Provisional Application No. 60/587,969, filed on Jul. 14, 2004, Provisional Application No. 60/683,178, filed on May 20, 2005, and German Application No. 10 2004 033 902.3, filed on Jul. 14, 2004, each of which is incorporated in its entirety herein by reference thereto.

FIELD OF THE INVENTION

The present invention relates to novel tetrahydrocarbazole derivatives having improved biological action, improved oral bioavailability and improved metabolic stability as ligands of G-protein coupled receptors (GPCRs), in particular as ligands of the receptor for luteinizing hormone releasing hormone (LHRH receptor), to the preparation thereof, and to the use thereof in pharmaceutical compositions for the treatment of pathological conditions mediated by G-protein coupled receptors in a mammal and in particular in a human.

BACKGROUND OF THE INVENTION

The contents of all the publications cited in this application, or comparable sources which are quoted, in order to explain the background of the invention are incorporated in the present application for the purpose of the disclosure.

G-protein coupled receptors represent a superfamily of cell membrane-associated receptors which play an important part in numerous biochemical and pathobiochemical processes in mammals and especially in humans. AU GPCRs consist of seven hydrophobic, transmembrane alpha-helical domains which are connected together by three intracellular and three extracellular loops and have an extracellular amino terminus and an intracellular carboxy terminus. One or more heterotrimeric G proteins are involved in their cellular signal transduction. Diverse physiological stimuli such as photosensitivity, taste and odor, but also fundamental processes such as metabolism, reproduction and development are mediated and controlled by them. GPCRs exist for erogenous and endogenous ligands. Peptide hormones, biogenic amines, amino acids, nucleotides, lipids, $Ca^{2+}$, but also photons, have inter alia been identified as ligands; moreover one ligand may activate different receptors.

According to a recent investigation, 367 sequences have been identified in the human genome for G-protein coupled receptors (GPCRs) with endogenous ligands, D. K. Vassilatis et al., *PNAS* 100(8), 4903-4908 (2003). Of these, 284 belong to class A, 50 to class B, 17 to class C and 11 to class F/S. Examples belonging to class A are the bombesin, the dopamine and the LHRH receptors, and to class B are the VIP and the calcitonin receptors. The natural ligands for numerous GPCRs are as yet unknown.

Owing to their function, GPCRs are suitable as targets for medicaments for the therapy and prevention of a large number of pathological conditions. It is speculated that about 50% of currently known targets for active ingredients are GPCRs [Y. Fang et al., *DDT* 8(16), 755-761 (2003)]. Thus, GPCRs play an important part in pathological processes such as, for example, pain (opioid receptor), asthma ($\beta_2$-adrenoceptor), migraine (serotonin 5HT1B/1D receptor), cancer (LHRH receptor), cardiovascular disorders (angiotensin receptor), metabolic disorders (GHS receptor) or depression (serotonin 5-$HT_{1a}$ receptor), K. L. Pierce et al., *Nat. Rev. Mol. Cell Biol.* 3, 639650 (2002).

General information about GPCRs is to be found under http://www.gpcr.org.

The present invention describes novel ligands with improved properties for GPCRs in general, the compounds provided by the invention acting in particular as antagonists of the LHRH receptor.

The natural ligand of this receptor, the peptide hormone LHRH, is synthesized in cells of the hypothalamus and released in pulsatile fashion from the hypothalamic neurons into the capillary plexus of the ementia mediana. In the anterior lobe of the pituitary, LHRH binds to the LHRH receptors of the gonadotropic cells and stimulates certain trimeric G-proteins, which initiate a branched signal transduction cascade. The initial event is activation of phospholipase C, $A_2$ and/or D. This leads to an increased provision of the second messengers diacylglycerol and $IP_3$, followed by $Ca^{2+}$ mobilization from intracellular pools, and activation of various subordinate protein kinases. Finally, there is stimulation of the production and temporally defined pulsatile release of the gonadotropins FSH and LH. The two hormones are transported via the circulation to the target organs the testes and ovaries respectively. There they stimulate the production and release of the appropriate sex hormones. In the opposite direction there is a complex feedback mechanism by which the concentration of the sex hormones formed in turn regulates the release of LH and FSH.

In the male organism, LH binds to membrane receptors of the Leydig cells and stimulates testosterone biosynthesis. FSH acts via specific receptors on the Sertoli cells and assists the production of spermatozoa. In the female organism, LH binds to the LH receptors of the theca cells and activates the formation of androgen-synthesizing enzymes. FSH stimulates proliferation of granulosa cells of certain follicle stages via the FSH receptors thereof. The androgens which are formed are converted in the adjacent granulosa cells to the estrogens estrone and estradiol.

A number of disorders distinguished by benign or malignant tissue proliferations depend on stimulation by sex hormones such as testosterone or estradiol. Typical disorders of this type are prostate cancer and benign prostate hyperplasia (BPH) in men, and endometriosis, uterine fibroids or uterine myomas, pubertas praecox, hirsutism and polycystic ovary syndrome, and breast cancer, uterine cancer, endometrial cancer, cervical cancer and ovarian cancer in women.

Since its discovery in 1971 by Schally et al. *Science* 173, 1036-1038 (1971), more than 3000 synthetic analogues of natural LHRH have been synthesized and tested. Peptide agonists such as triptorelin and leuprolide have been established for many years successfully in the therapy of gynecological disorders and cancers. However, the disadvantage of agonists is generally that they stimulate LHRH receptors in the initial phase of use and thus lead to side effects via an initial increase in the sex hormone levels. Only after downregulation of the LHRH receptor as a result of this overstimulation can the superagonists display their effect. This leads to a complete reduction in the sex hormone levels and thus to pharmacological castration with all the signs and symptoms. This disadvantage is associated with the impossibility of targeted adjustment of the level of sex hormones via the dosage. Thus, therapy of diseases which do not require a total reduction of the sex hormone levels to the castration level, such as, for example, benign tissue proliferations, with an agonist is not optimal for the patient.

This has led to the development of peptide LHRH receptor antagonists, of which, for example, cetrorelix (Cetrotide®) has been successfully introduced for controlled ovarian stimulation in the context of the treatment of female infertility. The antagonists inhibit the LHRH receptor immediately and dose-dependently, and thus lead to an immediate reduction in the plasma levels of testosterone or estradiol and progesterone. The peptide antagonists are, however, somewhat less potent than the agonists, and thus higher doses must be given.

A review of the clinical applications and the potential of LHRH agonists and antagonists is given by R. P. Millar et al. in *British Med. Bull.* 56, 761-772 (2000) and R. E. Felberbaum et al., Mol. Cell *Endocrinology* 166, 9-14 (2000) and F. Haviv et al. in *Integration of Pharmaceutical Discovery and Development Case Studies*, Chapter 7, ed. Borchardt et al., Plenum Press, New York (1998). Besides the treatment of malignant and benign neoplastic diseases, further possible applications are controlled ovarian stimulation in the context of in vitro fertilization, fertility control (contraception), and protection from unwanted side effects of radio- or chemotherapy, the treatment of HIV infections (AIDS) and of neurological or neurodegenerative disorders such as Alzheimer's disease. Specific LHRH receptors have not only been found on pituitary cells, but also on cells in various tumors, e.g. of the breast and ovaries. These receptors might mediate a direct antiproliferative effect of LHRH receptor antagonists on the tumor.

The peptide LHRH receptor agonists and antagonists are mostly decapeptides whose bioavailability is inadequate for oral administration. They are typically given as solutions for injection or as depot formulation, subcutaneously or intramuscularly. This application is associated with inconveniences for the patient, and the compliance suffers. In addition, synthesis of the decapeptides is complicated and costly.

It is therefore sensible to look for non-peptide LHRH receptor antagonists which, besides high activity, have an improved metabolic stability and can be administered orally.

PRIOR ART

Compared with peptide LHRH receptor agonists and antagonists, as yet no non-peptide compound is approved and in clinical use for any of the possible indications. The current state of development in the area of LHRH receptor agonists and antagonists is described in the reviews by Y.-F. Zhu et al., *Expert Opin. Therap. Patents* 14(2), 187-199 (2004), Y.-F. Zhu et al., *Ann. Rep. Med. Chem.* (39), 99-110 (2004), F. C. Tucci et al., *Curr. Opin. Drug Discovery & Development* 7(6), 832-847 (2004), R. E. Armer, *Curr. Med. Chem.* 11, 3017-3028 (2004) and M. V. Chengalvala et al., *Curr. Med. Chem.—Anti-Cancer Agents*, 3, 399-410 (2003). The former publication contains a comprehensive list of the published patent specifications describing the synthesis and use of low molecular weight LHRH receptor antagonists.

Among the first examples of non-peptide LHRH receptor antagonists is the 4-oxothieno[2,3-b]pyridine structure, which was described by N. Cho et al. in *J. Med. Chem.* 41, 4190-4195 (1998). Although these compounds, such as, for example, T-98475, have a high receptor affinity; their solubility in water is very poor and their bioavailability is low. Based on this lead structure, numerous further developments have been carried out, examples which may be mentioned being the publications of the international applications WO 95/28405, WO 96/24597, WO 97/14697 and WO 97/41126. The synthesis of thieno[2,3-d]pyrimidine-2,4-diones as orally available LHRH receptor antagonists is described by S. Sasaki et al., in *J. Med. Chem.* 46, 113-124 (2003).

Novel 1-arylmethyl-5-aryl-6-methyluracils are described by Z Guo et al., in *J. Med. Chem.* 47, 1259-1271 (2004). The preparation of N-[(hetero)arylmethyl]benzene-sulfonamides as potent non-peptide LHRH receptor antagonists is disclosed in WO 03/078398. The patent application WO 02/11732 describes tricyclic pyrrolidines as LHRH receptor antagonists. Substituted pyridin-4-ones as LHRH receptor antagonists are disclosed in WO 03/13528 and substituted 1,3,5-triazine-2,4,6-triones in WO 03/11839.

The syntheses and biological activities of erythromycin A derivatives having LHRH receptor antagonistic activity is described by J. T. Randolph et al., in *J. Med. Chem.* 47(5), 1085-1097 (2004). Selected derivatives show an oral activity on the LH level in the castrated rats model.

Quinoline derivatives as non-peptide LHRH antagonists are disclosed for example in WO 97/14682. Substituted 2-arylindoles are described inter alia in WO 97/21435, WO 97/21703, WO 98/55116, WO 98/55470, WO 98/55479, WO 99/21553, WO 00/04013 as LHRH receptor antagonists. Correspondingly substituted aza-2-arylindoles are claimed inter alia in WO 99/51231, WO 99/51596, WO 00/53178 and WO 00/53602 as LHRH receptor antagonists. Advantageous biological or biophysical data for these compounds are not disclosed.

The patent EP 0 679 642 B1 describes fused heterocyclic compounds as LHRH receptor antagonists. The basic tetrahydrocarbazole structure is, however, not the subject matter of the invention described therein.

1,2,3,4-Tetrahydrocarbazolecarboxylic acids are described in the patent EP 0 239 306 B1 as prostaglandin antagonists. An LHRH receptor antagonistic effect is neither described nor obvious. U.S. Pat. No. 3,970,757 discloses tetrahydrocarbazole derivatives as gastric anti-secretory agents. However, an LHRH receptor antagonistic effect of this type of structure is neither described nor obvious. EP 603 432 B1 and U.S. Pat. No. 5,708,187 describe tetrahydrocarbazole derivatives as 5HT1 agonists inter alia for the treatment of migraine.

However, an LHRH receptor antagonistic effect is neither described nor obvious. WO 2005/033099 A2 describes tetrahydrocarbazole derivatives as dipeptidyl peptidase IV inhibitors. However, an LHRH receptor antagonistic effect is neither described nor obvious. There is no reference to an LHRH receptor antagonistic effect, and the disclosed structures differ from the compounds of the present invention. D. J. Davies et al. describe in *J. Med. Chem.* 41, 451-467 (1998) tetrahydrocarbazole derivatives having a melatonin agonistic or antagonistic effect. However, an LHRH receptor antagonistic effect is neither described nor obvious. Tetrahydrocarbazole derivatives are described by S. J. Shuttleworth et al. in *Bioorg. Med. Chem. Lett.* 14, 3037-3042 (2004) as partial agonists of the neuromedin B receptor. However, an LHRH receptor antagonistic effect is neither described nor obvious. R. Millet et al. describe in *Letters in Peptide Science* 6, 221-233 (1999) tetrahydrocarbazole derivatives as $NK_1/NK_2$ ligands. The disclosed structures differ from the compounds of the present invention. Moreover, an LHRH receptor antagonistic effect is neither described nor obvious. Solid-phase synthesis of 3-amino-3'-carboxytetrahydrocarbazoles is in Koppitz et al., *THL* 46(6), 911-914 (2005). An LHRH receptor antagonistic effect is neither described nor obvious.

Tetrahydrocarbazole derivatives as peptidomimetic LHRH receptor antagonists having good receptor affinity are disclosed for example in WO 03/051837 (DE 101 64 564 A1). The physicochemical and metabolic properties of these compounds do not, however, make them suitable in an optimal manner for an oral dosage form.

A number of publications provide an overview of the state of development of neurokinin antagonists. G. Giardina et al., *IDrugs* 6(8), 758-772 (2003), provide an overview of the current patent literature. V. Leroy et al., *Expert Opinion on Investigational Drugs* 9(4), 735-746 (2000), and C. Swain et al., *Annual Reports in Medicinal Chemistry* 34, 51-60 (1999) describe the state of development relating to neurokinin receptor antagonists, while, for example, R. M. Navari et al., *Cancer Investigation* 22(4) 569-576 (2004) describes the results of clinical studies in which NK1 receptor antagonists were employed to control chemotherapy-induced emesis. R. G. Hill et al. describe in *Pain,* 523-530 (2003) neurokinin receptor antagonists as potential analgesics, while A. von Sprecher et al. in *IDrugs* 1(1), 73-91 (1998), describe neurokinin receptor antagonists as potential active ingredients for the therapy of inflammations and rheumatoid arthritis. R. Millet et al. describe in *Letters in Peptide Science* 6, 221-233 (1999) tetrahydrocarbazole derivatives as $NK_1/NK_2$ ligands. The disclosed structures differ from the compounds of the present invention.

OBJECT OF THE INVENTION

The object of the present invention is to provide novel compound which have improved oral bioavailability and improved metabolic stability and which can be employed for the treatment of pathological conditions mediated by GPCRs in mammals and in particular in humans. It is preferably intended that the novel compounds display their biological action via an antagonistic inhibition of the LHRH receptor. The novel compound we intended to be suitable for achieving the desired effect in a dosage which is acceptable for use and dose-dependently in an oral formulation. For this it is necessary to be able to use the novel compounds as pharmacologically active ingredients in a medicament in mammals or humans.

The inventive object is achieved in a surprising manner through the provision of the novel, improved tetrahydrocarbazole derivatives of the general formula (I) below.

BRIEF DESCRIPTION OF THE DRAWINGS

FIGS. 1-7 show the measured competition plots of the LHRH receptor-ligand binding assays with [$^{125}$I][D-Trp6]-LH-RH and the selected substances (7, 48, 66, 67, 68, 75 and 76).

FIGS. 8-11 show competition plots measured in the NK1 and NK2 receptor-ligand binding assays with [Sar$^9$, Met($O_2$)$^{11}$]-SP for NK1 and [Nle$^{10}$]-NKA(4-10) for NK2, and the selected substances (68 and 76).

DETAILED DESCRIPTION OF THE INVENTION

A first aspect of the present invention relates to novel tetrahydrocarbazole compounds of the general formula (I):

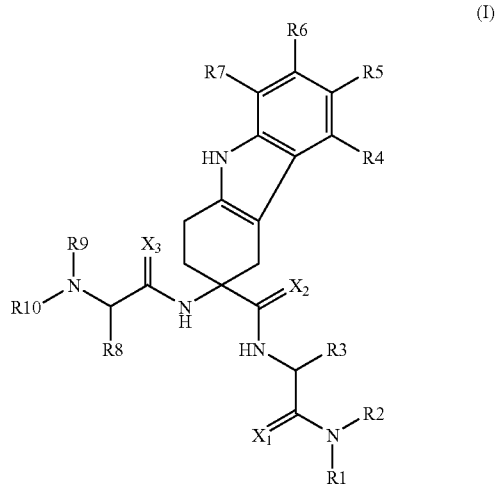

in which:
$X_1$ is S or O,
$X_2$ and $X_3$ are independently of one another O or geminally linked $H_2$,
R1 and R2 are independently of one another selected from the group consisting of —H, aryl, alkyl and arylalkyl radicals which are optionally substituted in the alkyl and/or aryl group by tip to 3 substituents independently selected from the group consisting of -Hal, —CN and —O-alkyl, where R1 and R2 are in particular each a hydrogen atom,
R3 is an alkyl, arylalkyl or heteroarylalkyl radical, which are optionally substituted by tip to 3 substituents independently selected from the group consisting of -Hal, —CN, —CO—O—R12, —CO—NR12R12', —OH, —O—R13, —O—CO—R13, —O—$SO_2$—OR12, —O—$SO_2$—R12, —$SO_2$—OR12, —SO—R12, —O—PO(OR12)(OR12'), —O—PO(NR12R12')$_2$, —O—CO—O—R13, —O—CO—NR12R12', —O—CS—NR12R12', —S—R12, —NR12R12', —NH—CO—R13, —NH—$SO_2$—R12, —NH—CO—O—R13, —NH—CO—NHR12, —NH—C(NH)—$NH_2$,
R4, R5, R6 and R7 are selected independently of one another from the group consisting of H, -Hal, —CN, —$CONH_2$, —COOH, —$CF_3$, —O-alkyl, —$OCF_3$, —$NO_2$, and alkyl, arylalkyl and heteroarylalkyl radicals;
R9 is a hydrogen atom, an alkyl, an aryl, a heteroaryl, an arylalkyl or a heteroarylalkyl radical, preferably a hydrogen atom;
R10 is a hydrogen atom, or the radical —R11, —CO—R11, —CO—OR11, —CO—NHR11, —C(NH)—NHR11, —$SO_2$—R11, or —$SO_2$—NHR11;
R11 is an alkyl, an aryl, a heteroaryl, an arylalkyl or a heteroarylalkyl radical, which are optionally substituted by one or more substituents independently selected from the group consisting of -Hal, —CN, -alkyl, —$CF_3$, —$OCF_3$, —OH, —O-alkyl, and —O—($CH_2CH_2$—O)$_n$—$CH_3$;
R8 is —$C_1$-$C_6$-alkyl-aryl or —$C_1$-$C_6$-alkyl-heteroaryl, where the aryl or heteroaryl group is substituted by tip to three, i.e. by at least one, two or three substituents, preferably by one substituent, independently selected from the group consisting of —O—($CH_2CH_2$—O)$_n$—$CH_3$, —O—CO—R12, —O—CO—(CH$_2$CH$_2$—O)$_n$—CH$_3$, —O—SO$_2$—OR12, —O—SO$_2$—R12, —O—PO(OR12)(OR12'), —O—PO(NR12R12')$_7$, —O—CO—OR13, —O—CO—NR12R12', and —O—CS—NR12R12', or, where, however, at least
(i) X$_1$ is S, or
(ii) R10 is not H, and R11 is an arylalkyl or heteroarylalkyl radical, which are substituted in the aryl or heteroaryl group by one or more substituents, preferably by one, two or three substituents, independently selected from the group consisting of Hal, —CN, -alkyl, —CF$_3$, —OCF$_3$, —OH, —O-alkyl, and —O—(CH$_2$CH$_2$—O)$_n$—CH$_3$.

R8 also assumes the meanings indicated for R3;

R12 and R12' are independently of one another H, or an alkyl, arylalkyl, aryl, heteroarylalkyl, or heteroaryl radical, preferably hydrogens.

R13 is selected from an alkyl, arylalkyl, aryl, heteroarylalkyl, and heteroaryl radical, or is the group —(CH$_2$CH$_2$—O)$_n$—CH$_3$, and n is an integer from 1 to 10, preferably 1 to 6.

The terms indicated for explanation of the compounds of the general formula (I) always, unless indicated otherwise in the description or in the claims, have the following meanings: the term "substituted" means that the corresponding radical or group has one or more substituents. Where a radical has a plurality of substituents, and a selection of various substituents is specified, the substituents are selected independently of one another and need not be identical. The term "unsubstituted" means that the corresponding group has no substituent. The term "optionally substituted" means that the corresponding group is either unsubstituted or substituted by one or more substituents. The term "substituted by up to 3 substituents" means that the corresponding radical or group is substituted either by one or by two or three substituents.

The term "halogen atom" or "halogen substituent" (Hal-) refers to one, where appropriate, a plurality of fluorine (F, fluoro), bromine (Br, bromo), chlorine (Cl, chloro), or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. "Halogen" preferably means a fluorine or chlorine atom.

The term "alkyl" includes for the purposes of this invention acyclic saturated or partially unsaturated hydrocarbons having C1-C12 carbon atoms, which may be straight-chain or branched. The term "alkyl" preferably stands for alkyl chains of 1 to 8, particularly preferably 1 to 6, carbon atoms Examples of suitable alkyl radicals are methyl, ethyl, n-propyl, isopropyl, n-butyl, sec-butyl, tert-butyl, n-pentyl, tert-pentyl, 2- or 3-methyl-pentyl, n-hexyl, n-heptyl, n-octyl, n-nonyl, n-decyl, n-undecyl, n-dodecyl, propenyl, butenyl, pentenyl, hexenyl and octadienyl. The term "alkyl" likewise stands for a saturated or partially unsaturated cycloalkyl radical, preferably from the group of cyclo(C3-C8)alkyl. Examples of suitable cycloalkyl radicals are cyclopropyl, cyclobutyl, cyclopentyl, cyclohexyl, cycloheptyl, cyclooctyl, cyclohexenyl, cyclopentenyl, cyclooctadienyl and others. In addition, the term "alkyl" includes cycloalkylalkyl groups, with preference for the cyclo(C3-C8)alkyl-(C1-C4)alkyl radical. Examples thereof are cyclopropylmethyl, cyclohexylmethyl, cyclopentylethyl, cyclohexenylethyl. Thus, the term C$_1$-C$_4$-alkyl includes at least the following groups: methyl, ethyl, n-propyl, isopropyl, propenyl, cyclopropyl, n-butyl, sec-butyl, tert-butyl, cyclobutyl, cyclopropyl-methyl, and butenyl. Particularly preferred as C$_1$-C$_4$-alkyl are isopropyl, sec-butyl, and cyclopropylmethyl.

Such alkyl radical may be unsubstituted or optionally also mono- or polysubstituted, where the substituents may be identical or different and be bonded in each or more than one desired and possible position of the alkyl. In the case of a mono- or poly-halogen-substituted alkyl radical, substitution with fluorine and/or chlorine atoms is preferred. Examples of such radicals are fluoromethyl, trifluoromethyl and pentafluoroethyl.

"Aryl" refers to aromatic hydrocarbon systems having 3 to 14, preferably 5 to 14, carbon atoms, which may also be fused to further saturated, (partially) unsaturated or aromatic ring systems. Examples of "aryl" are inter alia phenyls, naphthyls and anthracenyls, but also indanyls, indenyls, or 1,2,3,4-tetrahydronaphthyls; phenyl is particularly preferred for the purposes of the present invention. Such aryl radical may be unsubstituted or optionally also mono- or polysubstituted, where the substituents may be identical or different and be bonded in each or more than one desired and possible position of the aryl.

"Heteroaryl" refers to a 5-, 6- or 7-membered cyclic aromatic radical which comprises at least 1, where appropriate also 2, 3, 4 or 5, heteroatoms, preferably nitrogen, oxygen and/or sulfur, where the heteroatoms are identical or different. The number of N atoms is preferably between 0 and 3, and that of the oxygen and sulfur atoms is between 0 and 1. The term "heteroaryl" also includes systems in which the heterocycle is part of a bi- or polycyclic system, it being possible for the linkage of the heteroaryl radical to the compounds of the general formula (I) to take place via any desired and possible ring member of the heteroaryl radical. Examples of "heteroaryl" include pyrrolyl, thienyl, furyl, imidazolyl, thiazolyl, isothiazolyl, oxazolyl, isoxazolyl, pyrazolyl, pyridinyl, pyrimidinyl, pyrazinyl, indolyl, quinolinyl, and isoquinolinyl. Such heteroaryl radicals may be unsubstituted or optionally mono- or polysubstituted, where the substituents may be identical or different and be bonded in each or more than one desired and possible position of the heteroaryl.

"Arylalkyl" or "heteroarylalkyl" refer to radicals in which the aryl or heteroaryl radical is linked via a C$_1$ C$_8$-alkyl group to the compound of the general formula (I), where the alkyl, aryl and heteroaryl groups have the meanings defined above. Preferred "arylalkyl" groups are phenyl-C$_1$-C$_4$-alkyl radicals, preferably benzyl or phenylethyl radicals.

A "ring system" refers to a mono- or polycyclic system of 3 to 14, preferably 5 or 6 to 14 ring atoms which may be exclusively carbon atoms. However, the ring system may also comprise 1, 2, 3, 4, or 5 heteroatoms, in particular nitrogen, oxygen and/or sulfur. The ring system may be saturated, mono- or polyunsaturated or entirely or partly aromatic, and in the case of a ring system consisting of at least two rings the rings may be fused or spiro- or otherwise connected.

As mentioned above in connection with the general formula (I), the compounds of the invention may, because they have at least one center of asymmetry, exist in the form of their racemates, in the form of the pure enantiomers and/or diastereomers or in the form of mixtures of these enantiomers and/or diastereomers The mixtures may have any desired mixing ratio of the stereoisomers.

Preferred compounds of the general formula (I) are those which are in the R configuration at the carbon atom substituted by —NH—CX$_3$— and —CX$_3$—NH—, i.e. have the following general formula (I-a):

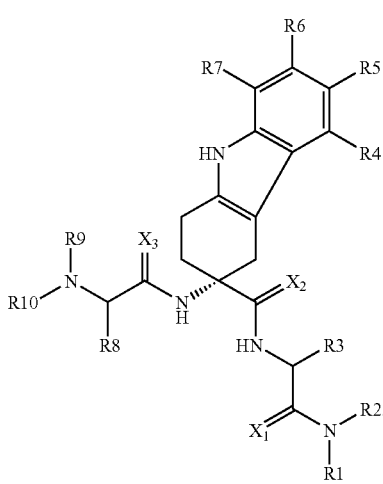

(I-a)

Particularly preferred compounds of the general formula (I) are those which are in the R configuration at the carbon atom substituted by —NH—CX$_3$— and —CX$_2$—NH—, in the S configuration at the carbon atom substituted by —CX$_3$—NH—, —R8 and —NR9R10, and likewise in the S configuration at the carbon atom substituted by —NH—CX$_2$—, —R3 and —CX$_1$—NR1R2, i.e. have the naturally occurring S configuration of the corresponding amino acids at these stereo centers. These compounds have the following general formula (I-b):

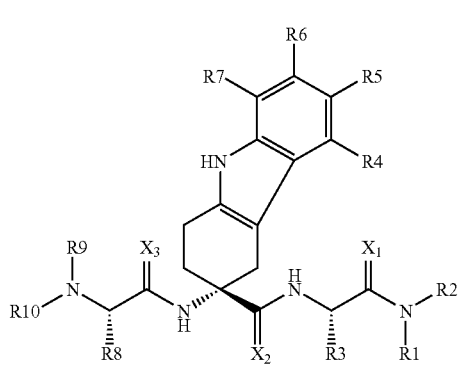

(I-b)

Where possible, the compounds of the invention may be in the form of the tautomers.

Thus, for example, the compounds of the invention of the general formula (I) which have one or more centers of chirality and which occur as racemates or as diastereomer mixtures can be fractionated by methods known per se into their optical pure isomers, i.e. enantiomers or diastereomers. The separation of the compounds of the invention or their building blocks (amino acids) can take place by column separation on chiral or nonchiral phases or by recrystallization from an optionally optically active solvent or with use of an optically active acid or base or by derivatization with an optically active reagent such as, for example, an optically active alcohol, and subsequent elimination of the radical.

The compounds of the invention of the general formulae (I, Ia and Ib) can, if they have a sufficiently basic group such as, for example, a secondary or tertiary amine, be converted with inorganic and organic acids into salts. The pharmaceutically acceptable salts of the compounds of the invention of the general formulae (I, Ia and Ib) are preferably formed with hydrochloric acid, hydrobromic acid, sulfuric acid, phosphoric acid, methanesulfonic acid, p-toluenesulfonic acid, carbonic acid, formic acid, acetic acid, sulfoacetic acid, trifluoroacetic acid, oxalic acid, malonic acid, maleic acid, succinic acid, tartaric acid, racemic acid, malic acid, embonic acid, mandelic acid, fumaric acid, lactic acid, citric acid, taurocholic acid, glutamic acid or aspartic acid. The salts which are formed are, inter alia, hydrochlorides, hydrobromides, sulfates, phosphates, methanesulfonates, tosylates, carbonates, bicarbonates, formates, acetates, sulfoacetates, triflates, oxalates, malonates, maleates, succinates, tartrates, malates, embonates, mandelates, fumarates, lactates, citrates and glutamates. The stoichiometry of the salts formed from the compounds of the invention may moreover be an integral or non-integral multiple of one.

The compounds of the invention of the general formulae (I, Ia and Ib) can, if they contain a sufficiently acidic group such as, for example, the carboxy, sulfonic acid, phosphoric acid or a phenolic group, be converted with inorganic and organic bases into their physiologically tolerated salts. Examples of suitable inorganic bases are sodium hydroxide, potassium hydroxide, calcium hydroxide, and of organic bases are ethanolamine, diethanolamine, triethanolamine, cyclohexylamine, dibenzylethylenediamine and lysine. The stoichiometry of the salts formed from the compounds of the invention can moreover be an integral or non-integral multiple of one.

It is likewise possible for the compounds of the invention of the general formulae (I, Ia and Ib) to be in the form of their solvates and, in particular, hydrates which can be obtained for example by crystallization from a solvent or from aqueous solution. It is moreover possible for one, two, three or any number of solvate or water molecules to combine with the compounds of the invention to give solvates and hydrates.

It is known that chemical substances form solids which exist in different order states which are referred to as polymorphic forms or modifications. The various modifications of a polymorphic substance may differ greatly in their physical properties. The compounds of the invention of the general formulae (I, Ia and Ib) can exist in various polymorphic forms, and certain modifications may moreover be metastable. All these polymorphic forms of the compounds of the general formulae (I, Ia and Ib) are to be regarded as belonging to the invention.

It is likewise possible for the compounds of the invention of the general formulae (I, Ia and Ib) to be in the form of any desired prodrugs such as, for example, esters, carbonates or phosphates, in which cases the actually biologically active form is released only through metabolism.

It is known that chemical substances are converted in the body into metabolites which may where appropriate likewise elicit the desired biological effect—in some circumstances even in more pronounced form.

It is known for thioamides (X$_1$=S) for example (Casarett & Doull's "Toxicology, the Basic Science of Poisons", Chapter 6: Biotransformation of Xenobiotics, C. D. Klaassen Ed., McGraw-Hill 2001; D. M. Clayton, Biochem. Soc. Trans., 1978, 6(1), 94-96) that they can also be metabolized to thioamide S-oxides. These substances can also be obtained by synthesis from the corresponding thioamides by oxidation with hydrogen superoxide (H$_2$O$_2$) (J. R. Cashman et al., J. Org. Chem., 1982, 47 (24), 4645-4650). Thus, compound 68 is oxidized for example to (R)-8-chloro-6-fluoro-3-((S)-2-[2-(2-fluorophenyl)acetylamino]-3-methylpentanoylamino)-2,3,4,9-tetrahydro-1H-carbazole-3-carboxylic acid ((S)-2-methyl-1-thiocarbamoylbutyl)amide S-oxide, and compound 76 is oxidized to (R)-3-((S)-2-[2-(2-fluorophenyl)acetylamino]-

3-methylpentanoylamino)-8-trifluoromethyl-2,3,4,9-tetrahydro-1H-carbazole-3-carboxylic acid ((S)-2-methyl-1-thiocarbamoylbutyl)amide S-oxide.

Corresponding metabolites of the compounds of the general formulae (I, Ia and Ib), especially with $X_1$=—S$^+$—O—, are to be regarded as belonging to the invention.

It may additionally be remarked at this point that the term "receptor ligand" or "ligand" is intended to refer for the purposes of the present invention to every compound which binds in any way to a receptor (the receptor in the present invention is a GPCR receptor, preferably an LHRH receptor) and induces either activation, inhibition and/or another conceivable effect at this receptor. The term "ligand" thus includes agonists, antagonists, partial agonists/antagonists and other ligands which cause an effect at the receptor which is similar to the effect of agonists, antagonists or partial agonists/antagonists. The compounds of the invention of the general formulae (I, Ia and Ib) are preferably antagonists of the LHRH receptor (GnRH receptor).

Preferred compounds of the formulae (I, Ia and Ib) for the purposes of the present invention are those where $X_1$ is an S atom or S$^+$—O$^-$, preferably S atom, and R8 is an alkyl, arylalkyl or heteroarylalkyl radical, where these radicals are optionally substituted by up to 3 substituents independently selected from the group consisting of -Hal, —CN, —CO—O—R12, —CO—NR12R12', —OH, —O—R13, —O—CO—R13, —O—SO$_2$—OR12, —O—SO$_2$—R12, —SO$_2$—OR12, —SO—R12, —O—PO(OR12)(OR12'), —O—PO(NR12R12')$_2$, —O—CO—O—R13, —O—CO—NR12R12', —O—CS—NR12R12', —S—R12, —NR12R12', —NH—CO—R13, —NH—SO$_2$—R12, —NH—CO—O—R13, —NH—CO—NHR12, —NH—C(NH)—NH$_2$, where R12, R12' and R13 have the meanings indicated above.

Further preferred compounds of the formulae (I, Ia and Ib) for the purposes of the present invention are those where
R10 is the radical —R11, —CO—R11, —CO—OR11, —CO—NHR11, —C(NH)—NHR11, —SO$_2$—R1, or —SO$_2$NHR11,
R11 is an arylalkyl or heteroarylalkyl radical which is substituted in the aryl or heteroaryl group by one or more substituents independently selected from the group consisting of Hal, —CN, -alkyl, —CF$_3$, —OCF$_3$, —OH, —O-alkyl, and —O—(CH$_2$CH$_2$—O)$_n$—CH$_3$, and
R8 is an alkyl, arylalkyl or heteroarylalkyl radical which is optionally substituted by up to 3 substituents independently selected from the group consisting of -Hal, —CN, —CO—O—R12, —CO—NR12R12', —OH, —O—R13, —O—CO—R13, —O—SO$_2$—OR12, —SO$_2$—OR12, —O—SO$_2$—R12, —SO—R2, —O—PO(OR12)(OR12'), —O—PO(NR12R12')$_2$, —O—CO—O—R13, —O—CO—NR12R12', —O—CS—NR12R12', —S—R12, —NR12R12', —NH—CO—R13, —NH—SO$_2$—R12, —NH—CO—O—R13, —NH—CO—NHR12, —NH—C(NH)—NH$_2$,
where R12, R12' and R13 have the meanings indicated above.

Further preferred compounds of the formulae (I, Ia and Ib) for the purposes of the present invention are those where R8 is either —C$_1$-C$_6$-alkyl-aryl or —C$_1$-C$_6$-alkyl heteroaryl, where the aryl or heteroaryl group is substituted by one to three, preferably by one, substituents independently selected from the group consisting of —O—(CH$_2$CH$_2$—O)$_n$—CH$_3$, —O—CO—(CH$_2$CH$_2$—O)$_n$—CH$_3$, —O—SO$_2$—OR12, —O—SO$_2$—R12, —O—PO(OR12)(OR12'), —O—PO(NR12R12')$_2$, —O—CO—OR13, —O—CO—NR12R12', and —O—CS—NR12R12', where R12, R12' and R13 have the meanings indicated above.

In a preferred variant of the present invention, at least one, preferably two of the radicals R4, R5, R6, and R7, preferably R5 and R7, are not hydrogen atoms. The radicals R5 and R7 are in particular selected independently of one another from the group consisting of —H, -Hal, —CN, —CF$_3$, —O-alkyl and —OCF$_3$, and are preferably —H, -Hal or —CF$_3$. Particularly preferred compounds are those in which R4 and R6 are each a hydrogen atom, R5 is either —H or -Hal, and R7, independently of R5, is either -Hal or —CF$_3$.

Further preferred compounds of the formulae (I, Ia and Ib) for the purposes of the present invention are those where $X_2$ and $X_3$ are each O.

In a preferred variant of the present invention, R3 is a C$_1$-C$_6$-alkyl radical, preferably a C$_1$-C$_4$-alkyl radical.

Preferred compounds for the purposes of the present invention are those where R1, R2, R9 and also R12 and R12', if present, are each a hydrogen atom.

Further preferred compounds of the general formulae (I, Ia and Ib) are those in which R13 is a phenyl-C$_1$-C$_4$-alkyl radical, or the group —(CH$_2$CH$_2$—O)—CH$_3$.

In preferred compounds of the formulae (I, Ia and Ib), R10 has the meaning —CO—R11, —CO—OR11 or R11, where R11 has the meanings indicated above.

Further preferred compounds of the general formulae (I, Ia and Ib) are those in which R11 is a phenyl-C$_1$-C$_4$-alkyl radical, preferably a benzyl or phenylethyl radical, which is substituted in the phenyl group optionally by one to three, preferably one or two, substituents independently selected from the group consisting of -Hal, —C$_1$-C$_4$-alkyl, —CF$_3$, —OCF$_3$, —OH, —O—C$_1$-C$_4$-alkyl and —O—(CH$_2$CH$_2$—O)$_n$—CH$_3$.

Compounds of the general formulae (I, Ia and Ib) of particular interest for the purposes of the present invention are those where
$X_1$ is either O, S or S$^+$—O$^-$,
$X_2$ and $X_3$ are each O,
R1 and R2 are each a hydrogen atom,
R3 is a C$_1$-C$_6$-alkyl radical, preferably a C$_1$-C$_4$-alkyl radical,
R4 and R6 are each a hydrogen atom,
R5 is either a hydrogen atom or Hal,
R7 is either Hal or —CF$_3$,
R9 is a hydrogen atom,
R10 is the radical —CO—R11 or —CO—OR11 or the radical R11,
R11 is a phenyl-C$_1$-C$_4$-alkyl radical, preferably a benzyl or phenylethyl radical, which is substituted in the phenyl group optionally by one to three, preferably one or two, substituents independently selected from the group consisting of -Hal, —C$_1$-C$_4$-alkyl, —CF$_3$, —OCF$_3$, —OH, —O—C$_1$-C$_4$-alkyl and (CH$_2$CH$_2$—O)$_n$—CH$_3$, and
R8 is a phenyl-C$_1$-C$_4$-alkyl radical, preferably a benzyl or phenylethyl radical, which is substituted in the phenyl group by a substituent selected from the group consisting of —O—(CH$_2$CH$_2$—O)$_n$—CH$_3$, —O—CO—(CH$_2$CH$_2$—O)$_n$—CH$_3$, and —O—PO(OR12)(OR12'), —O—CO—OR13, or,
where, however, at least
(i) $X_1$ is S, or
(ii) R11 is a phenyl-C$_1$-C$_4$-alkyl radical, preferably a benzyl or phenylethyl radical, which is substituted in the phenyl group by at least one of the abovementioned substituents, i.e. independently selected from the group consisting of -Hal, —C$_1$-C$_4$-alkyl, —CF$_3$, —OCF$_3$, —OH, —O—C$_1$-C$_4$-alkyl and —O—(CH$_2$CH$_2$—O)$_n$—CH$_3$, R8 is also a $C_1$-$C_6$-alkyl, preferably a $C_1$-$C_4$-alkyl radical, or a phenyl-$C_1$-$C_4$-alkyl radical, preferably a benzyl or phenylethyl radical, the radicals optionally being substituted by a substituent selected from the group consisting of —OH, —O—R13, and —NR12R12';

R12, R12' are independently of one another H, or a $C_1$-$C_4$-alkyl, benzyl or phenylethyl radical, preferably H;

R13 is selected from a $C_1$-$C_4$-alkyl, phenyl-$C_1$-$C_4$-alkyl, and phenyl radical, or is the group —(CH$_2$CH$_2$—O), —CH$_3$, and is preferably a benzyl or phenethyl radical, and n is an integer from 1 to 6, preferably from 1 to 4.

Further preferred compounds of the invention of the general formulae (I, Ia and Ib) are those in which the radical $X_1$ is a sulfur atom.

In particular, the following compounds of the general formula (I), or (1-a) or (1-b), are to be regarded as particularly preferred:

Compounds in which $X_1$ is S or $S^+$—O—, preferably S, R3 and R8 are each a $C_1$-$C_4$-alkyl radical, R4 and R6 are each a hydrogen atom, R5 and R7 are each Hal, or R5 is a hydrogen atom and R7 is the group —CF$_3$, R10 is the radical —CO—R11, R11 is a benzyl or phenylethyl radical which is substituted in the phenyl group by one or two substituents independently selected from the group consisting of -Hal, —OCF$_3$, and —OCH$_3$.

Compounds in which $X_1$ is O, R3 is a $C_1$-$C_4$-alkyl radical, R4 and R6 are each a hydrogen atom. $R_5$ and $R_7$ are each Hal, or $R_5$ is a hydrogen atom and R7 is the group —CF$_3$. R10 is the radical —CO—R11 or —CO—OR11 or the radical R11, R11 is a benzyl or phenylethyl radical which is substituted in the phenyl group by one or two Hal atoms, and R8 is a $C_1$-$C_4$-alkyl, benzyl or phenylethyl radical, where the phenyl radical is optionally substituted by —OH.

Compounds in which $X_1$ is S or $S^+$—O$^-$, preferably S, R3 is a $C_1$-$C_4$-alkyl radical, R4 and R6 are each a hydrogen atom, R5 and R7 are each Hal, R10 is the radical —CO—OR1, R11 is a benzyl or phenylethyl radical which is substituted in the phenyl group where appropriate by one or two Hal atoms, and R8 is a $C_1$-$C_4$-alkyl, benzyl or phenylethyl radical, where the phenyl radical is optionally substituted by —OH.

Compounds in which $X_1$ is O or S or $S^+$—O$^-$, preferably O or S. R3 is a $C_1$-$C_4$-alkyl radical, R4 and R6 are each a hydrogen atom, R5 and R7 are each Hal, or R5 is a hydrogen atom and R7 is the group —CF$_3$, R10 is the radical —CO—R11 or —CO—OR11, R11 is a benzyl or phenylethyl radical which is substituted in the phenyl group where appropriate by one or two Hal atoms, and R8 is a benzyl or phenylethyl radical which is substituted in the phenyl group by a —O—PO(OH); radical.

The most preferred compounds of the general formula (I) are the following:

4-chlorobenzyl {(S)-1-[(R)-3-((S)-1-carbamoyl-2-methylpropylcarbamoyl)-6,8-dichloro-2,3,4,9-tetrahydro-1H-carbazol-3-ylcarbamoyl]-2-methylpropyl}carbamate (1), 4-chlorobenzyl {(S)-1-[(R)-3-((S)-1-carbamoyl-2-methylpropylcarbamoyl)-6,8-dichloro-2,3,4,9-tetrahydro-1H-carbazol-3-ylcarbamoyl]-2-methylbutyl}carbamate (2), 4-chlorobenzyl {(S)-1-[(R)-3-((S)-carbamoyl-2-methylbutylcarbamoyl)-6,8-dichloro-2,3,4,9-tetrahydro-1H-carbazol-3-ylcarbamoyl]-2-methylbutyl}carbamate (3), (R)-6,8-dichloro-3-{(S)-2-[2-(2-fluorophenyl)acetylamino]-3-methylpentanoylamino}-2,3,4,9-tetrahydro-1H-carbazole-3-carboxylic acid ((S)-1-carbamoyl-2-methylbutyl) amide (4).

(R)-6,8-dichloro-3-{(S)-2-[2-(3-fluorophenyl)acetylamino]-3-methylpentanoylamino}-2,3,4,9-tetrahydro-1H-carbazole-3-carboxylic acid ((S)-1-carbamoyl-2-methylbutyl) amide (5), 2-chlorobenzyl {(S)-1-[(R)-3-((S)-carbamoyl-2-methylbutylcarbamoyl)-6,8-dichloro-2,3,4,9-tetrahydro-1H-carbazol-3-ylcarbamoyl]-2-methylbutyl}carbamate (6), benzyl {(S)-1-[(R)-6,8-dichloro-3-((S)-2-methyl-1-thiocarbamoylbutylcarbamoyl)-2,3,4,9-tetrahydro-1H-carbazol-3-ylcarbamoyl]-2-methylbutyl}carbamate (7), benzyl 4-{(S)-3-benzyloxycarbonylamino-3-[(R)-3-((S)-1-carbamoyl-2-methylbutylcarbamoyl)-6,8-dichloro-2,3,4,9-tetrahydro-1H-carbazol-3-ylcarbamoyl]propyl}phenylcarbonate (8), benzyl[(S)-[(R)-3-((S)-1-carbamoyl-2-methylbutylcarbamoyl)-6,8-dichloro-2,3,4,9-tetrahydro-1H-carbazol-3-ylcarbamoyl]-2-(4-phosphonooxyphenyl)ethyl]carbamate (9).

benzyl[(S)-1-[(R)-6,8-dichloro-3-((S)-2-methyl-1-thiocarbamoylbutylcarbamoyl)-2,3,4,9-tetrahydro-1H-carbazol-3-ylcarbamoyl]-3-(4-hydroxyphenyl)propyl]carbamate (10), benzyl[(S)-1-[(R)-3-((S)-carbamoyl-2-methylbutylcarbamoyl)-6,8-dichloro-2,3,4,9-tetrahydro-1H-carbazol-3-ylcarbamoyl]-3-(4-phosphonooxyphenyl)propyl]-carbamate (11), benzyl[(S)-1-[(R)-6,8-dichloro-3-((S)-2-methyl-1-thiocarbamoylbutylcarbamoyl)-2,3,4,9-tetrahydro-1H-carbazol-3-ylcarbamoyl]-3-(4-phosphonooxyphenyl)propyl]carbamate (12), (R)-6,8-dichloro-3-{(S)-2-[2-(2-fluorophenyl)acetylamino]-3-methylpentanoylamino}-2,3,4,9-tetrahydro-1H-carbazole-3-carboxylic acid ((S)-2-methyl-1-thiocarbamoylbutyl)amide (13), (R)-6,8-dichloro-3-[(S)-2-[2-(2-fluorophenyl)acetylamino]-4-(4-hydroxyphenyl)butyrylamino]-2,3,4,9-tetrahydro-1H-carbazole-3-carboxylic acid ((S)-2-methyl-1-thiocarbamoyl-butyl)amide (14), mono(4-{(S)-3-[(R)-6,8-dichloro-3-((S)-2-methyl-1-thiocarbamoylbutylcarbamoyl)-2,3,4,9-tetrahydro-1H-carbazol-3-ylcarbamoyl]-3-[2-(2-fluorophenyl)acetylamino]propyl}phenyl phosphate (15), (R)-6,8-dichloro-3-((S)-2-[3-(4-fluorophenyl)propionylamino]-3-methylpentanoylamino)-2,3,4,9-tetrahydro-1H-carbazole-3-carboxylic acid ((S)-1-carbamoyl-2-methylpropyl)amide (16), (S)-5-[(R)-3-((S)-1-carbamoyl-2-methylpropylcarbamoyl)-6,8-dichloro-2,3,4,9-tetrahydro-1H-carbazol-3-ylcarbamoyl]-5-[3-(4-fluorophenyl)propionylamino]pentylammonium trifluoroacetate (17), (S)-6,8-dichloro-3-{(S)-2-[3-(2-hydroxyphenyl)propionylamino]-3-methylpentanoylamino}-2,3,4,9-tetrahydro-1H-carbazole-3-carboxylic acid ((S)-1-carbamoyl-2-methylbutyl)amide (18), benzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-[4-(2-{2-[2-(2-methoxyethoxy)ethoxy]ethoxy}ethoxy)phenyl]ethyl}carbamate (19).

(R)-6,8-dichloro-3-((S)-2-{3-[2-(2-{2-[2-(2-methoxyethoxy)ethoxy]ethoxy}ethoxy)phenyl]propionylamino}-3-methylpentanoylamino)-2,3,4,9-tetrahydro-1H-carbazole-3-carboxylic acid ((S)-1-carbamoyl-2-methylbutyl) amide (20), (R)-6,8-dichloro-3-((S)-2-{2-[2-(2-{2-[2-(2-methoxyethoxy)ethoxy]ethoxy}ethoxy)phenyl]acetylamino}-3- methylpentanoylamino)-2,3,4,9-tetrahydro-1H-carbazole-3-carboxylic acid ((S)-1-carbamoyl-2-methylbutyl)amide (21), (R)-6,8-dichloro-3-[(S-2-[3-(2-fluorophenyl)propionylamino]-4-(4-hydroxyphenyl)butyrylamino]-2,3,4,9-tetrahydro-1H-carbazole-3-carboxylic acid ((S)-1-carbamoyl-2-methylbutyl)amide (22).

(R)-6,8-dichloro-3-{(S)-2-[3-(2-fluorophenyl)propionylamino]-3-methylpentanoylamino}-2,3,4,9-tetrahydro-1H-carbazole-3-carboxylic acid ((S)-1-carbamoyl-2-methylbutyl)amide (23), benzyl {(S)-1-[(R)-6,8-dichloro-3-((S)-2-methyl-1-thiocarbamoylbutylcarbamoyl)-2,3,4,9-tetrahydro-1H-carbazol-3-ylcarbamoyl]-3-[4-(2-{2-[2-(2-methoxyethoxy)ethoxy]-ethoxy}ethoxy)phenyl]propyl}carbamate (24), benzyl {(S)-1-[(R)-8-chloro-6-fluoro-3-((S)-2-methyl-1-thiocarbamoylbutylcarbamoyl)-2,3,4,9-tetrahydro-1H-carbazol-3-ylcarbamoyl]-2-methylbutyl}carbamate (25), 3-methylbenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate (26), 2,6-difluorobenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate (27), 3,5-difluorobenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate (28), 3,5-dichlorobenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate (29), 3-fluorobenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate (30), 2-fluorobenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate (31), 3-chlorobenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate (32), 3,5-difluorobenzyl {(S)-1-[(R)-3-((S)-1-carbamoyl-2-methylbutylcarbamoyl)-8-chloro-6-fluoro-2,3,4,9-tetrahydro-1H-carbazol-3-ylcarbamoyl]-2-methylbutyl}carbamate (33), 3-fluorobenzyl {(S)-1-[(R)-3-((S)-1-carbamoyl-2-methylbutylcarbamoyl)-8-chloro-6-fluoro-2,3,4,9-tetrahydro-1H-carbazol-3-ylcarbamoyl]-2-methylbutyl}carbamate (34), 2-fluorobenzyl {(S)-1-[(R)-3-((S)-1-carbamoyl-2-methylbutylcarbamoyl)-8-chloro-6-fluoro-2,3,4,9-tetrahydro-1H-carbazol-3-ylcarbamoyl]-2-methylbutyl}carbamate (35).

3-fluorobenzyl[(S)-1-[(R)-3-((S)-1-carbamoyl-2-methylbutylcarbamoyl)-6,8-dichloro-2,3,4,9-tetrahydro-1H-carbazol-3-ylcarbamoyl]-3-(4-hydroxyphenyl)propyl]-carbamate (37), 2-fluorobenzyl[(S)-1-[(R)-3-((S)-1-carbamoyl-2-methylbutylcarbamoyl)-6,8-dichloro-2,3,4,9-tetrahydro-1H-carbazol-3-ylcarbamoyl]-3-(4-hydroxyphenyl)propyl]-carbamate (38), 2-(2-fluorophenyl)ethyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate (40).

2-fluorobenzyl {(S)-1-[(R)-8-chloro-6-fluoro-3-((S)-2-methyl-1-thiocarbamoylbutylcarbamoyl)-2,3,4,9-tetrahydro-1H-carbazol-3-ylcarbamoyl]-2-methylbutyl}-carbamate (41), 3-fluorobenzyl {(S)-1-[(R)-8-chloro-6-fluoro-3-((S)-2-methyl-1-thiocarbamoylbutylcarbamoyl)-2,3,4,9-tetrahydro-1H-carbazol-3-ylcarbamoyl]-2-methylbutyl}carbamate (42), 2-fluorobenzyl[(S)-1-[(R)-6,8-dichloro-3-((S)-2-methyl-1-thiocarbamoylbutylcarbamoyl)-2,3,4,9-tetrahydro-1H-carbazol-3-ylcarbamoyl]-3-(4-hydroxyphenyl)propyl]carbamate (43), 3-fluorobenzyl[(S)-1-[(R)-6,8-dichloro-3-((S)-2-methyl-1-thiocarbamoylbutylcarbamoyl)-2,3,4,9-tetrahydro-1H-carbazol-3-ylcarbamoyl]-3-(4-hydroxyphenyl)propyl]carbamate (45), 3-methoxybenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate (47), 4-fluorobenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate (48), 2-methylbenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate (49), 2,3-dimethoxybenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate (50).

2-methoxybenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate (51), (R)-6,8-dichloro-3-{(S)-2-[2-(2-fluorophenyl)ethylamino]-3-methylpentanoylamino}-2,3,4,9-tetrahydro-1H-carbazole-3-carboxylic acid ((S)-1-carbamoyl-2-methylbutyl)amide (52), 2-trifluoromethylbenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate (53), 3-trifluoromethylbenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate (54), 3-trifluoromethoxybenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate (55).

2-trifluoromethoxybenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate (56), 4-fluorobenzyl {(S)-1-[(R)-6,8-dichloro-3-((S)-2-methyl-1-thiocarbamoylbutylcarbamoyl)-2,3,4,9-tetrahydro-1H-carbazol-3-ylcarbamoyl]-2-methylbutyl}carbamate (57), (R)-6,8-dichloro-3-((S)-2-[2-(4-fluorophenyl)ethylamino]-3-methylpentanoylamino)-2,3,4,9-tetrahydro-1H-carbazole-3-carboxylic acid ((S)-1-carbamoyl-2-methylbutyl)amide (58), (R)-6,8-dichloro-3-{(S)-2-[2-(2,6-difluorophenyl)acetylamino]-3-methylpentanoylamino}-2,3,4,9-tetrahydro-1H-carbazole-3-carboxylic acid ((S)-1-carbamoyl-2-methylbutyl)amide (59), 4-fluorobenzyl {(S)-1-[(R)-8-chloro-6-fluoro-3-((S)-2-methyl-1-thiocarbamoylbutylcarbamoyl)-2,3,4,9-tetrahydro-1H-carbazol-3-ylcarbamoyl]-2-methylbutyl}carbamate (60), (R)-6,8-dichloro-3-{(S)-2-[2-(3-fluorophenyl)ethylamino]-3-methylpentanoylamino}-6-2,3,4,9-tetrahydro-1H-carbazole-3-carboxylic acid {(S)-1-carbamoyl-2-methylbutyl}amide (61), (R)-8-chloro-3-{(S)-2-[2-(2,6-difluorophenyl)acetylamino]-3-methylpentanoylamino}-6-fluoro-2,3,4,9-tetrahydro-1H-carbazole-3-carboxylic acid ((S)-2-methyl-1-thiocarbamoylbutyl)amide (62), (R)-8-chloro-6-fluoro-3-{(S)-2-[2-(4-fluorophenyl)ethylamino]-3-methylpentanoylamino}-2,3,4,9-tetrahydro-1H-carbazole-3-carboxylic acid ((S)-1-carbamoyl-2-methylbutyl)amide (63), 4-fluorobenzyl {(S)-1-[(R)-3-((S)-1-carbamoyl-2-methylbutylcarbamoyl)-8-chloro-6-fluoro-2,3,4,9-tetrahydro-1H-carbazol-3-ylcarbamoyl]-2-methylbutyl}carbamate (64), (R)-8-chloro-6-fluoro-3-{(S)-2-[2-(4-fluorophenyl)acetylamino]-3-methylpentanoylamino}-2,3,4,9-tetrahydro-1H-carbazole-3-carboxylic acid ((S)-2-methyl-1-thiocarbamoylbutyl)amide (65).

(R)-8-chloro-3-{(S)-2-[2-(2,4-difluorophenyl)acetylamino]-3-methylpentanoylamino}-6-fluoro-2,3,4,9-tetrahydro-1H-carbazole-3-carboxylic acid ((S)-2-methyl-1-thiocarbamoylbutyl)amide (66), (R)-8-chloro-6-fluoro-3-{(S)-2-[2-(4-fluorophenyl)ethylamino]-3-methylpentanoylamino}-2,3,4,9-tetrahydro-1H-carbazole-3-carboxylic acid ((S)-2-methyl-1-thiocarbamoylbutyl)amide (67), (R)-8-chloro-6-fluoro-3-{(S)-2-[2-(2-fluorophenyl)acetylamino]-3-methylpentanoylamino}-2,3,4,9-tetrahydro-1H-carbazole-3-carboxylic acid ((S)-2-methyl-1-thiocarbamoylbutyl)amide (68), (R)-8-chloro-6-fluoro-3-{(S)-2-[2-(2-fluorophenyl)acetylamino]-3-methylpentanoylamino}-2,3,4,9-tetrahydro-1H-carbazole-3-carboxylic acid ((S)-1-carbamoyl-2-methylbutyl)amide (69).

(R)-3-{(S)-2-[2-(2-fluorophenyl)acetylamino]-3-methylpentanoylamino}-8-trifluoromethyl-2,3,4,9-tetrahydro-1H-carbazole-3-carboxylic acid ((S)-2-cyclopropyl-1-thiocarbamoylethyl)amide (70).

(R)-3-{(S)-2-[2-(2,6-difluorophenyl)acetylamino]-3-methylpentanoylamino}-8-trifluoromethyl-2,3,4,9-tetrahydro-1H-carbazole-3-carboxylic acid ((S)-2-cyclopropyl-1-thiocarbamoylethyl)amide (71), (R)-8-chloro-6-fluoro-3-{(S)-2-[2-(2-fluorophenyl)acetylamino]-3-methylpentanoylamino}-2,3,4,9-tetrahydro-1H-carbazole-3-carboxylic acid ((S)-2-cyclopropyl-1-thiocarbamoylethyl)amide (72), (R)-3-{(S)-2-[2-(2,6-difluorophenyl)acetylamino]-3-methylpentanoylamino}-8-trifluoromethyl-2,3,4,9-tetrahydro-1H-carbazole-3-carboxylic acid ((S)-2-methyl-1-thiocarbamoylbutyl)amide (73), (R)-3-(S)-2-[2-(2,6-difluorophenyl)acetylamino]-3-methylpentanoylamino)-8-trifluoromethyl-2,3,4,9-tetrahydro-1H-carbazole-3-carboxylic acid ((S)-1-carbamoyl-2-methylbutyl)amide (74), (R)-3-{(S)-2-[2-(2-fluorophenyl)acetylamino]-3-methylpentanoylamino}-8-trifluoromethyl-2,3,4,9-tetrahydro-1H-carbazole-3-carboxylic acid ((S)-1-carbamoyl-2-methylbutyl)amide (75), (R)-3-{(S)-2-[2-(2-fluorophenyl)acetylamino]-3-methylpentanoylamino}-8-trifluoromethyl-2,3,4,9-tetrahydro-1H-carbazole-3-carboxylic acid ((S)-2-methyl-1-thiocarbamoylbutyl)amide (76).

(R)-8-chloro-3-{(S)-2-[2-(2,6-difluorophenyl)acetylamino]-3-methylpentanoylamino}-6-fluoro-2,3,4,9-tetrahydro-1H-carbazole-3-carboxylic acid ((S)-2-cyclopropyl-1-thiocarbamoylethyl)amide (77).

The abovementioned compounds 4, 7, 11, 12, 13, 14, 15, 30, 31, 34, 37, 45, 48, 52, 58, 59, 60, 61, 62, 63, 64, 65, 66, 67, 68, 69, 70, 71, 72, 73, 74, 75 and 76 are moreover very particularly preferred.

The novel tetrahydrocarbazole derivatives of the invention of the general formulae (I, Ia and Ib) as defined above are GPCR ligands. Thus, the aforementioned compounds of the invention are suitable for the treatment and prophylaxis of pathological states mediated by GPCR, and of pathological states which can be influenced by modulation of this receptor, and thus treated. The compounds of the invention can be employed in particular for the inhibition, i.e. as antagonist, of the LHRH receptor or of receptors of the neurokinin family, especially the $NK_1$ and/or $NK_2$ receptor, and are thus suitable for example for the treatment of benign and malignant neoplastic diseases, for the treatment and prevention of nausea and vomiting, for example as a consequence of emetogenic chemotherapy, for the treatment of pain, inflammations and rheumatic and arthritic pathological conditions, in male fertility control, for hormone therapy, in hormone replacement therapy and for the treatment and/or control of female sub- or infertility.

In male fertility control, the compounds of the invention bring about a reduction in spermatogenesis. Combined administration with androgens, e.g. testosterone or testosterone derivatives, such as, for example, testosterone esters, is preferred. The testosterone derivatives can in this case be administered for example by injection, e.g. by intramuscular depot injection.

The compounds of the invention of the general formulae (I, Ia and Ib) can also be employed in female hormone therapy, for example for the treatment of benign hormone-dependent disorders such as endometriosis, uterine fibroids, uterine myomas (uterine leiomyomas), endometrium hyperplasia, dysmenorrhea, and dysfunctional uterine bleeding (menorrhagia, metrorrhagia), where appropriate in combination with other hormones, e.g. estrogens or/and progestins. Particularly preferred are combinations of the LHRH receptor antagonists of the invention and tissue-selective partial estrogen agonists such as Raloxifene®.

The compounds of the invention can also be employed in hormone replacement therapy, for example for treating hot flushes.

The compounds of the invention of the general formulae (I, Ia and Ib) can moreover be employed to control female fertility, for example by switching off the endogenous hormone cycle for controlled induction of ovulation ("COS=controlled ovarian stimulation"), and for the treatment of sterility within the scope of assisted reproduction techniques such as in-vitro fertilization ("IVF").

On the other hand, the novel compounds of the invention of the general formulae (I, Ia and Ib) are also suitable for female contraception. Thus, an LHRH receptor antagonist of the invention can be administered on days 1 to 15 of the female cycle together with estrogen, preferably with very low estrogen dosages. On days 16 to 21 of the cycle of intake, progestagen is added to the combination of estrogen and LHRH receptor antagonist. The LHRH receptor antagonist of the invention can be administered continuously throughout the cycle. It is possible in this way to achieve a reduction in the hormone dosage and thus a reduction in the side effects of nonphysiological hormone levels. It is additionally possible to achieve advantageous effects in women suffering from polycystic ovary syndrome and androgen-dependent disorders such as acne, seborrhea and hirsutism. An improved cycle control compared with previous administration methods is also to be expected.

Further indications are benign prostate hyperplasia (BPH), gonadal protection during chemotherapy, developmental disturbances in early childhood, e.g. pubertas praecox, the treatment of HIV infections or AIDS and of neurological or neurodegenerative disorders, ARC (AIDS related complex), Kaposi sarcoma, tumors originating in the brain and/or nervous system and/or meninges (cf. WO 99/01764), dementia and Alzheimer's disease.

Finally, the compounds of the invention of the general formulae (I, Ia and Ib) as defined above can also be employed for the treatment of malignant hormone-dependent neoplastic diseases such as premenopausal breast cancer, prostate cancer, ovarian cancer, uterine cancer, cervical cancer and endometrial cancer, since they suppress endogenous sex steroid hormones, and in addition are also suitable for the treatment and prevention of nausea and vomiting, for example resulting from emetogenic chemotherapy, or for the treatment of pain, inflammations and rheumatic and arthritic pathological conditions.

The novel compounds of the invention of the general formulae (I, Ia and Ib) as defined above are suitable as GPCR ligands, in particular LHRH receptor antagonists or antagonists of receptors of the neurokinin family, for the treatment of the aforementioned pathological conditions for administration to mammals and in particular humans, but also for veterinary medical purposes. e.g. in domestic and productive animals, but also in wild animals.

The administration can take place in a known manner, for example orally or non-orally, in particular topically, rectally, intravaginally, nasally or by injections or implantation. Oral administration is preferred.

The novel compounds of the invention of the general formulae (I, Ia and Ib) are converted into a form which can be administered and are mixed where appropriate with pharmaceutically acceptable carriers or diluents. Suitable excipients and carriers are described for example in Ullman's Encyclopedia of Technical Chemistry, Vol. 4, (1953), 1-39; Journal of Pharmaceutical Sciences, Vol. 52 (1963), 918 et seq.; H. v. Czetsch-Lindenwald. "Hilfsstoffe für Pharmazie and angrenzende Gebiete"; Pharm. Ind. 2, 1961, 72 et seq., Dr. H. P. Fiedler, "Lexikon der Hilfsstoffe für Pharmazie, Kosmetik and angrenzende Gebiete", Cantor K G, Aulendorf in Wurttemberg, 1971.

Oral administration can take place for example in solid form as tablet, capsule, gel capsule, coated tablet, granulation or powder, but also in the form of a drinkable solution. The novel compounds of the invention of the general formulae (I, Ia and Ib) as defined above can for oral administration be combined with known and ordinarily used, physiologically tolerated excipients and carriers such as, for example, gum arabic, talc, starch, sugars such as, for example, mannitol, methylcellulose, lactose, gelatin, surface-active agents, magnesium stearate, cyclodextrins, aqueous or nonaqueous carriers, diluents, dispersants, emulsifiers, lubricants, preservatives and flavorings (e.g. essential oils). The compounds of the invention can also be dispersed in a microparticulate, e.g. nanoparticulate, composition.

Non-oral administration can take place for example by intravenous, subcutaneous, intramuscular injection of sterile aqueous or oily solutions, suspensions or emulsions, by means of implants or by ointments, creams or suppositories. Administration as sustained release form is also possible where appropriate. Implants may comprise inert materials, e.g. biodegradable polymers or synthetic silicones such as, for example, silicone rubber.

Intravaginal administration is possible for example by means of vaginal rings. Intrauterine administration is possible for example by means of diaphragms or other suitable intrauterine devices. Transdermal administration is additionally provided, in particular by means of a formulation suitable for this purpose and/or suitable means such as, for example, patches.

As already explained above, the novel compounds of the invention of the general formulae (I, Ia and Ib) can also be combined with other active pharmaceutical ingredients. It is possible for the purposes of the combination therapy to administer the individual active ingredients simultaneously or separately, in particular either by the same route (e.g. orally) or by separate routes (e.g. orally and as injection). They may be present and administered in identical or different amounts in a unit dose. It is also possible to use a particular dosage regimen when this appears appropriate. It is also possible in this way to combine a plurality of the novel compounds of the invention of the general formulae (I, Ia and Ib) with one another.

The dosage may vary within a wide range depending on the type of indication, or the severity of the disorder, the mode of administration, the age, gender, bodyweight and sensitivity of the subject to be treated. It is within the ability of a skilled worker to determine a "pharmacologically effective amount" of the combined pharmaceutical composition. Administration can take place in a single dose or a plurality of separate dosages.

A suitable unit dose is, for example, from 0.001 mg to 100 mg of the active ingredient, i.e. at least one compound of the invention of the general formulae (I, Ia and Ib) and, where appropriate, a further active ingredient, per kg of a patient's bodyweight.

A further aspect of the present invention accordingly includes pharmaceutical compositions as described above, comprising one or more of the novel compounds of the invention of the general formulae (I, Ia and Ib) as defined above and, where appropriate, pharmaceutically acceptable carriers and/or excipients. Preferred and particularly preferred pharmaceutical compositions are those comprising at least one of the novel compounds of the invention of the general formulae (I, Ia and Ib) mentioned above as preferred or particularly preferred, in particular at least one of the compounds 1 to 77 specifically mentioned above, with very particular preference for compounds 4, 7, 11, 12, 13, 14, 15, 30, 31, 34, 37, 45, 48, 52, 58, 59, 60, 61, 62, 63, 64, 65, 66, 67, 68, 69, 70, 71, 72, 73, 74, 75 and 76 in this connection. In pharmaceutical compositions of the present invention it is possible, besides at least one compound of the general formulae (I, Ia and Ib) as defined above, for other active pharmaceutical ingredients also to be present, as already detailed above.

In the pharmaceutical compositions of the invention, at least one of the novel compounds of the invention (I) as defined above are present in a pharmacologically effective amount, preferably in a unit dose, e.g. the aforementioned unit dose, specifically and preferably in an administration form which makes oral administration possible.

The present invention additionally provides in a further aspect compounds of the general formulae (I, Ia and Ib) as defined above for use as medicaments. As already explained above, the compounds of the general formulae (I, Ia and Ib) act as GPCR ligands, in particular as antagonists of the LHRH receptor, and are thus particularly suitable for use as medicaments. The compounds of the invention of the general formulae (I, Ia and Ib) for use as medicaments are preferably provided for administration for the treatment or alleviation of the aforementioned medical indications or for contraception.

Preferred tetrahydrocarbazole compound of the invention of the general formulae (I, Ia and Ib) as defined above for use as medicaments are in turn the compounds which have been mentioned above as preferred and particularly preferred compounds, especially the preferred compounds of the invention 1 to 77 specifically mentioned and, unless already included therein, the compounds of the invention mentioned in the examples.

Concerning the pharmaceutical compositions comprising compounds of the invention of the general formulae (I, Ia and Ib), and concerning the use of the compounds of the invention of the general formulae (I, Ia and Ib) as medicaments, reference may be made to that already said in connection with the use of the novel compounds of the invention of the general formulae (I, Ia and Ib) themselves, in relation to possible uses and administrations.

In another aspect, the present invention also provides the use of at least one tetrahydrocarbazole compound of the invention of the general formulae (I, Ia and Ib) as defined above for producing a medicament for the treatment of GPCR-mediated diseases, where the GPCR receptor is preferably the LHRH receptor, and the compounds of the invention preferably act as LHRH receptor antagonists.

Accordingly, in a further aspect, the present invention provides the use of at least one compound of the invention of the general formulae (I, Ia and Ib) as defined above, or of a corresponding pharmaceutical composition, for producing a medicament which acts as LHRH receptor antagonist, preferably for the treatment of benign and malignant neoplastic diseases, for male fertility control, for hormone therapy, for hormone replacement therapy, for controlled ovarian stimulation in the context of in-vitro fertilization (IVF), for the treatment and/or control of female sub- and infertility and for female contraception. Hormone therapy in this connection includes, inter alia, the treatment of endometriosis, uterine leiomyomas, uterine fibroids and benign prostate hyperplasia (BPH). Concerning further indications and explanations of the indications relating to the current aspect of the present invention, reference may be made to the statements made above concerning the first aspect of the present invention, i.e. to the compounds of the invention of the general formulae (I, Ia and Ib) themselves, and the explanations given there.

The compounds of the invention are not only suitable for the treatment or therapy of said pathological conditions, but are equally suitable for the prevention or prophylaxis, and the alleviation (e.g. through suppressing the symptoms) of these pathological conditions or diseases.

The present invention provides in a further aspect the use of a compound (I) of the invention for producing a medicament for the treatment of benign and malignant neoplastic diseases, and for hormone treatment. Preferred and particularly preferred compounds of the invention for this use are the compounds which have already been mentioned at the outset as preferred or particularly preferred compounds of the invention of the general formulae (I, Ia and Ib) themselves as defined above. Very particularly preferred compounds are also the compounds 1 to 77 which are specifically mentioned hereinabove.

The present invention likewise provides a process for producing a medicament for the treatment of GPCR-mediated pathological conditions, the process being characterized by the use of at least one compound of the invention of the general formulae (I, Ia and Ib) or of a corresponding pharmaceutical composition. The explanations given above concerning the preferred and particularly preferred compounds of the invention, and concerning the specific pathological conditions which can be treated, prevented or alleviated by the pharmaceutical composition produced with use of the compounds of the invention are also to be cited for this aspect of the present inventor.

In addition, the present invention provides a method for male fertility control or for female contraception, comprising the administration of an amount, effective for male fertility control or for female contraception, of at least one compound of the invention of the general formulae (I, Ia and Ib), where appropriate in combination with a further active ingredient, to a subject, preferably a mammal and particularly preferably a human The explanations given above concerning further aspects of the present invention in relation to preferred and particularly preferred compounds of the invention, and the explanations in relation to dosage, administration etc. likewise apply here.

In a further aspect, the present invention relates to a method for the treatment of GPCR-mediated pathological conditions. The method comprises the administration of at least one compound (I) of the invention as defined above in a pharmaceutically effective amount to a mammal and in particular to a human, in cases where such a treatment is necessary. As already explained above concerning the novel compounds (I) of the invention, and the pharmaceutical compositions of the invention, it rests with the expert knowledge of a skilled worker to determine a pharmaceutically effective amount, depending on the specific requirements of the individual case. The preferred administration form is oral administration. Administration of one or more of the compounds (I) of the invention in combination with at least one further active ingredient, as already explained above, is also provided. The explanations given concerning the above aspects of the present invention relating to preferred and particularly preferred compounds and to the specific pathological conditions which can be treated, alleviated or prevented also apply to the treatment method mentioned herein. Particularly preferred compounds for this aspect are also compounds 1 to 77.

In addition, the present invention also relates to a method for inhibiting GPCRs, in particular the LHRH receptor or a receptor of the neurokinin family, in a patient, comprising the administration of a pharmaceutically effective amount of at least one compound of the general formulae (I, Ia and Ib) as defined above, where appropriate in combination with a further active ingredient as defined above, to a patient (mammal and in particular human) requiring such a treatment. The preferred and particularly preferred compounds of the invention of the general formulae (I, Ia and Ib) are once again identical to the preferred and particularly preferred compounds mentioned above concerning the other aspects of the present invention, especially the compounds 1 to 77. The explanations above concerning the pathological conditions which can be treated by administration of the compounds of the invention, preferably through their LHRH receptor antagonistic effect, also apply to the treatment method of the invention described herein.

The compounds of the invention of the general formulae (I, Ia and Ib) as defined above can be prepared for example in the following way:

Firstly, the compounds of the invention can be synthesized by preparing the depicted central tetrahydrocarbazole structure

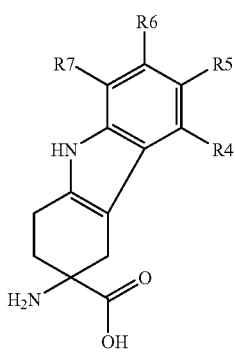

where this optionally protected tetrahydrocarbazole structure already contains the substituents $R_4$ to $R_7$—where appropriate as precursors or in protected form.

The central tetrahydrocarbazole structure is obtainable, for example, by a Fischer indole synthesis, known per se. For this purpose, a suitably substituted cyclohexanone derivative which is provided where appropriate with protective groups is condensed with the particular desired phenylhydrazine derivative which is likewise suitably substituted and, where appropriate, provided with protective groups (e.g. as described by Britten & Lockwood, *J. Chem. Soc. Perkin Trans. I* 1974, 1824 or Maki et al., *Chem. Pharm. Bull.* 1973, 21, 240). The cyclohexane structure is substituted in the 4,4' position by the radicals —COOH and —NH, or where appropriate by the (protected) precursors thereof. The phenylhydrazine structure is substituted where appropriate by the radicals $R^4$ to $R^7$. Phenylhydrazine derivatives which are not commercially available can be prepared by processes known to the skilled worker. Positional isomers resulting where appropriate in the condensation of the cyclohexanone derivative and the phenylhydrazine derivative can be separated by chromatographic methods such as, for example, HPLC.

The radicals $R_{10}R_9NCHR_8CX_3NH$— and $R_1R_2NCX_1CHR_3NHCX_2$— can in principle be introduced and modified in various ways depending on their nature by processes known to the skilled worker, as indicated for example in WO 03/051837 by means of examples and general explanations.

Another process for synthesizing the compounds of the invention of the general formulae (I, Ia and Ib) is the following:

Firstly a basic tripeptide structure is prepared by coupling three suitable amino acids, the first amino acid $AA^1$ comprising the radical R3 as side chain and the third amino acid $AA^3$ comprising the radical R8 or a precursor of R8 as side chain, while the "middle" amino acid $AA^2$ is 3-amino-2,3,4,9-tetrahydro-1-H-carbazole-3-carboxylic acid (abbreviated to Thc). The basic Thc structure can be correspondingly substituted, depending on the substitution pattern of the desired resulting compound of the invention, by the radicals R4 to R7, where appropriate in the form of their precursors or in protected form. The peptide coupling can be carried out by processes known to the skilled worker, e.g. in the solid or liquid phase. Modifications of the substitution pattern can then be undertaken, such as "deprotection" of particular radicals.

The following scheme illustrates the coupling of the amino acids for example on the solid phase:

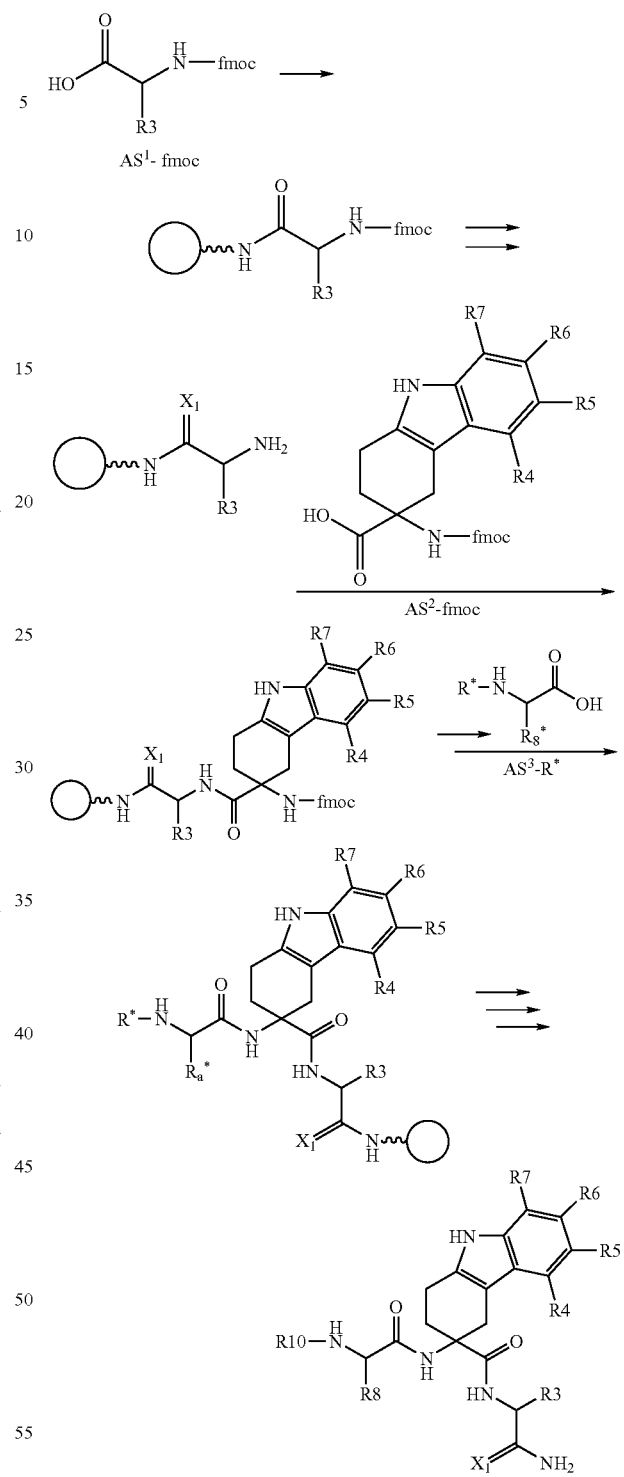

where R* is —CO—O-benzyl (i.e. Z) or any protective group, e.g. Fmoc, where R8* is either —$C_1$-$C_6$-alkylaryl or —$C_1$-$C_6$-alkylheteroaryl, where the aryl or heteroaryl group is substituted by up to three, preferably by one, OH group, or R8* may also—corresponding to the definitions given for R8— have the meaning of R3.

This process is illustrated in detail below for the example of solid-phase and liquid-phase syntheses and for the specific examples 1 to 77.

General Methods for Synthesizing the Compounds of the Invention of the General Formulae (I, Ia and Ib)

The compounds of the invention of the formulae (I, Ia and Ib) are synthesized either by conventional synthesis in solution or else wholly or partly on a solid phase.

Method 1A Solid-Phase Synthesis of LHRH Peptidomimetics

The specific syntheses of the compounds detailed in the examples took place on a solid phase using the semiautomatic SP 650 synthesizer (from Labortec). The standard program is shown in Table 1 below:

TABLE 1

Program for SP 650 synthesizer (from Labortec)

| Step | Function | Solvent/reagent | Time in min | Repetitions |
|---|---|---|---|---|
| 1 | wash | DMF | 2 | 2 |
| 2 | eliminate | 20% piperidine + 1% DBU | 5 | 3 |
| 3 | wash | DMF | 2 | 2 |
| 4 | wash | 2-propanol | 2 | 1 |
| 5 | wash | DMF | 2 | 2 |
| 6 | wash | 2-propanol | 2 | 1 |
| 7 | wash | DMF | 2 | 2 |
| 8 | STOP | | | |
| 9 | addition | Fmoc-AA + HOBt + DIC | | |
| 10 | skip | | | |
| 11 | coupling | | 120-300 | 1 |
| 12 | wash | DMF | 2 | 1 |
| 13 | wash | 2-propanol | 2 | 1 |
| 14 | wash | DMF | 2 | 1 |
| 15 | wash | 2-propanol | 2 | 1 |
| 16 | wash | DMF | 2 | 1 |
| 17 | wash | 2-propanol | 2 | 1 |
| 18 | END | | | |

Elimination of the Fmoc protective group takes place in this case with 20% piperidine and 1% DBU in DMF for 5 minutes. The procedure is carried out a total of three times for 5 minutes each time.

DMF and 2-propanol are used as washing solutions.

Coupling of the first Fmoc-amino acid takes place with HOBt and DIC in DCM and DMF (v/v=1.1).

Coupling of the further Fmoc-amino acids is carried out with HATU and HOAt (0.5M solution in DMF) in the presence of DIPEA.

Method 1Aa Coupling of the First Amino Acid $AA^1$ (Synthesis of Fmoc-$AA^1$-Resin)

Pretreat 1 mmol of Fmoc-resin [Fmoc-2,4-dimethoxy-4'-(carboxymethyloxy)benzhydrylamine linked to aminomethyl-substituted polystyrene resin (200-400 mesh; 0.55 mmol/g] according to synthesizer program, eliminate Fmoc protective group, add 1 mmol of Fmoc-amino acid $AA^1$ (Fmoc-NH—CHR3-COOH), 2 mmol of HOBt in DCM and DMF (v/v=1:1) and 3 mmol of DIC, shake at RT for 3 h and then wash according to program.

Method 1Ab Coupling of the Second Amino Acid $AA^2$ (Synthesis of Fmoc-$AA^2$-$AA^1$-Resin)

Pretreat 1 mmol of Fmoc-$AA^1$-resin according to program, add 2 mmol of Fmoc-amino acid $AA^2$ (Fmoc-Thc-OH), 2 mmol of HATU, 2 mmol of HOAt (0.5M solution in DMF) and 5 mmol of DIPEA and shake at RT for 4-6 h. Check the pH during the reaction and adjust to pH 8-9 by adding DIPEA. After coupling is complete, washing steps according to program.

Method 1Ac Coupling of the Third Amino Acid $AA^3$ (Synthesis of Z-$AA^3$-$AA^2$-$AA^1$-Resin)

Pretreat 1 mmol of Fmoc-$AA^2$-$AA^1$-resin according to program, add 2 mmol of Z-amino acid Z-$AA^3$ (benzyl-O—CO—NH—CHR8*-COOH), 2 mmol of HATU. 2 mmol of HOAt (0.5M solution in DMF) and 5 mmol of DIPEA and shake at RT for 46 h. Check the pH during the reaction and adjust to pH 8-9 by adding DIPEA. After coupling is complete, washing steps according to program.

Method 1Ad Coupling of the Third Amino Acid $AA^3$ (Synthesis of Fmoc-$AA^3$-$AA^2$-$AA^1$-Resin)

Pretreat 1 mmol of Fmoc-$AA^2$-$AA^1$-resin according to program, add 2 mmol of Fmoc-amino acid $AA^3$ (Fmoc-NH—CHR8*-COOH), 2 mmol of HATU, 2 mmol of HOAt (0.5M solution in DMF) and 5 mmol of DIPEA and shake at RT for 4-6 h. Check the pH during the reaction and adjust to pH 8-9 by adding DIPEA. After coupling is complete, washing steps according to program.

Method 1Ae Modification of Fmoc-$AA^3$-$AA^2$-$AA^1$-Resin: Introduction of a Terminal Z Residue (Reaction with Z—Cl)

Pretreat 1 mmol of Fmoc-$AA^3$-$AA^2$-$AA^1$-resin according to program, shake 2 mmol of Z-chloride, 4 mmol of DIPEA and catalytic amounts of DMAP for 3 h and then washing steps according to program.

Method 1Af Introduction of a Terminal Residue R10 where R10 is —CO—R11-Reaction with R11-COOH Pretreat 1 mmol of Fmoc-$AA^3$-$AA^2$-$AA^1$-resin according to program, shake 3 mmol of carboxylic acid R11-COOH, 3 mmol of HOBt and 4 mmol of DIC for 3 h and then washing steps according to program.

Method 1Ag Introduction of a Terminal Residue R10 where R10 is —CO—OR11, and if Appropriate Modification of R8* to R8-Reaction with R—OSu Pretreat 1 mmol of Fmoc-$AA^3$-$AA^2$-$AA^1$-resin according to program, shake 3 mmol of R—OSu, 5 mmol of DIPEA and catalytic amounts of DMAP for 3 h and then wash according to program. If R8* has a free OH group, conversion of this OH group to —O—CO—O—R13 is possible, in which case R11 and R13 are identical radicals.

Method 1Ah Introduction of a Terminal Radical R10 were R10 is —R11-Reaction with R10-Iodide (R10-I)

Pretreat 1 mmol of Fmoc-$AA^3$-$AA^2$-$AA^1$-resin according to program, shake 1 mmol of R10-I. 3 mmol of sodium bicarbonate for 3 h and then wash according to program.

Method 1Ba Introduction of the Phosphoric Acid Residue onto the OH Group of hTyr, for Example, in the Side Chain R8*

Wash 1 mmol of R10-$AA^3$-$AA^2$-$AA^1$-resin 2× with DCM, suspend in DCM, add 2 mmol of phosphoric acid bis(dimethylamide) chloride. 2 mmol of DMAP and 3 mmol of DBU or DIPEA and shake at RT for 4-6 h, and then wash according to program.

Method 1Bb Introduction of Fmoc-Tyr-(PO(OBzl)-OH)—OH

Pretreat 1 mmol of Fmoc-$AA^2$-$AA^1$-resin according to program, add 2 mmol of Fmoc-Tyr(PO(OBzl)-OH)—OH, 2 mmol of HATU, 2 mmol HOAt (0.5M solution in DMF) and 5 mmol of DIPEA and shake at RT for 3 h. Check the pH during the reaction and adjust to pH 8-9 by adding DIPEA. After the coupling is complete, washing steps according to program.

Method 2 Solid-Phase Synthesis of Thioamides

The synthesis is based on, for example, H. Takuta et al. *J. Org. Chem.* 1989, 54, 4812 and Majer et al. *Biochem & Biophys. Res. Commun.* 1988, 150, 1017.

The first coupling takes place by method 1Aa.

Conversion of the carboxamide to the thioamide takes place with Lawesson's reagent in the following way: stir 1 mmol of Fmoc-AA-resin and 24 mmol of Lawesson's reagent in 20 ml of dry tcluene at a bath temperature of 90-100° C. for 7 h, filter off the resin with suction and wash on the funnel 5× alternately with DCM and hot MeOH.

The subsequent coupling of the second and third amino acids takes place by methods 1Ab-g and 1B.

Method 3A Elimination of the Carboxamides from the Resin

The peptide-resin is dried in vacuo at max. 40° C. before the elimination. Typically, 10-15 ml of elimination solution are used per gram of peptide.

1 mmol of peptide-resin is for this purpose stirred in a mixture of 0.5 ml of water and 15 ml of TFA at a bath temperature of 40° C. for 2 h. The resin is filtered off with suction and washed with a little TFA, and the resulting TFA solution is concentrated under diaphragm pump vacuum.

The oily crude product is purified by preparative HPLC— see method 4.

Method 3B Elimination of the Thioamides from the Resin

The peptide-resin is dried in vacuo at max. 40° C. before the elimination. Normally 10-15 ml of cleavage solution are used per gram of peptide.

Addition of EDT as scavenger is necessary in the elimination of the thioamides.

1 mmol of peptide-resin is stirred in a mixture of 0.5 ml of water/0.5 ml of EDT/15 ml of TFA at a bath temperature of 40-50° C. for 2-3 h. The resin is filtered off with suction and washed with a little TFA, and the resulting TFA solution is concentrated under diaphragm pump vacuum. The crude product is purified by preparative HPLC—see method 4.

Method 3C Elimination of a Carboxamide from the Resin and Simultaneous Hydrolysis of the Phosphoric Acid bis(dimethylamide) Residue Analogous to Method 3A.

For complete hydrolysis, after a reaction time of 2 h a further 1 ml of water is added and stirring is continued at 40° C. for 60 min. The resin is then filtered off with suction and washed with a little TFA, and finally the TFA solution is concentrated under diaphragm pump vacuum. The crude product is purified by preparative HPLC—see method 4.

Method 3D Elimination of a Thioamide from the Resin and Simultaneous Hydrolysis of the Phosphoric Acid bis(dimethylamide) Residue Analogous to Method 3B.

For complete hydrolysis, after a reaction time of 2-3 h a further 1 ml of water is added and stirring is continued at 40° C. for 60 min. The resin is then filtered off with suction and washed with a little TFA, and finally the TFA solution is concentrated under diaphragm pump vacuum. The crude product is purified by preparative HPLC—see method 4.

Method 4 Purification of the Crude Products by Semipreparative HPLC

Analytical and semipreparative HPLC systems from Shimadzu; column 250-50, LiChrospher® 100, RP18 (12 μm) from Merck; flow rate 60 in ml/min.

Eluents: A=970 ml of water+30 ml of ACN+1 ml of TFA
B=300 ml of water+700 ml of ACN+1 ml of TFA
UV detector 220 nm.

All products are isolated by gradient elution.

The crude products are dissolved in eluent B (DMF added for products of low solubility) and purified in portions on the column (e.g. dissolve 500 mg of crude product in 15 ml of B and separate in one portion). The separation conditions in this case depend on the peptide sequence and nature and amount of the impurities and are established experimentally beforehand on the analytical column.

A typical gradient is: 60%-100% B in 30 minutes.

If the crude products are mixtures of diastereomers, they are separated by this method.

The isolated fractions are checked by analytical HPLC ACN and TFA are removed in a rotary evaporator, and the remaining aqueous concentrate is lyophilized.

Method 5 Liquid-Phase Synthesis of benzyl {(S)-1-[(R)-6,8-dichloro-3-((S)-2-methyl-1-thiocarbamoylbutylcarbamoyl)-2,3,4,9-tetrahydro-1H-carbazol-3-yl-carbamoyl]-2-methylbutyl}carbamate (7)

Method 5A Synthesis of tert-butyl {(5)-1-carbamoyl-2-methylbutyl}carbamate (Boc-Ile-$NH_2$)

10 mmol of (S)—H-Ile-$NH_2$ hydrochloride were mixed with 20 mmol of aqueous sodium carbonate solution. A solution of 11 mmol of $Boc_2O$ in dioxane was slowly added dropwise to the aqueous solution at RT, and the reaction mixture was stirred at RT for a further 60 min. The precipitated crude product was then filtered off with suction, suspended in water and adjusted to an acidic pH by dropwise addition of 20% strength hydrochloric acid. The crude product was again filtered off with suction, washed with water and dried over $P_4O_{10}$ in vacuo at 50° C.

Yield 85%, m p. 167° C. (lit. 166° C.)

Method 5B Synthesis of tert-butyl ((S)-2-methyl-1-thiocarbamoylbutyl)carbamate (Boc-Ile thioamide)

The synthesis was based on, for example, H. Takuta et al. *J. Org. Chem.* 1989, 54, 4812 and Majer et al. *Biochem & Biophys. Res. Commun.* 1988, 150, 1017.

10 mmol of (S)-Boc-Ile-NH2 were suspended in 50 ml of THF, 6 mmol of Lawesson's reagent were added, and the mixture was stirred at RT for 20 h. The suspension became a clear solution. The reaction solution was finally concentrated under diaphragm pump vacuum.

The crude product was purified by column chromatography (DCM+ethyl acetate=9:1)

Yield 88.9% m p. 131° C. (lit. 132° C.)

Method 5C Synthesis of (S)-2-amino-3-methylpentanamide (H-Ile thioamide)

10 mmol of (S)-Boc-Ile thioamide were stirred in 40 ml of DCM and 10 ml of TFA at RT for 4 h. The reaction solution was finally concentrated under diaphragm pump vacuum, and the resulting residue was mixed with 50 ml of water, adjusted to pH 8 with conc. ammonia solution and finally extracted 5× with ethyl acetate. The combined organic extracts were washed with saturated sodium chloride solution, dried over sodium sulfate and filtered, and the filtrate was concentrated under diaphragm pump vacuum.

Yield 87.5% (yellow solid)

Method 5D Synthesis of (R/S)-3-(S)-2-benzyloxycarbonylamino-3-methylpentanoylamino)-6,8-dichloro-2,3,4,9-tetrahydro-1H-carbazole-3-carboxylic acid (Z-(S)-Ile-(R/S)-(6,8-Cl)-Thc-OH)

10 mmol of (R/S)—H-(6,8-Cl)-Thc. 12 mmol of (S)-Z-Ile-OSu, 30 mmol of DIPEA and a spatula tip of DMAP were put into 50 ml of DMF and stirred at a bath temperature of 80° C. for 4 h. The reaction mixture was then concentrated under diaphragm pump vacuum, and the residue was mixed with water, acidified with dilute hydrochloric acid and extracted with ethyl acetate. The organic phase was then washed with saturated sodium chloride solution, dried over sodium sulfate and filtered, and the filtrate was concentrated under diaphragm pump vacuum.

Yield 119 g of diastereomer mixture (1:1 mixture)

Method 5E Synthesis of benzyl {(S)-1-[(R)-6,8-dichloro-3-((S)-2-methyl-1-thiocarbamoyl-butylcarbamoyl)-2,3,4,9-tetrahydro-1H-carbazol-3-ylcarbamoyl]-2-methylbutyl}carbamate (7) ((S)-Z-Ile-(R)-(6,8-Cl)-Thc-(S)-Ile thioamide)

3 mmol of Z-Ile-(R/S)-(6,8-Cl)-Thc-OH, 3 mmol of H—(S)-Ile thioamide, 3 mmol of HATU and 15 mmol of DIPEA were heated in 5 ml of DMF in a microwave at max. 100° C. and max. 150 watt for 3 min. The reaction solution was diluted with eluent B and separated in 2 portions on a preparative HPLC column (see method 4).

Yield of diastereomer 1=19% of HPLC purity 98.5% (compound 7)

Yield of diastereomer 2=17.7% of HPLC purity 95%

Method 6 Exemplary Synthesis of C-Terminal Substituted Amides in Solution—(S)-2-{[(R/S)-3-((S)-2-benzyloxycarbonylamino-3-methylpentanoylamino)-6,8-dichloro-2,3,4, 9-tetrahydro-1H-carbazole-3-carbonyl]amino}-3-methylpentanoic acid ((S)-Z-Ile-(R/S)-(6,8-Cl)-Thc-(S)-Ile-OH)+R1-NH—R2

1 mmol of (S)-Z-Ile-(R/S)-(6,8-Cl)-Thc-(S)-Ile-OH (*) are suspended in 5 ml of DMF, and 1.1 mmol of R1-NH—R2, 1.2 mmol of PyBOP and 3 mmol of NMM are added, and the mixture is stirred at RT for 16 h. The reaction mixture is concentrated under diaphragm pump vacuum and purified by preparative HPLC (see method 4). The product obtained here is (S)-Z-Ile-(R/S)-(6,8-Cl)-Thc-(S)-Ile-NR1R2.

(*) The synthesis of (S)-Z-Ile-(R/S)-(6,8-Cl)-Thc-(S)-Ile-OH can be carried out on a solid phase with 2-chlorotrityl chloride-resin (1.37 mmol/g—Alexis Biochemicals 120-002-0000). The first coupling is carried out in DCM in the presence of DIPEA, and the second and third couplings in analogy to methods 1Ab+1Ac–1Ag. Elimination takes place as in method 3A, and purification as in method 4.

Method 7 Reaction of Lawesson's Reagent with R10-AA$^3$-AA$^2$-AA$^1$-NH$_2$ Alternative Method for Thiation of Sequences with C-Terminal Amide Function when AA$^2$ is a Thc-Building Block 1 mmol of R10-AA$^3$-AA$^2$-AA$^1$-NH$_2$ are dissolved in 40 ml of dry toluene, 1 mmol of Lawesson's reagent is added at RT, the suspension is stirred at a bath temperature of 80° C. for 3-4 h, and the reaction mixture is concentrated under diaphragm pump vacuum. The residue is fractionated by preparative HPLC in analogy to method 4.

Method 8 Preparation of Alkyl Aryl Ethers by Mitsunobu Reaction

Alkyl aryl ethers are prepared from corresponding OH compounds with addition of PPh$_3$ and DEAD (Mitsunobu et al., *J. Am. Chem. Soc.* 1972, 94, 679).

The general mode of preparation of the inventions of the invention is summarized once again below, indicating the appropriate process steps and methods:

a) firstly the Fmoc-protected AA$^1$ is coupled by method 1Aa to the resin

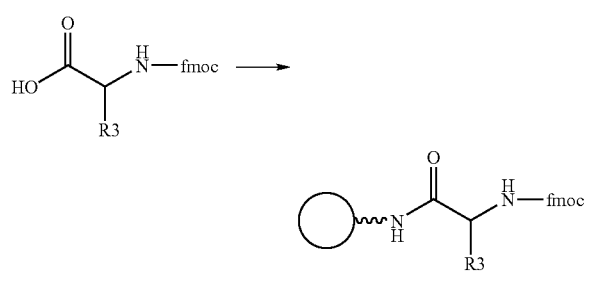

b) where appropriate conversion into a thioamide takes place in a second step by method 2

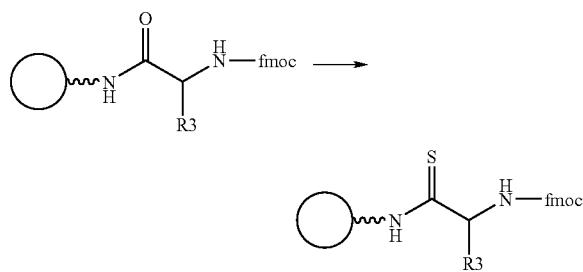

c) The product obtained from step a or b is, after elimination of the protective group, reacted with the protected amino acid 2, the appropriately substituted Thc derivative, by method 1Ab:

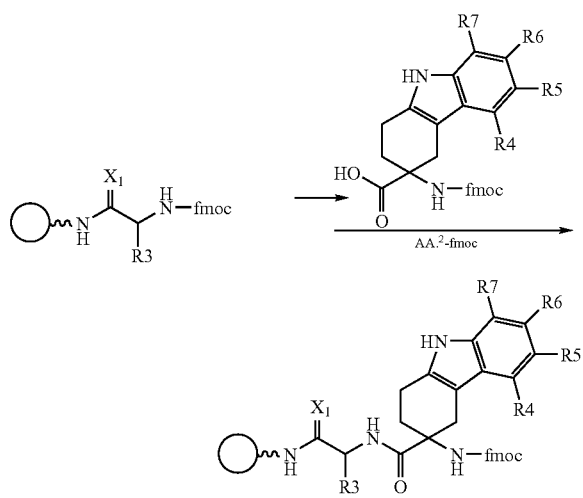

d) Then the product obtained from step c is, after elimination of the protective group, reacted with the third protected AA:

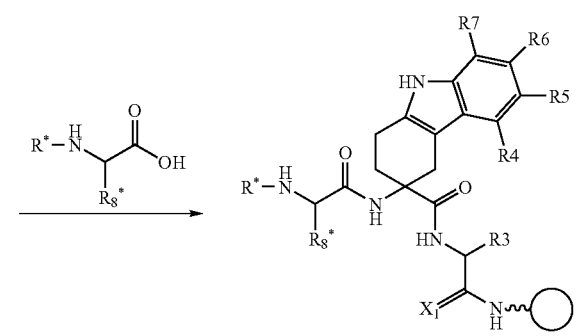

where R*=Z=—CO—O-benzyl (in method 1Ac) or R*=Fmoc (in method 1Ad), and R8* is —C$_1$-C$_6$-alkyl-aryl or —C$_1$-C$_6$-alkyl-heteroaryl, where the aryl or heteroaryl group is substituted by up to three, preferably by one OH group, or R8* may also—in accordance with the definitions given for R8— have the meaning of R3.

e) Where R*=Fmoc, the product obtained in step d is initially deprotected and the terminal free amino group is then reacted so as to introduce the radical R10:

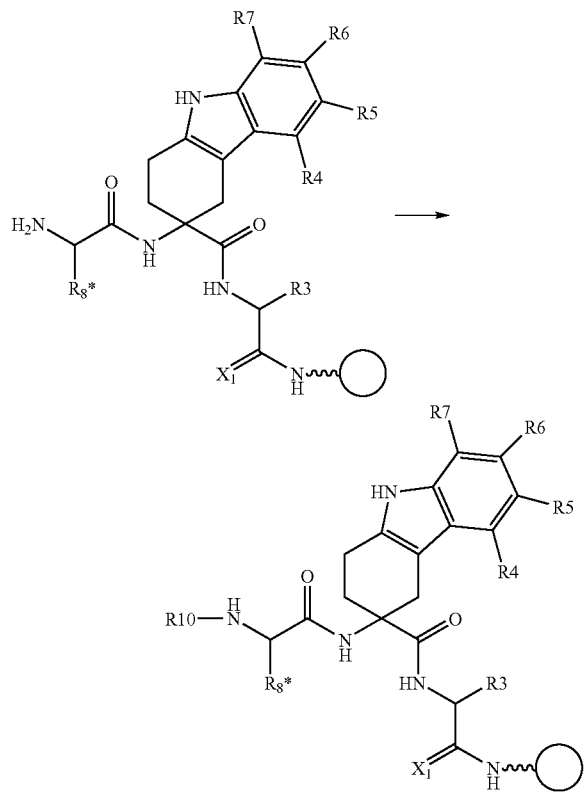

Depending on the nature of R10, different processes are used:
- (i) method 1Af for R10=-CO—R11; reaction with R11-COOH
- (ii) method 1Ag for R10=-CO—OR11; reaction with R11-OSu; in this case it is likewise possible, if R8* has a free OH group, for this OH group to be converted into —O—CO—O—R13, in which case R11 and R13 are identical radicals
- (iii) method 1Ah for R10=—R11; reaction with R10-iodide (R10-I)

f) In the optional step f it is possible where appropriate also to convert R8* into R8, e.g. by
- (i) introducing a phosphoric acid radical into R8 by converting an OH group as in step method 1Ba; or
- (ii) introducing a —CO—O-benzyl radical (Z) into R8 by converting an OH group as in step method 1Ae;

g) The tripeptide is then eliminated from the resin by one of methods 3A, 3B, 3C or 3D, and is purified by method 4.

h) If further modifications of R8 or R11 are also necessary, these can take place now, e.g. introduction of alkyl ethers from the corresponding OH compounds as in step method 8.

The compounds of the invention mentioned in Examples 1 to 15 and 16 to 77 were prepared as indicated in detail below by methods 1-8 as defined above. The analytical characterization of the compounds of the invention took place by $^1$H-NMR spectroscopy and/or mass spectrometry.

The chemicals and solvents employed were obtained commercially from usual suppliers (Acros, Avocado, Aldrich, Bachem, Fluka, Lancaster, Maybridge, Merck, Sigma, TCI etc.) or synthesized by processes known to the skilled worker For the exemplary embodiments indicated below, chiral building blocks were usually employed in enantiopure form. In the case of the tetrahydrocarbazole precursor, the racemic building block was employed. Final products were purified by semipreparative HPLC and characterized in the form of the pure diastereomers.

The compounds of the invention of the general formulae (I, Ia and Ib), especially compounds 1 to 77, were named using the AutoNom 2000 software (ISIS™/Draw 2.5; MDL).

The invention is to be explained in detail by means of the following examples without, however, being restricted to these examples.

LIST OF ABBREVIATIONS USED

| | |
|---|---|
| e g. | for example |
| DBU | 1,8-diazabicyclo[5.4.0]undec-7-ene |
| HOBt | 1-hydroxybenzotriazole |
| Fmoc | 9-fluoroenylmethoxycarbonyl |
| Boc | tert-butyloxycarbonyl |
| Z | benzyloxycarbonyl |
| Z-Cl | benzyloxycarbonyl chloride |
| Boc; O | di-tert-butyl dicarbonate |
| Bzl | benzyl |
| AA | amino acid |
| EDT | 1,2-ethanedithiol |
| DEAD | diethyl azodicarboxylate |
| DIC | N,N'-diisopropylcarbodiimide |
| DCC | N,N'-dicyclohexylcarbodiimide |
| HATU | N,N,N',N'-tetramethyl-O-(7-azabenzotriazol-1-yl)uronium hexafluorophosphate |
| HOAt | 1-hydroxy-7-azabenzotriazole |
| PyBop | (benzotriazol-1-yloxy)tripyrrolidinophosphonium hexafluorophosphate |
| OSu | N-hydroxysuccinimidyl |
| DIPEA | diisopropylethylamine |
| DMAP | N,N'-dimethylaminopyridine |
| DBU | 1,8-diazabicyclo[5.4.0]undec-7-ene |
| NMM | N-methylmorpholine |
| TFA | trifluoroacetic acid |
| DCM | dichloromethane |
| DMF | N,N'-dimethylformamide |
| DMA | N,N'-dimetylacetamide |
| ACN | acetonitrile |
| THF | tetrahydrofuran |
| Me | methyl |
| MeOH | methanol |
| Lawesson's reagent | 2,4-bis(4-methoxyphenyl)-1,3-dithia-2,4-diphosphetane 2,4-disulfide |
| Thc | 3-amino-2,3,4,9-tetrahydro-1H-carbazole-3-carboxylic acid |
| Ala | alanine(yl) |
| Val | valine(yl) |
| Ile | isoleucine(yl) |
| Leu | leucine(yl) |
| Gln | glutamine(yl) |
| Asn | asparagine(yl) |
| Tyr | tyrosine(yl) |
| hTyr | homo-tyrosine(yl) |
| Arg | arginine(yl) |
| Lys | lysine(yl) |
| RT | room temperature |
| m.p. | melting point |
| ml | milliliter |
| min | minute |
| h | hour |
| ELISA | enzyme linked immunosorbent assay |
| HEPES | N-(2-hydroxyethyl)piperazine-N'-2-ethanesulfonic acid |
| DMEM | Dulbecco's modified Eagles medium |
| RIA | radio immuno assay |
| LHRH | luteinizing hormone releasing hormone |
| LH | luteinizing hormone |
| NK1 | neurokinin 1 |
| NK2 | neurokinin 2 |

EXAMPLES

I. Synthesis of Compounds of the Invention

Example 1

4-Chlorobenzyl {(S)-1-[(R)-3-((S)-1-carbamoyl-2-methylpropylcarbamoyl)-6,8-dichloro-2,3,4,9-tetrahydro-1H-carbazol-3-ylcarbamoyl]-2-methylpropyl}carbamate (1)

0.275 g of 1 was obtained starting from 3 mmol of resin, Fmoc-Val-OH (AA$^1$ and AA$^3$), Fmoc-(6,8-dichloro)-Thc-OH (AA$^2$) and 4-chlorobenzyl 2,5-dioxopyrrolidin-1-yl carbonate by general methods 1Aa, b, d, g, 3A and 4.

Yield: 0.275 g (14.44% of theory)

$^1$H-NMR (DMSO-d6, 300K. 500 MHz):

δ=11.33 (s, 1H); 7.40-7.02 (m, 10H); 4.94 (d, 1H); 4.75 (d, 1H); 4.15 (dd, 1H); 3.87 (dd, 1H); 3.02 (d, 1H); 2.87 (d, 1H); 2.82-2.68 (m, 2H); 2.12 (m, 1H); 1.95 (m, 1H); 1.87 (m, 1H), 0.88-0.72 (m, 12H) ppm ESI-MS: found: 664.1 (M+H$^+$)/calculated: 663 g/mol

Example 2

4-Chlorobenzyl {(S)-1-[(R)-3-((S)-1-carbamoyl-2-methylpropylcarbamoyl)-6,8-dichloro-2,3,4,9-tetrahydro-1H-carbazol-3-ylcarbamoyl]-2-methylbutyl}carbamate (2)

0.190 g of 2 was obtained starting from 2.5 mmol of resin, Fmoc-Val-OH (AA$^1$), Fmoc-Ile-OH (AA$^3$), Fmoc-(6,8-dichloro)-Thc-OH (MA) and 4-chlorobenzyl 2,5-dioxopyrrolidin-1-yl carbonate by general methods 1Aa, b, d, g, 3A and 4.

Yield: 0.190 g (10.64% of theory)

$^1$H-NMR (DMSO-d6, 300K, 500 MHz):

δ=11.33 (s, 1H); 7.38-7.03 (m, 9H); 4.94 (d, 1H); 4.7 (d, 1H); 4.15 (dd, 1H); 3.87 (dd, 1H); 2.98 (d, 1H); 2.88 (d, 1H); 2.78-2.55 (m, 3H), 2.1 (m, 1H); 1.95 (m, 1H); 1.62 (m, 1H), 1.33 (m, 1H); 1.03 (m, 1H); 0.75 (m, 12H) ppm ESI-MS: found: 678.2 (M+H$^+$)/calculated: 677 g/mol

Example 3

4-Chlorobenzyl {(S)-1-[(R)-3-((S) carbamoyl-2-methylbutylcarbamoyl)-6,8-dichloro-2,3,4,9-tetrahydro-1H-carbazol-3-ylcarbamoyl]-2-methylbutyl}carbamate (3)

0.155 g of 3 was obtained starting from 2.5 mmol of resin, Fmoc-Ile-OH (AA$^1$ and AA$^3$), Fmoc-(6,8-dichloro)-Thc-OH (AA$^2$) and 4-chlorobenzyl 2,5-dioxopyrrolidin-1-yl carbonate by general methods 1Aa, b, d, g, 3A and 4.

Yield: 0.155 g (8.85% of theory)

$^1$H-NMR (DMSO-d6, 300K, 500 MHz):

δ=11.35 (s, 1H, indole NH); 7.4-7.03 (3m, 4H, 3H, 3H); 4.96, 4.7 (2d, 2H, C$_5$H$_6$—CH$_2$); 4.18 (dd, 1H); 3.89 (dd, 1H); 2.98, 2.88 (2d, 2H, CH$_2$); 2.77, 2.71, 2.62, 2.12 (4m, 4H, CH$_2$—CH$_2$); 1.82 (m, 1H); 1.64 (m, 1H); 1.45-1.3 (m, 2H); 1.05 (m, 2H), 0.84 (d, 3H, CH3); 0.82 (d, 3H, CH$_3$); 0.79 (t, 3H, CH$_3$); 0.73 (t, 3H, CH$_3$) ppm ESI-MS: found: 692.2 (M+H$^+$)/calculated: 691 g/mol

Example 4

(R)-6,8-Dichloro-3-{(S)-2-[2-(2-fluorophenyl)acetylamino]-3-methylpentanoylamino}-2,3,4,9-tetrahydro-1H-carbazole-3-carboxylic acid ((S)-1-carbonyl-2-methylbutyl)amide (4)

0.995 g of 4 was obtained starting from 7.0 mmol of resin, Fmoc-Ile-OH (AA$^1$ and AA$^3$), Fmoc-(6,8-dichloro)-Thc-OH (AA$^2$) and 2-fluorophenylacetic acid by general methods 1Aa, b, d, f, 3A and 4.

Yield: 0.995 g (19.64% of theory)

$^1$H-NMR (DMSO-d6, 300K, 600 MHZ):

δ=11.35 (s, 1H, indole NH); 8.12 (s, 1H); 7.82 (d, 1H); 7.40 (s, 1H); 7.29-7.23 (m, 2H); 7.20-7.13 (m, 3H); 7.12-7.06 (m, 3H); 4.12 (m, 2H); 3.47, 3.21 (2d, 2H, CH2); 2.99, 2.94 (2d, 2H, CH2); 2.79, 2.68 (2m, 2H, CH2); 2.59 (m, 1H); 2.12 (m, 1H); 1.62 (m, 2H); 1.33 (m, 2H); 1.01 (m, 2H); 0.80-0.71 (4m, 12H, 4 CH3) ppm ESI-MS: found: 660.3 (M+H$^+$)/calculated: 659.251 g/mol

Example 5

(R)-6,8-Dichloro-3-{(S)-2-[2-(3-fluorophenyl)acetylamino]-3-methylpentanoylamino}-2,3,4,9-tetrahydro-1H-carbazole-3-carboxylic acid ((S)-1-carbamoyl-2-methylbutyl)amide (5)

0.185 g of 5 was obtained starting from 3.0 mmol of resin, Fmoc-Ile-OH (AA$^1$ and AA$^3$), Fmoc-(6,8-dichloro)-Thc-OH (AA$^2$) and 3-fluorophenylacetic acid by general methods 1Aa, b, d, f, 3A and 4.

Yield: 0.185 g (11% of theory)

$^1$H-NMR (DMSO-d6, 300K, 500 MHz):

δ=11.2 (s, 1H, indole NH); 8.17 (d, 1H, NH); 8.07 (s, 1H, NH); 7.36 (s, 1H); 7.35-7.22 (m, 2H); 7.12-7.0 (m, 6H); 4.12-4.07 (m, 2H); 3.55, 3.45 (2d, 2H, C$_6$H$_5$F—CH$_2$); 3.4, 3.0 (2d, 2H, CH$_2$, Thc); 2.85 (m, 1H); 2.75-2.68 (m, 1H); 2.35-2.28 (m, 1H); 2.1-2.0 (m, 1H); 1.65 (m, 1H); 1.45 (m, 1H); 1.32 (m, 1H); 1.15-1.0 (m, 2H); 0.82-0.7 (m, 7H); 0.5-0.4 (d, t, 6H, CH$_3$) ppm.

ESI-MS: found: 660.3 (M+H$^+$)/calculated 659 g/mol

Example 6

2-Chlorobenzyl {(S)-1-[(R)-3-((S) carbamoyl-2-methylbutylcarbamoyl)-6,8-dichloro-2,3,4,9-tetrahydro-1H-carbazol-3-ylcarbamoyl]-2-methylbutyl}carbamate (6)

0.255 g of 6 was obtained starting from 3.0 mmol of resin, Fmoc-Ile-OH (AA$^1$ and AA$^3$), Fmoc-(6,8-dichloro)-Thc-OH (AAM) and 2-chlorobenzyl 2,5-dioxopyrrolidin-1-yl carbonate by general methods 1Aa, b, d, g, 3A and 4

Yield: 0.255 g (14.72% of theory)

$^1$H-NMR (DMSO-d6, 300K, 500 MHz):

δ=11.35 (s, 1H, indole NH); 7.75 (s, 1H, NH); 7.4 (d, 1H, NH); 7.35-7.2 (m, 6H); 7.1-7.05 (m, 2H); 5.05, 4.82 (2d, 2H, C$_5$H$_6$—CH$_2$); 4.18 (dd, 1H); 3.9 (dd, 1H); 2.98, 2.88 (2d, 2H, CH$_2$); 2.8, 2.72, 2.62, 2.12 (4m, 4H, CH$_2$—CH$_2$); 1.75 (m, 1H); 1.62 (m, 1H); 1.45-1.25 (m, 2H); 1.05 (m, 2H); 0.68 (m, 12H, CH$_3$) ppm.

ESI-MS: found: 692.2 (M+H$^+$)/calculated: 691 g/mol

Example 7

Benzyl {(S)-1-[(R)-6,8-dichloro-3-((S)-2-methyl-1-thiocarbamoylbutylcarbamoyl)-2,3,4,9-tetrahydro-1H-carbazol-3-ylcarbamoyl]-2-methylbutyl}carbamate (7)

0.126 g of 7 was obtained starting from 5.0 mmol of resin, Fmoc-Ile-OH (AA$^1$). Z-Ile-OH (AA$^3$) and Fmoc-(6,8-dichloro)-Thc-OH (AA$^2$) and by general methods 1Aa, 2, 1Ab, c, 3B and 4.

Yield: 0.126 g (3.38% of theory)

$^1$H-NMR (DMSO-d6, 300K, 600 MHz):

δ=11.38 (s, 1H, indole NH); 9.71, 9.32 (2s, 2H, CS—NH$_2$); 7.73 (s, 1H); 7.36 (s, 1H); 7.30-7.11 (3m, 8H); 4.96, 4.69 (2d, 2H, C$_5$H$_6$—CH$_2$); 4.46 (dd, 1H); 3.89 (dd, 1H); 2.98, 2.88 (2d, 2H, CH$_2$); 2.77, 2.71, 2.62, 2.12 (4m, 4H, CH$_2$—CH$_2$); 1.77 (m, 1H); 1.64 (m, 1H); 1.50 (m, 1H); 1.34 (m, 1H); 1.04 (m, 2H); 0.84 (d, 3H, CH$_2$); 0.82 (d, 3H, CH$_3$); 0.79 (t, 3H, CH$_3$); 0.73 (t, 3H, CH$_3$) ppm ESI-MS: found: 674.2 (M+H$^+$)/calculated: 673 g/mol As explained above, compound 7 was also synthesized in liquid phase by method 5 (A-E).

Example 8

Benzyl 4-{(S)-3-benzyloxycarbonylamino-3-[(R)-3-((S)-1-carbamoyl-2-methylbutylcarbamoyl)-6,8-dichloro-2,3,4,9-tetrahydro-1H-carbazol-3-ylcarbamoyl]propyl}phenyl carbonate (8)

0.125 g of 8 was obtained starting from 3.5 mmol of resin, Fmoc-Ile-OH (AA$^1$), Fmoc-hTyr-OH (AA$^3$), Fmoc-(6,8-dichloro)-Thc-OH (AA$^2$) and benzyl chlorocarbonate by general methods 1Aa, b, d, e, 3A and 4.

Yield: 0.125 g (3.92% of theory)

$^1$H-NMR (DMSO-d6, 300K, 600 MHz):

δ=11.41 (s, 1H, indole NH); 7.77 (s, 1H, NH); 7.54 (d, 1H); 7.48-7.29 (m, 10H); 7.22-7.05 (3m, 9H); 5.25 (s, 2H, OCOOCH$_2$—C$_6$H$_5$); 4.96, 4.68 (2d, 2H, C$_6$H$_5$—CH$_2$—OCON); 4.18 (dd, 1H); 3.92 (dt, 1H); 3.00, 2.92 (2d, 2H, CH$_2$); 2.74 (m, 2H); 2.60 (m, 2H); 2.46 (m, 1H); 2.08 (m, 1H); 1.79-170 (m, 3H); 1.37 (m, 1H); 1.01 (m, 1H); 0.83 (d, 3H, CH—CH$_3$); 0.73 (t, 3H, CH$_2$—CH$_3$) ppm ESI-MS: found: 856.1 (M+H$^+$)/calculated: 855 g/mol

Example 9

Benzyl[(S)-1-[(R)-3-((S)-1-carbamoyl-2-methylbutylcarbamoyl)-6,8-dichloro-2,3,4,9-tetrahydro-1H-carbazol-3-ylcarbamoyl]-2-(4-phosphonooxyphenyl)ethyl]carbamate (9)

0.112 g of 9 was obtained starting from 1.3 mmol of resin, Fmoc-Ile-OH (AA$^1$). Z-Tyr-OH (AA$^3$) and Fmoc-(6,8-dichloro)-Thc-OH (AA$^2$) by general methods 1Aa, b, c, 1Ba, 3C and 4

Yield: 0.112 g (9.98% of theory)

$^1$H-NMR (DMSO-d6, 300K. 600 MHz):

δ=11.39 (s, 1H, indole NH); 7.98 (s, 1H); 7.45 (d, 1H); 7.42 (s, 1H); 7.37 (s, 1H); 7.32-7.28 (m, 3H); 7.17-7.12 (m, 6H); 7.10 (m, 1H); 7.02 (d, 2H); 4.90, 4.73 (2d, 2H, C$_6$H$_5$—CH$_2$); 4.26 (m, 1H); 4.19 (m, 1H); 2.94 (m, 2H); 2.83 (m, 1H); 2.73 (m, 1H); 2.63 (m, 2H); 2.20 (m, 1H); 2.06 (m, 1H); 1.73 (m, 1H); 1.41 (m, 1H); 1.05 (m, 1H); 0.84 (d, 3H, CH—CH$_3$); 0.79 (t, 3H, CH$_2$—CH$_3$) ppm ESI-MS: found: 788.2 (M+H$^+$)/calculated: 787 g/mol

Example 10

Benzyl[(S)-1-[(R)-6,8-dichloro-3-((S)-2-methyl-1-thiocarbamoylbutylcarbamoyl)-2,3,4,9-tetrahydro-1H-carbazol-3-ylcarbamoyl]-3-(4-hydroxyphenyl)propyl]carbamate (10)

0.45 g of 10 was obtained starting from 4 4 mmol of resin, Fmoc-Ile-OH (AA$^1$), Fmoc-hTyr-OH (AA$^3$), Fmoc-(6,8-dichloro)-Thc-OH (AA$^2$) and benzyl chlorocarbonate by general methods 1Aa, 2, 1Ab, d, e, 3B and 4

Yield 0.45 g (19.47% of theory)

$^1$H-NMR (DMSO-d6, 300K, 600 MHz):

δ=11.41 (s, 1H, indole NH), 9.71 (s, 1H, CS—NH—CH); 9.28, 9.12 (2s, CS—NH$_2$); 7.67 (s, 1H); 7.41 (d, 2H); 7.37 (s, 1H), 7.32-7.28 (m, 4H); 7.17-7.15 (m, 3H); 6.83 (d, 2H); 6.61 (d, 2H); 4.96, 4.65 (2d, 2H, C$_6$H$_5$—CH$_2$); 4.44 (dd, 1H); 3.89 (dd, 1H), 3.02, 2.88 (2d, 2H, CH$_2$); 2.76 (m, 2H); 2.62 (m, 1H); 2.46 (m, 1H); 2.35 (m, 1H); 2.09 (m, 1H); 1.79-1.74 (m, 3H): 1.48 (m, 1H); 1.02 (m, 1H); 0.83 (d, 3H, CH—CH$_3$); 0.74 (1, 3H, CH$_2$—CH$_3$) ppm ESI-MS: found 738.1 (M+H$^+$)/calculated: 737 g/mol

Example 11

Benzyl[(S)-1-[(R)-3-((S)-carbamoyl-2-methylbutylcarbamoyl)-6,8-dichloro-2,3,4,9-tetrahydro-1H-carbazol-3-ylcarbamoyl]-3-(4-phosphonooxyphenyl)propyl]carbamate (11)

1.511 g of 11 were obtained starting from 10.0 mmol of resin, Fmoc-Ile-OH (AA$^1$), Z-hTyr-OH (AA$^3$) and Fmoc-(6,8-dichloro)-Thc-OH (AA$^2$) by general methods 1Aa, b, c, 1 Ba, 3C and 4.

Yield: 1.511 g (18.37% of theory)

$^1$H-NMR (DMSO-d6, 300K, 600 MHz):

δ=11.39 (s, 1H, indole NH); 7.75 (s, 1H); 7.49 (d, 1H); 7.42 (s, 1H); 7.35-7.30 (m, 4H); 7.21-7.16 (m, 3H); 7.14 (d, 1H); 7.11 (s, 1H); 7.02 (m, 4H); 4.96, 4.69 (2d, 2H, C$_6$H$_5$—CH$_2$); 4.18 (dd, 1H); 3.92 (dt, 1H); 3.00, 2.94 (2d, 2H, CH$_2$); 2.75 (m, 2H); 2.56 (m, 1H); 2.43 (m, 2H); 2.09 (m, 1H); 1.75 (m, 3H); 1.38 (m, 1H); 1.05 (m, 1H); 0.83 (d, 3H, CH—CH$_3$); 0.75 (t, 3H, CH$_2$—CH$_3$) ppm ESI-MS: found: 802.0 (M+H$^+$)/calculated: 801 g/mol

Example 12

Benzyl[(S)-1-[(R)-6,8-dichloro-3-((S)-2-methyl-1-thiocarbamoylbutylcarbamoyl)-2,3,4,9-tetrahydro-1H-carbazol-3-ylcarbamoyl]-3-(4-phosphonooxyphenyl)propyl]carbamate (12)

0.079 g of 12 was obtained starting from 10.0 mmol of resin, Fmoc-Ile-OH (AA$^1$), Fmoc-hTyr-OH (AA$^3$), Fmoc-(6,8-dichloro)Thc-OH (AA$^2$) and benzyl chlorocarbonate by general methods 1Aa, 2, 1Ab, d, e, 1Ba, 3D and 4.

Yield: 0.079 g (0.96% of theory)

$^1$H-NMR (DMSO-d6, 300K, 600 MHz):

δ=11.41 (s, 1H, indole NH); 9.70, 9.29 (2s, 2H, CS—NH$_2$); 7.73 (s, 1H); 7.44 (d, 1H); 7.37 (s, 1H); 7.33-7.27 (m, 4H); 7.20-7.14 (m, 3H); 7.07-7.03 (m, 4H); 4.96, 4.66 (2d, 2H, C$_6$H$_5$—CH$_2$); 4.44 (dd, 1H); 392 (dt, 1H); 301, 2.91 (2d, 2H, CH₂), 2.74 (m, 2H); 2.59 (m, 2H); 2.44 (m, 2H); 2.09 (m, H), 1.79 (m, 2H); 1.48 (m, 1H); 1.03 (m, 1H); 0.83 (d, 3H, CH—CH₃); 0.75 (t, 3H, CH₃) ppm
ESI-MS: found: 818.1 (M+H⁺)/calculated: 817 g/mol Example 13

(R)-6,8-Dichloro-3-{(S)-2-[2-(2-fluorophenyl)acetylamino]-3-methylpentanoylamino}-2,3,4,9-tetrahydro-1H-carbazole-3-carboxylic acid ((S)-2-methyl-1-thiocarbamoylbutyl)amide (13)

0.437 g of 13 was obtained starting from 4.00 mmol of resin, Fmoc-Ile-OH (AA¹ and AA³), Fmoc-(6,8-dichloro)-Thc-OH (AA²) and 2-fluorophenylacetic acid by general methods 1Aa, 2, 1Ab, d, f, 3B and 4.
Yield: 0.437 g (15.61% of theory)
¹H-NMR (DMSO-d6, 300K, 600 MHz):
δ=11.37 (s, 1H, indole NH); 9.69, 9.21 (2s, 2H, CS—NH₂); 8.06 (d, 1H); 7.82 (s, 1H); 7.37 (s, 1H); 7.29-7.23 (m, 2H); 7.17 (m, 2H); 7.09 (m, 2H); 4.46 (dd, 1H); 4.15 (dt, 1H); 3.45, 3.18 (2d, 2H, CH₂); 2.97, 2.89 (2d, 2H, C₂); 2.77 (m, 1H); 2.68 (m, 1H); 2.56 (m, 1H), 2.12 (m, 1H); 1.71-1.59 (m, 2H); 1.44 (m, 1H); 1.35 (m, 1H); 1.02 (m, 2H); 0.81 (d, 3H, CH—CH₃); 0.78-0.75 (m, 6H, 2 CH₃), 0.73 (t, 3H, CH—CH₃) ppm
ESI-MS: found: 676.2 (M+H⁺)/calculated: 675 g/mol Example 14

(R)-6,8-Dichloro-3-[(S)-2-[2-(2-fluorophenyl)acetylamino]-4-(4-hydroxyphenyl)butyrylamino]-2,3,4,9-tetrahydro-1H-carbazole-3-carboxylic acid ((S)-2-methyl-1-thiocarbamoylbutyl)amide (14)

0.632 g of 14 was obtained starting from 4.5 mmol of resin, Fmoc-Ile-OH (AA¹). Fmoc-hTyr-OH (AA³), Fmoc-(6,8-dichloro)-Thc-OH (AA²) and 2-fluorophenylacetic acid by general methods 1Aa, 2, 1Ab, d, f, 3B and 4.
Yield: 0.632 g (17.61% of theory)
¹H-NMR (DMSO-d6, 300K, 600 MHz):
δ=11.37 (s, 1H, indole NH); 9.67, 9.14 (2s, 2H, CS—NH₂); 9.13 (br.s, 1H, OH); 8.29 (d, 1H); 7.84 (s, 1H); 7.38 (s, 1H); 7.31 (d, 1H); 7.26 (m, 1H); 7.21-7.08 (2m, 4H); 6.79 (d, 2H); 6.60 (d, 2H); 4.43 (dd, 1H); 4.13 (d, 1H); 3.45, 3.22 (2d, 2H, CH₂); 2.99, 2.96 (2d, 2H, CH₂); 2.76-2.72 (m, 2H); 2.58 (m, 1H); 2.42 (m, 1H); 2.33 (m, 1H); 2.09 (m, 1H); 1.75 (m, 2H); 1.65 (m, 1H); 1.42 (m, 1H); 0.99 (m, 1H); 0.79 (d, 3H, CH₂—CH₃); 0.73 (t, 3H, CH₂—CH₃) ppm
ESI-MS: found: 740.2 (M+H⁺)/calculated: 739 g/mol Example 15

Mono-(4-{(S)-3-[(R)-6,8-dichloro-3-((S)-2-methyl-1-thiocarbamoylbutylcarbamoyl)-2,3,4,9-tetrahydro-1H-carbazol-3-ylcarbamoyl]-3-[2-(2-fluorophenyl)acetylamino]-propyl}phenyl phosphate (15)

0.129 g of 15 was obtained starting from 3.3 mmol of resin, Fmoc-Ile-OH (AA¹), Fmoc-hTyr-OH (AA³), Fmoc-(6,8-dichloro)-Thc-OH (AA²) and 2-fluorophenylacetic acid by general methods 1Aa, 2, 1Ab, d, f, 1Ba, 3D and 4.
Yield: 0.129 g (4.6% of theory)
¹H-NMR (DMSO-d6, 300K, 600 MHz):
δ=11.38 (s, 1H, indole NH); 9.7, 9.15 (2s, 2H, CS—NH₂); 8.32 (d, 1H); 7.9 (s, 1H); 7.38 (s, 1H); 7.33-7.0 (m, 11H); 4.42 (dd, 1H); 4.17 (d, 1H); 3.47, 3.22 (2d, 2H, CH₂); 2.99, 2.96 (2d, 2H, CH₂); 2.77-2.67 (m, 2H); 2.6-2.35 (m, 2H); 2.1 (m, 1H); 1.8 (m, 2H); 1.65 (m, 1H); 1.43 (m, 1H); 0.99 (m, 1H); 0.79 (d, 3H, CH₂—CH₃); 0.73 (t, 3H, CH₂—CH₃) ppm.
ESI-MS: found: 820.0 (M+H⁺)/calculated: 819 g/mol Data on further exemplary embodiments are compiled in Table 2 below:

TABLE 2

Exemplary embodiments with synthetic sequence and MS data

| No. | AUTONOM name | Synthesis method | ESI-MS calculated | ESI-MS found (M + H⁺) |
|-----|--------------|------------------|-------------------|------------------------|
| 16 | (R)-6,8-Dichloro-3-{(S)-2-[3-(4-fluorophenyl)propionylamino]-3-methylpentanoylamino}-2,3,4,9-tetrahydro-1H-carbazole-3-carboxylic acid ((S)-1-carbamoyl-2-methylpropyl)amide | 1Aa, b, d, f, 3A, 4 | 659 | 660.3 |
| 17 | (S)-5-[(R)-3-((S)-1-Carbamoyl-2-methylpropylcarbamoyl)-6,8-dichloro-2,3,4,9-tetrahydro-1H-carbazol-3-ylcarbamoyl]-5-[3-(4-fluorophenyl)propionylamino]-pentylammonium trifluoroacetate | 1Aa, b, d, f, 3A, 4 | 674 | 675.3 |
| 18 | (S)-6,8-Dichloro-3-{(S)-2-[3-(2-hydroxyphenyl)propionylamino]-3-methylpentanoylamino}-2,3,4,9-tetrahydro-1H-carbazole-3-carboxylic acid ((S)-1-carbamoyl-2-methylbutyl)amide | 1Aa, b, d, f, 3A, 4 | 671 | 672.3 |
| 19 | Benzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-[4-(2-{2-[2-(2-methoxyethoxy)ethoxy]ethoxy}ethoxy)phenyl]-ethyl}carbamate | 1Aa, b, d, e, 3A, 4, 8, 4 | 897 | 898.3 |
| 20 | (R)-6,8-Dichloro-3-((S)-2-{3-[2-(2-{2-[2-(2-methoxyethoxy)ethoxy]ethoxy}ethoxy)-phenyl]propionylamino}-3-methylpentanoylamino)-2,3,4,9-tetrahydro-1H-carbazole-3-carboxylic acid ((S)-1-carbamoyl-2-methylbutyl)amide | 1Aa, b, d, f, 3A, 4, 8, 4 | 861 | 862.4 |

TABLE 2-continued

Exemplary embodiments with synthetic sequence and MS data

| No. | AUTONOM name | Synthesis method | ESI-MS calculated | ESI-MS found (M + H$^+$) |
|---|---|---|---|---|
| 21 | (R)-6,8-Dichloro-3-((S)-2-{2-[2-(2-{2-[2-(2-methoxyethoxy)ethoxy]ethoxy}ethoxy)-phenyl]acetylamino}-3-methylpentanoyl-amino)-2,3,4,9-tetrahydro-1H-carbazole-3-carboxylic acid ((S)-1-carbamoyl-2-methyl-butyl)amide | 1Aa, b, d, f, 3A, 4, 8, 4 | 847 | 848.4 |
| 22 | (R)-6,8-Dichloro-3-[(S)-2-[3-(2-fluoro-phenyl)propionylamino]-4-(4-hydroxy-phenyl)butyrylamino]-2,3,4,9-tetrahydro-1H-carbazole-3-carboxylic acid ((S)-1-carbamoyl-2-methylbutyl)amide | 1Aa, b, d, f, 3A, 4 | 737 | 738.3 |
| 23 | (R)-6,8-Dichloro-3-{(S)-2-[3-(2-fluoro-phenyl)propionylamino]-3-methyl-pentanoylamino}-2,3,4,9-tetrahydro-1H-carbazole-3-carboxylic acid ((S)-1-carbamoyl-2-methylbutyl)amide | 1Aa, b, d, f, 3A, 4 | 673 | 674.4 |
| 24 | Benzyl {(S)-1-[(R)-6,8-dichloro-3-((S)-2-methyl-1-thiocarbamoylbutylcarbamoyl)-2,3,4,9-tetrahydro-1H-carbazol-3-yl-carbamoyl]-3-[4-(2-{2-[2-(2-methoxy-ethoxy)ethoxy]ethoxy}ethoxy)phenyl]-propyl}carbamate | 1Aa, 2, 1Ab, d, g, 3B, 4, 8, 4 | 928 | 928.2 |
| 25 | Benzyl {(S)-1-[(R)-8-chloro-6-fluoro-3-((S)-2-methyl-1-thiocarbamoylbutylcarbamoyl)-2,3,4,9-tetrahydro-1H-carbazol-3-yl-carbamoyl]-2-methylbutyl}carbamate | 5 (A-E) | 657 | 658.3 |
| 26 | 3-Methylbenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate | 1Aa, b, d, g, 3A, 4 | 671 | 672.2 |
| 27 | 2,6-Difluorobenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate | 1Aa, b, d, g, 3A, 4 | 693 | 694.3 |
| 28 | 3,5-Difluorobenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate | 1Aa, b, d, g, 3A, 4 | 693 | 694.4 |
| 29 | 3,5-Dichlorobenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate | 1Aa, b, d, g, 3A, 4 | 725 | 726.2 |
| 30 | 3-Fluorobenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate | 1Aa, b, d, g, 3A, 4 | 675 | 676.4 |
| 31 | 2-Fluorobenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate | 1Aa, b, d, g, 3A, 4 | 675 | 676.4 |
| 32 | 3-Chlorobenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate | 1Aa, b, d, g, 3A, 4 | 691 | 694.3 |
| 33 | 3,5-Difluorobenzyl {(S)-1-[(R)-3-((S)-1-carbamoyl-2-methylbutylcarbamoyl)-8-chloro-6-fluoro-2,3,4,9-tetrahydro-1H-carbazol-3-ylcarbamoyl]-2-methylbutyl}carbamate | 1Aa, b, d, g, 3A, 4 | 677 | 678.3 |
| 34 | 3-Fluorobenzyl {(S)-1-[(R)-3-((S)-1-carbamoyl-2-methylbutylcarbamoyl)-8-chloro-6-fluoro-2,3,4,9-tetrahydro-1H-carbazol-3-ylcarbamoyl]-2-methyl-butyl}carbamate | 1Aa, b, d, g, 3A, 4 | 659 | 660.4 |
| 35 | 2-Fluorobenzyl {(S)-1-[(R)-3-((S)-1-carbamoyl-2-methylbutylcarbamoyl)-8-chloro-6-fluoro-2,3,4,9-tetrahydro-1H-carbazol-3-ylcarbamoyl]-2-methyl-butyl}carbamate | 1Aa, b, d, g, 3A, 4 | 659 | 660.4 |
| 36 | 4-[(S)-3-[(R)-3-((S)-1-Carbamoyl-2-methyl-butylcarbamoyl)-6,8-dichloro-2,3,4,9-tetra-hydro-1H-carbazol-3-ylcarbamoyl]-3-(2,6-difluorobenzyloxycarbonylamino)propyl]-phenyl 2,6-difluorobenzyl carbonate | 1Aa, b, d, g, 3A, 4 | 927 | 928.2 |

TABLE 2-continued

Exemplary embodiments with synthetic sequence and MS data

| No. | AUTONOM name | Synthesis method | ESI-MS calculated | ESI-MS found (M + H⁺) |
|---|---|---|---|---|
| 37 | 3-Fluorobenzyl [(S)-1-[(R)-3-((S)-1-carbamoyl-2-methylbutylcarbamoyl)-6,8-dichloro-2,3,4,9-tetrahydro-1H-carbazol-3-ylcarbamoyl]-3-(4-hydroxyphenyl)propyl]-carbamate | 1Aa, b, d, g, 3A, 4 | 739 | 740.4 |
| 38 | 2-Fluorobenzyl [(S)-1-[(R)-3-((S)-1-carbamoyl-2-methylbutylcarbamoyl)-6,8-dichloro-2,3,4,9-tetrahydro-1H-carbazol-3-ylcarbamoyl]-3-(4-hydroxyphenyl)propyl]-carbamate | 1Aa, b, d, g, 3A, 4 | 739 | 740.3 |
| 39 | 4-[(S)-3-[(R)-3-((S)-1-Carbamoyl-2-methyl-butylcarbamoyl)-6,8-dichloro-2,3,4,9-tetra-hydro-1H-carbazol-3-ylcarbamoyl]-3-(2-fluorobenzyloxycarbonylamino)propyl]-phenyl 2-fluorobenzyl carbonate | 1Aa, b, d, g, 3A, 4 | 891 | 892.4 |
| 40 | 2-(2-Fluorophenyl)ethyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl})carbamate | 1Aa, b, d, g, 3A, 4 | 689 | 690.3 |
| 41 | 2-Fluorobenzyl {(S)-1-[(R)-8-chloro-6-fluoro-3-((S)-2-methyl-1-thiocarbamoyl-butylcarbamoyl)-2,3,4,9-tetrahydro-1H-carbazol-3-ylcarbamoyl]-2-methylbutyl}-carbamate | 1Aa, 2, 1Ab, d, g, 3A, 4 | 675 | 676.4 |
| 42 | 3-Fluorobenzyl {(S)-1-[(R)-8-chloro-6-fluoro-3-((S)-2-methyl-1-thiocarbamoyl-butylcarbamoyl)-2,3,4,9-tetrahydro-1H-carbazol-3-ylcarbamoyl]-2-methylbutyl}-carbamate | 1Aa, 2, 1Ab, d, g, 3A, 4 | 675 | 676.4 |
| 43 | 2-Fluorobenzyl [(S)-1-[(R)-6,8-dichloro-3-((S)-2-methyl-1-thiocarbamoylbutyl-carbamoyl)-2,3,4,9-tetrahydro-1H-carbazol-3-ylcarbamoyl]-3-(4-hydroxy-phenyl)propyl]carbamate | 1Aa, 2, 1Ab, d, g, 3A, 4 | 755 | 756.4 |
| 44 | 4-[(S)-3-[(R)-6,8-Dichloro-3-((S)-2-methyl-1-thiocarbamoylbutylcarbamoyl)-2,3,4,9-tetrahydro-1H-carbazol-3-ylcarbamoyl]-3-(2-fluorobenzyloxycarbonylamino)-propyl]phenyl 2-fluorobenzyl carbonate | 1Aa, 2, 1Ab, d, g, 3A, 4 | 907 | 908.3 |
| 45 | 3-Fluorobenzyl [(S)-1-[(R)-6,8-dichloro-3-((S)-2-methyl-1-thiocarbamoylbutyl-carbamoyl)-2,3,4,9-tetrahydro-1H-carbazol-3-ylcarbamoyl]-3-(4-hydroxy-phenyl)propyl]carbamate | 1Aa, 2, 1Ab, d, g, 3A, 4 | 755 | 756.3 |
| 46 | 4-[(S)-3-[(R)-6,8-Dichloro-3-((S)-2-methyl-1-thiocarbamoylbutylcarbamoyl)-2,3,4,9-tetrahydro-1H-carbazol-3-ylcarbamoyl]-3-(3-fluorobenzyloxycarbonylamino)-propyl]phenyl 3-fluorobenzyl carbonate | 1Aa, 2, 1Ab, d, g, 3A, 4 | 907 | 908.4 |
| 47 | 3-Methoxybenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate | 1Aa, b, d, g, 3A, 4 | 687 | 688.3 |
| 48 | 4-Fluorobenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate | 1Aa, b, d, g, 3A, 4 | 675 | 676.4 |
| 49 | 2-Methylbenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate | 1Aa, b, d, g, 3A, 4 | 671 | 672.3 |
| 50 | 2,3-Dimethoxybenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate | 1Aa, b, d, g, 3A, 4 | 717 | 718.3 |
| 51 | 2-Methoxybenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate | 1Aa, b, d, g, 3A, 4 | 687 | 688.3 |
| 52 | (R)-6,8-Dichloro-3-{(S)-2-[2-(2-fluorophenyl)ethylamino]-3-methylpentanoylamino}-2,3,4,9-tetrahydro-1H-carbazole-3-carboxylic acid ((S)-1-carbamoyl-2-methylbutyl)amide | 1Aa, b, d, h, 3A, 4 | 645 | 646.3 |

TABLE 2-continued

Exemplary embodiments with synthetic sequence and MS data

| No. | AUTONOM name | Synthesis method | ESI-MS calculated | ESI-MS found (M + H⁺) |
|---|---|---|---|---|
| 53 | 2-Trifluoromethylbenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate | 1Aa, b, d, g, 3A, 4 | 725 | 726.4 |
| 54 | 3-Trifluoromethylbenzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methylbutyl}carbamate | 1Aa, b, d, g, 3A, 4 | 725 | 726.4 |
| 55 | 3-Trifluoromethoxybenzyl {(S)-1-[(R)-3-((S)-1-carbamoyl-2-methylbutyl-carbamoyl)-6,8-dichloro-2,3,4,9-tetra-hydro-1H-carbazol-3-ylcarbamoyl]-2-methylbutyl}carbamate | 1Aa, b, d, g, 3A, 4 | 741 | 742.3 |
| 56 | 2-Trifluoromethoxybenzyl {(S)-1-[(R)-3-((S)-1-carbamoyl-2-methylbutyl-carbamoyl)-6,8-dichloro-2,3,4,9-tetrahydro-1H-carbazol-3-ylcarbamoyl]-2-methylbutyl}carbamate | 1Aa, b, d, g, 3A, 4 | 741 | 742.3 |
| 57 | 4-Fluorobenzyl {(S)-1-[(R)-6,8-dichloro-3-((S)-2-methyl-1-thiocarbamoylbutyl-carbamoyl)-2,3,4,9-tetrahydro-1H-carbazol-3-ylcarbamoyl]-2-methylbutyl}-carbamate | 1Aa, 2, 1Ab, d, g, 3A, 4 | 691 | 692.3 |
| 58 | (R)-6,8-Dichloro-3-{(S)-2-[2-(4-fluoro-phenyl)ethylamino]-3-methylpentanoyl-amino}-2,3,4,9-tetrahydro-1H-carbazole-3-carboxylic acid ((S)-1-carbamoyl-2-methylbutyl)amide | 1Aa, b, d, h, 3A, 4 | 645 | 647.1 |
| 59 | (R)-6,8-Dichloro-3-{(S)-2-[2-(2,6-difluorophenyl)acetylamino]-3-methylpentanoylamino}-2,3,4,9-tetrahydro-1H-carbazole-3-carboxylic acid ((S)-1-carbamoyl-2-methylbutyl)amide | 1Aa, b, d, f, 3A, 4 | 677 | 678.5 |
| 60 | 4-Fluorobenzyl {(S)-1-[(R)-8-chloro-6-fluoro-3-((S)-2-methyl-1-thiocarbamoyl-butylcarbamoyl)-2,3,4,9-tetrahydro-1H-carbazol-3-ylcarbamoyl]-2-methylbutyl}-carbamate | 1Aa, 2, 1Ab, d, g, 3A, 4 | 675 | 676.4 |
| 61 | (R)-6,8-Dichloro-3-{(S)-2-[2-(3-fluorophenyl)ethylamino]-3-methylpentanoylamino}-2,3,4,9-tetrahydro-1H-carbazole-3-carboxylic acid ((S)-1-carbamoyl-2-methylbutyl)amide | 1Aa, b, d, h, 3A, 4 | 645 | 646.3 |
| 62 | (R)-8-Chloro-3-{(S)-2-[2-(2,6-difluoro-phenyl)acetylamino]-3-methylpentanoyl-amino}-6-fluoro-2,3,4,9-tetrahydro-1H-carbazole-3-carboxylic acid ((S)-2-methyl-1-thiocarbamoylbutyl)amide | 1Aa, 2, 1Ab, d, f, 3A, 4 | 677 | 678.4 |
| 63 | (R)-8-Chloro-6-fluoro-3-{(S)-2-[2-(4-fluorophenyl)ethylamino]-3-methyl-pentanoylamino}-2,3,4,9-tetrahydro-1H-carbazole-3-carboxylic acid ((S)-1-carbamoyl-2-methylbutyl)amide | 1Aa, b, d, h, 3A, 4 | 629 | 630.4 |
| 64 | 4-Fluorobenzyl {(S)-1-[(R)-3-((S)-1-carbamoyl-2-methylbutylcarbamoyl)-8-chloro-6-fluoro-2,3,4,9-tetrahydro-1H-carbazol-3-ylcarbamoyl]-2-methylbutyl}-carbamate | 1Aa, b, d, g, 3A, 4 | 659 | 660.3 |
| 65 | (R)-8-Chloro-6-fluoro-3-{(S)-2-[2-(4-fluorophenyl)acetylamino]-3-methylpentanoylamino}-2,3,4,9-tetrahydro-1H-carbazole-3-carboxylic acid ((S)-2-methyl-1-thiocarbamoylbutyl)amide | 1Aa, 2, 1Ab, d, f, 3A, 4 | 659 | 660.3 |
| 66 | (R)-8-Chloro-3-{(S)-2-[2-(2,4-difluoro-phenyl)acetylamino]-3-methylpentanoyl-amino}-6-fluoro-2,3,4,9-tetrahydro-1H-carbazole-3-carboxylic acid ((S)-2-methyl-1-thiocarbamoylbutyl)amide | 1Aa, 2, 1Ab, d, f, 3A, 4 | 677 | 678.2 |
| 67 | (R)-8-Chloro-6-fluoro-3-{(S)-2-[2-(4-fluorophenyl)ethylamino]-3-methyl-pentanoylamino}-2,3,4,9-tetrahydro-1H-carbazole-3-carboxylic acid ((S)-2-methyl-1-thiocarbamoylbutyl)amide | 1Aa, b, d, h, 2, 3A, 4 | 645 | 646.4 |

TABLE 2-continued

Exemplary embodiments with synthetic sequence and MS data

| No. | AUTONOM name | Synthesis method | ESI-MS calculated | ESI-MS found (M + H$^+$) |
|---|---|---|---|---|
| 68 | (R)-8-Chloro-6-fluoro-3-{(S)-2-[2-(2-fluorophenyl)acetylamino]-3-methyl-pentanoylamino}-2,3,4,9-tetrahydro-1H-carbazole-3-carboxylic acid ((S)-2-methyl-1-thiocarbamoylbutyl)amide | 1Aa, 2, 1Ab, d, f, 3A, 4 | 659 | 660.4 |
| 69 | (R)-8-Chloro-6-fluoro-3-{(S)-2-[2-(2-fluoro-phenyl)acetylamino]-3-methylpentanoyl-amino}-2,3,4,9-tetrahydro-1H-carbazole-3-carboxylic acid ((S)-1-carbamoyl-2-methyl-butyl)amide | 1Aa, b, d, f, 3A, 4 | 643 | 644.4 |
| 70 | (R)-3-{(S)-2-[2-(2-Fluorophenyl)acetyl-amino]-3-methylpentanoylamino}-8-trifluoromethyl-2,3,4,9-tetrahydro-1H-carbazole-3-carboxylic acid ((S)-2-cyclo-propyl-1-thiocarbamoylethyl)amide | 1Aa, 2, 1Ab, d, f, 3A, 4 | 673 | 674.2 |
| 71 | (R)-3-{(S)-2-[2-(2,6-Difluorophenyl)acetyl-amino]-3-methylpentanoylamino}-8-trifluoromethyl-2,3,4,9-tetrahydro-1H-carbazole-3-carboxylic acid ((S)-2-cyclo-propyl-1-thiocarbamoylethyl)amide | 1Aa, 2, 1Ab, d, f, 3A, 4 | 691 | 692.3 |
| 72 | (R)-8-Chloro-6-fluoro-3-{(S)-2-[2-(2-fluoro-phenyl)acetylamino]-3-methylpentanoyl-amino}-2,3,4,9-tetrahydro-1H-carbazole-3-carboxylic acid ((S)-2-cyclopropyl-1-thio carbamoylethyl)amide | 1Aa, 2, 1Ab, d, f, 3A, 4 | 657 | 658.2 |
| 73 | (R)-3-{(S)-2-[2-(2,6-Difluorophenyl)acetyl-amino]-3-methylpentanoylamino}-8-tri-fluoromethyl-2,3,4,9-tetrahydro-1H-carbazole-3-carboxylic acid ((S)-2-methyl-1-thiocarbamoylbutyl)amide | 1Aa, 2, 1Ab, d, f, 3A, 4 | 693 | 694.3 |
| 74 | (R)-3-{(S)-2-[2-(2,6-Difluorophenyl)acetyt-amino]-3-methylpentanoylamino}-8-tri-fluoromethyl-2,3,4,9-tetrahydro-1H-carbazole-3-carboxylic acid ((S)-1-carbamoyl-2-methylbutyl)amide | 1Aa, b, d, f, 3A, 4 | 677 | 678.2 |
| 75 | (R)-3-{(S)-2-[2-(2-Fluorophenyl)acetyl-amino]-3-methylpentanoylamino}-8-tri-fluoromethyl-2,3,4,9-tetrahydro-1H-carbazole-3-carboxylic acid ((S)-1-carbamoyl-2-methylbutyl)amide | 1Aa, b, d, f, 3A, 4 | 659 | 660.4 |
| 76 | (R)-3-{(S)-2-[2-(2-Fluorophenyl)acetyl-amino]-3-methylpentanoylamino}-8-tri-fluoromethyl-2,3,4,9-tetrahydro-1H-carbazole-3-carboxylic acid ((S)-2-methyl-1-thiocarbamoylbutyl)amide | 1Aa, 2, 1Ab, d, f, 3A, 4 | 675 | 676.4 |
| 77 | (R)-8-Chloro-3-{(S)-2-[2-(2,6-difluoro-phenyl)acetylamino]-3-methylpentanoyl-amino}-6-fluoro-2,3,4,9-tetrahydro-1H-carbazole-3-carboxylic acid ((S)-2-cyclo-propyl-1-thiocarbamoylethyl)amide | 1Aa, 2, 1Ab, d, f, 3A, 4 | 675 | 676.3 |

II. Demonstration of the LHRH Antagonistic Effect of Compounds of the Invention II.1A LHRH Receptor-Ligand Binding Assay (Membrane Preparations from Rat Pituitary Cells)

Assay

Heterologous competition experiments were carried out using membrane preparations from rat pituitary cells which naturally strongly express the LHRH receptor. The ligand used in this case was [$^{125}$I][D-Trp$^6$]-LHRH in a concentration of 0.05 nM. Unlabeled [D-Trp$^6$]-LHRH was used in a concentration of 1 µM, or the test substance was used in the desired concentration, for competition. After an incubation time of 90 minutes at 4° C., the bound ligand was measured by scintillation (Halmos et al., *Proc. Natl. Acad. Sci. USA*, 1996, 93, 2398).

Evaluation

The result obtained was the percentage proportion of bound ligand in the presence of the competitor related to the specifically bound proportion of the control (see result for selected compounds in Table 3). EC$_{50}$ values were calculated by nonlinear regression analysis of the competition plots.

TABLE 3

LHRH receptor-ligand binding assay test results, EC$_{50}$ and Ki values for selected substances

| Substance | EC$_{50}$ (M) |
|---|---|
| 7 | $6.9 \times 10^{-9}$ |
| 48 | $8.0 \times 10^{-9}$ |
| 66 | $7.2 \times 10^{-10}$ |
| 67 | $6.9 \times 10^{-9}$ |

TABLE 3-continued

LHRH receptor-ligand binding assay test results, $EC_{50}$ and Ki values for selected substances

| Substance | $EC_{50}$ (M) |
|---|---|
| 68 | $1.0 \times 10^{-9}$ |
| 75 | $5.9 \times 10^{-10}$ |
| 76 | $2.7 \times 10^{-10}$ |

FIGS. 1-7 show the measured competition plots of the LHRH receptor-ligand binding assay with [$^{125}$I][D-Trp6]-LH-RH and the selected substances (7, 48, 66, 67, 68, 75 and 76)

II.1B LHRH Receptor-Ligand Binding Assay (Transfected LTK Cells)

Materials:

$^{125}$I-Triptorelin [$^{125}$I-(D)-Trp6-GnRH] was purchased from Biotrend (Cologne, Germany).

The specific activity was in each case 2.13 Ci/mmol.

All other chemicals are purchased from commercial sources in the highest purity available.

Cell Culture:

LTK cells (mouse fibroblasts: ATCC No. CCL-1.3) which have been transfected with the rat LHRH receptor are cultivated in DMEM medium (Invitrogen Life Technologies, Germany) with penicillin (100 I.U./ml), streptomycin (0.1 mg/ml) and glutamine (0.01 mol/l) and 10% fetal calf serum (FCS; Invitrogen Life Technologies, Germany) on plastic tissue culture plates (Nunc, Germany, 245×245-20 mm).

Testing:

80% confluent cell culture plates are washed twice with 50 ml of phosphate-buffered saline (PBS) and then detached with 0.01 M EDTA solution. The cells are pelleted by centrifugation at 200·g for 5 min in a laboratory centrifuge (Kendro, Germany). The cell pellet is resuspended in 3 ml of binding medium (DMEM; 10 mM Hepes; 0.5% BSA; 0.1% $NaN_1$; 1 g/l bacitracin (add fresh, stock 100×); 0.1 g/l SBTI (add fresh, stock 1000×) and the cell count is determined by Trypan blue staining in a Neubauer counting chamber. The cell suspension is adjusted with binding medium to a concentration of $5 \times 10^5$ cells/0.05 ml.

Binding studies for competition plots are carried out as duplicates. The test substances are employed as 10 mM DMSO solutions. They are diluted to 4 times the final concentration employed with binding medium. 25 µl of the substance dilution are mixed with 25 µl of tracer solution ($^{125}$I-triptorelin or $^{125}$I-cetrorelix). The tracer concentration is adjusted to approx. 50 000 cpm (measured in a Cobra II, γ counter. PE Liefe Science, Germany) in the final reaction volume of 100 µl.

200 µl of silicone/liquid paraffin mixture (84%:16%) are introduced into 650 µl conical tubes (Roth. Germany). 50 µl of the cell suspension are pipetted thereon, followed by 50 µl of the test substance/tracer mixture. The tubes are capped and incubated with vertical rotation in an incubator at 37° C. for 60 min. After incubation, the samples are centrifuged in a centrifuge (Kendro, Germany) at 900 rpm and subsequently shock-frozen in liquid $N_2$. The tip with the cell pellet is cut off and transferred into prepared counting vials (Roth, Germany). The remainder of the conical tube with the remaining supernatant is likewise transferred into a counting vial. The measurement takes place in a γ counter for 1 min/sample.

Evaluation of the samples takes place after calculation of the specific binding compared with untreated cells, after subtraction of the nonspecific binding (excess of unlabeled ligand, 1 µM) by means of GraphPad Prism or alternatively by means of OMMM software.

TABLE 4

LHRH receptor-ligand binding assay test results, $EC_{50}$ values for a number of selected exemplary substances

| Example No. | Binding to r-LHRHR $EC_{50}$ [µM] | Autonom name |
|---|---|---|
| 1 | 0.2609 | 4-Chlorobenzyl {1-[3-(carbamoyl-2-methylpropylcarbamoyl)-6,8-dichloro-2,3,4,9-tetrahydro-1H-carbazol-3-ylcarbamoyl]-2-methyl-propyl}carbamate |
| 2 | 0.2051 | 4-Chlorobenzyl {1-[3-(carbamoyl-2-methylpropylcarbamoyl)-6,8-dichloro-2,3,4,9-tetrahydro-1H-carbazol-3-ylcarbamoyl]-2-methyl-butyl}carbamate |
| 3 | 0.0472 | 4-Chlorobenzyl {1-[3-(carbamoyl-2-methylbutylcarbamoyl)-6,8-dichloro-2,3,4,9-tetrahydro-1H-carbazol-3-ylcarbamoyl]-2-methyl-butyl}carbamate |
| 4 | 0.0048 | 6,8-Dichloro-3-{2-[2-(2-fluorophenyl)acetylamino]-3-methyl-pentanoylamino}-2,3,4,9-tetrahydro-1H-carbazole-3-carboxylic acid (1-carbamoyl-2-methylbutyl)amide |
| 5 | 0.09835 | 6,8-Dichloro-3-{2-[2-(3-fluorophenyl)acetylamino]-3-methyl-pentanoylamino}-2,3,4,9-tetrahydro-1H-carbazole-3-carboxylic acid (1-carbamoyl-2-methylbutyl)amide |
| 6 | 0.1037 | 2-Chlorobenzyl {1-[3-(1-carbamoyl-2-methylbutylcarbamoyl)-6,8-dichloro-2,3,4,9-tetrahydro-1H-carbazol-3-ylcarbamoyl]-2-methyl-butyl}carbamate |
| 7 | 0.0079 | Benzyl {1-{6,8-dichloro-3-[2-methyl-1-thiocarbamoylbutylcarbamoyl)-2,3,4,9-tetrahydro-1H-carbazol-3-ylcarbamoyl]-2-methylbutyl}carbamate |
| 8 | 0.0453 | Benzyl 4-{3-benzyloxycarbonylamino-3-[3-(1-carbamoyl-2-methyl-butylcarbamoyl)-6,8-dichloro-2,3,4,9-tetrahydro-1H-carbazol-3-ylcarbamoyl]propyl}phenyl carbonate |
| 10 | 0.0075 | Benzyl [1-[6,8-dichloro-3-(2-methyl-1-thiocarbamoylbutylcarbamoyl)-2,3,4,9-tetrahydro-1H-carbazol-3-ylcarbamoyl]-3-(4-hydroxyphenyl)propyl]carbamate |
| 11 | 0.01725 | Benzyl [1-[3-(1-carbamoyl-2-methylbutylcarbamoyl)-6,8-dichloro-2,3,4,9-tetrahydro-1H-carbazol-3-ylcarbamoyl]-3-(4-phosphono-oxyphenyl)propyl]carbamate |
| 12 | 0.0392 | Benzyl [1-[6,8-dichloro-3-(2-methyl-1-thiocarbamoyl-butylcarbamoyl)-2,3,4,9-tetrahydro-1H-carbazol-3-ylcarbamoyl]-3-(4-phosphonooxyphenyl)propyl]carbamate |

TABLE 4-continued

LHRH receptor-ligand binding assay test results, $EC_{50}$ values for a number of selected exemplary substances

| Example No. | Binding to r-LHRHR $EC_{50}$ [μM] | Autonom name |
|---|---|---|
| 13 | 0.0024 | 6,8-Dichloro-3-{2-[2-(2-fluorophenyl)acetylamino]-3-methyl-pentanoylamino}-2,3,4,9-tetrahydro-1H-carbazole-3-carboxylic acid (2-methyl-1-thiocarbamoylbutyl)amide |
| 14 | 0.00205 | 6,8-Dichloro-3-[2-[2-(2-fluorophenyl)acetylamino]-4-(4-hydroxyphenyl)butyrylamino]-2,3,4,9-tetrahydro-1H-carbazole-3-carboxylic acid (2-methyl-1-thiocarbamoylbutyl)amide |
| 16 | 0.62805 | 6,8-Dichloro-3-{2-[3-(4-fluorophenyl)propionylamino]-3-methyl-pentanoylamino}-2,3,4,9-tetrahydro-1H-carbazole-3-carboxylic acid (1-carbamoyl-2-methylpropyl)amide |
| 17 | 0.5252 | 5-[3-(1-Carbamoyl-2-methylpropylcarbamoyl)-6,8-dichloro-2,3,4,9-tetrahydro-1H-carbazol-3-ylcarbamoyl]-5-[3-(4-fluorophenyl)propionylamino]pentylammonium trifluoroacetate |
| 22 | 0.02465 | 6,8-Dichloro-3-[2-[3-(2-fluorophenyl)propionylamino]-4-(4-hydroxyphenyl)butyrylamino]-2,3,4,9-tetrahydro-1H-carbazole-3-carboxylic acid (1-carbamoyl-2-methylbutyl)amide |
| 23 | 0.0729 | 6,8-Dichloro-3-{2-[3-(2-fluorophenyl)propionylamino]-3-methyl-pentanoylamino}-2,3,4,9-tetrahydro-1H-carbazole-3-carboxylic acid (1-carbamoyl-2-methylbutyl)amide |
| 24 | 0.0135 | Benzyl {1-[6,8-dichloro-3-(2-methyl-1-thiocarbamoyl-butylcarbamoyl)-2,3,4,9-tetrahydro-1H-carbazol-3-ylcarbamoyl]-3-[4-(2-{2-[2-(2-methoxyethoxy)ethoxy]ethoxy}-ethoxy)phenyl]propyl}carbamate |
| 25 | 0.0042 | Benzyl {1-[8-chloro-6-fluoro-3-(2-methyl-1-thiocarbamoyl-butylcarbamoyl)-2,3,4,9-tetrahydro-1H-carbazol-3-ylcarbamoyl]-2-methylbutyl}carbamate |

II.2 Inhibition of LHRH-Induced LH Secretion from Rat Pituitary Cells in Vitro

Materials

The LH concentration in cell culture supernatants was measured using the rat luteinizing hormone (rLH) enzyme immunoassay (EIA) system ELISA (RPN 2562) from Amersham Pharmacia Biotech. All other chemicals used were from commercial sources in the highest purity available.

Cell Culture

Juvenile male Wistar rats (Harlan Winkelmann, Germany) were sacrificed by decapitation, and the pituitaries were removed and taken up in Hanks' buffer (HBSS) with 0.3% BSA and 10 mM HEPES (pH 7.4). Pituitaries from 20 rats were required to carry out one experiment. The cells of the anterior lobe of the pituitary were separated from the remaining tissue by incubation in Hanks' buffer with 10 mM HEPES (pH 7.4), 0.3% BSA, 1 mg/ml hyaluronidase (type VIII), 1 mg/ml soybean trypsin inhibitor, 10 μg/ml DNAsel and 1 mg/ml papain at 37° C. for 30 minutes A sterile Pasteur pipette was used to disperse the cells, and they were subsequently pelleted by centrifugation. The cells were seeded in a density of $2.5 \times 10^5$ cells/well of a collagen-coated 48-well plate (Becton Dickinson) in DMEM medium (Invitrogen Life Technologies, Germany) with 10% fetal calf serum (FCS; Invitrogen Life Technologies, Germany), 10 mill nonessential amino acids and 10 mill Pen/Strep (penicillin/streptomycin).

Assay

The medium was changed after incubation at 37° C., 5% $CO_2$ and 95% humidity for 48 h. The medium was replaced by LHRH-containing (10 nM) medium or medium with LHRH (10 nM) and test substance in the concentration indicated (table). After a further incubation for 3 hours, the cell supernatant was harvested and frozen at −20° C. The LH content was determined by means of ELISA in triplicate determination in accordance with the manufacturer's (Amersham Pharmacia Biotech) instructions.

In the following table, "% Inhibition" describes the quotient of LHRH-stimulated LH secretion with ("LH (ng/ml)" and without the addition of the test substance. The values originate from different, independent experiments.

TABLE 5

Inhibition of LHRH-stimulated LH secretion from rat pituitary cells by selected substances

| Substance | Concentration | LH (ng/ml) ± SD | % Inhibition |
|---|---|---|---|
| 4 | $3.3 \times 10^{-8}$ M | 79.3 ± 5.7 | 67% |
| 4 | $3.3 \times 10^{-9}$ M | — | — |
| 7 | $3.3 \times 10^{-8}$ M | 79.9 ± 15.0 | 83% |
| 7 | $3.3 \times 10^{-9}$ M | 194.0 ± 13.2 | 43% |
| 10 | $3.3 \times 10^{-8}$ M | 118.7 ± 11.6 | 39% |
| 10 | $3.3 \times 10^{-9}$ M | 198.8 ± 4.2 | 0% |

II.3 LH Concentration Suppression in the Plasma of Castrated Rats

Materials

The LH concentration in the plasma of castrated rats was measured using the rat luteinizing hormone (rLH) enzyme immunoassay (EIA) system ELISA (RPN 2562) from Amersham Pharmacia Biotech or of LH RIA-AH R002 rats; from Biocode-Hycel, Liege, Belgium. All other chemicals used were from commercial sources in the highest purity available.

Animals 10 days before the start of the test, male Sprague Dawley rats (Harlan Winkelmann, Germany) weighing 190-220 g were anesthetized with ether and castrated and provided with a silicone catheter for permanent blood sampling.

Assay

At the start of the test, before administration of the substance, blood samples were taken and the LH level determined. The substance was then administered orally in the desired concentration. The number of animals used in each group was 8. At the stated times, further blood samples were taken. The blood was collected in heparinized sample tubes on ice, and the plasma was obtained by centrifugation at 3000 g for 10 minutes. The plasma samples were stored at −20° C. until the LH concentration was measured by ELISA or RIA. The LH concentration was determined by an ELISA or RIA in duplicate determination in accordance with the manufacturer's (Amersham Pharmacia Biotech; Biocode-Hycel) instructions.

Evaluation and Statistics

Since the rats showed large differences in the individual LH concentrations, owing to the physiological pulsatile secretion of LH, the values before treatment with the substance have been indicated as averages of the individual LH concentrations and correspond to the 100% value. All the other data points for each individual animal were calculated as relative concentration compared with the LH concentration before treatment.

TABLE 6

Relative LH concentration in rat plasma after treatment with substance 7 in a dosage of 100 mg/kg in Solutol HS15/1,2-propane-diol (3:1)

| Time (h) | Relative LH concentration (%) (averages ± SEM compared with the concentration before treatment) |
|---|---|
| −4 | 97.4 ± 15.3 |
| −2 | 110.8 ± 12.2 |
| 0 | 91.8 ± 19.1 |
| +4 | 19.6 ± 8.9 |
| +6 | 10.1 ± 3.2 |
| +24 | 65.1 ± 13.9 |
| +48 | 110.6 ± 33.0 |
| +72 | 268.4 ± 93.0 |

TABLE 7

Relative LH concentration in rat plasma after treatment with substance 68 in a dosage of 19 mg/kg in Solutol HS15/1,2-propane-diol (3:1)

| Time (h) | Relative LH concentration (%) (averages ± SEM compared with the concentration before treatment) |
|---|---|
| −24 | 105.4 ± 12.7 |
| 0 | 95.0 ± 9.3 |
| +4 | 17.4 ± 3.3 |
| +6 | 16.0 ± 1.5 |
| +8 | 12.9 ± 1.0 |
| +12 | 16.0 ± 2.6 |
| +24 | 65.7 ± 10.8 |
| +30 | 78.1 ± 7.7 |

III. Demonstration of the Antagonistic Effect of the Compounds of the Invention of the General Formulae (I, Ia and Ib) on Receptors of the Neurokinin Family ($NK_1$ and $NK_2$)

Receptor affinities ($IC_{50}$ values) of the compounds of the invention of the general formulae (I, Ia and Ib) were measured as described by E. Heuillet et al., *J. Neurochem.*, 60: 868-876 (1993) and D. Aharony et al. *Mol. Pharmacol*, 44: 356-363 (1993) commercially by Cerep (Assay 826-1h on page 67 and Assay 826-2h on page 68 of the 2005 catalogue).

| Assay | Substance | IC50 (M) | Ki (M) | nH |
|---|---|---|---|---|
| NK1 (h) | 68 | 1.4E−06 | 6.4E−07 | 2.0 |
| NK2 (h) | 68 | 1.6E−06 | 8.5E−07 | 3.8 |
| NK1 (h) | 76 | 1.9E−06 | 8.4E−07 | 2.3 |
| NK2 (h) | 76 | 1.5E−06 | 8.1E−07 | 2.3 |

FIGS. 8-11 show competition plots measured in the NK1 and NK2 receptor-ligand binding assays with [$Sar^9$, $Met(O_2)^{11}$]-SP for NK1 and [$Nle^{10}$]-NKA(4-10) for NK2, and the selected substances (68 and 76).

IV. Demonstration of the Saturation Solubility in Water for the Compounds of the Invention of the General Formulae (I, Ia and Ib)

The saturation solubility in water was determined in accordance with the following description: to initiate dissolving of the substances and to improve the wetting of the samples, a maximum of 1% DMSO was added. The content was checked by using an HPLC UV method. The results are summarized in Table 8 below.

TABLE 8

Water solubilities of selected compounds

| Compound name | Compound number | Saturation solubility in water [μg/ml] |
|---|---|---|
| Benzyl [1-[3-(1-carbamoyl-2-methyl-butylcarbamoyl)-6,8-dichloro-2,3,4,9-tetrahydro-1H-carbazol-3-ylcarbamoyl]-3-(4-phosphonooxyphenyl)propyl]-carbamate | 11 | 39.9 |
| Benzyl {1-{6,8-dichloro-3-[2-methyl-1-thiocarbamoylbutylcarbamoyl)-2,3,4,9-tetrahydro-1H-carbazol-3-ylcarbamoyl]-2-methylbutyl}carbamate | 7 | 54.6 |
| Benzyl [1-[3-(1-carbamoyl-2-methyl-butylcarbamoyl)-6,8-dichloro-2,3,4,9-tetrahydro-1H-carbazol-3-ylcarbamoyl]-2-(4-phosphonooxyphenyl)ethyl]-carbamate | 9 | 150.6 |
| Benzyl [1-[3-(1-carbamoyl-2-methyl-butylcarbamoyl)-6,8-dichloro-2,3,4,9-tetrahydro-1H-carbazol-3-ylcarbamoyl]-2-methylbutyl]carbamate | Example 295 from WO 03/051837 A2 | <0.05 |
| Benzyl (1-{3-[carbamoylcyclohexyl-methyl)carbamoyl]-6,8-dichloro-2,3,4,9-tetrahydro-1H-carbazol-3-ylcarbamoyl}-2-methylbutyl)carbamate | Example 300 from WO 03/051837 A2 | 0.38 |
| Benzyl [1-[3-(1-carbamoyl-2-methyl-butylcarbamoyl)-6,8-dichloro-2,3,4,9-tetrahydro-1H-carbazol-3-ylcarbamoyl]-3-(4-hydroxyphenyl)propyl]carbamate | Example 303 from WO 03/051837 A2 | 0.35 |

V. Demonstration of the Metabolic Stability of the Compounds of the General Formulae (I, Ia and Ib)

The metabolic stability in relation to liver microsomes (species human, rat) was determined in accordance with the following description: the substances were incubated at a test concentration of 1 or 10 μM with rat liver microsomes or human liver microsomes at 37° C. for 45 minutes with addition of NADPH. An HPLC MS/MS method was subsequently used to quantify the unmetabolized amount of starting compound relative to 100%. The results are summarized in Table 9 below.

TABLE 9

Metabolic stability of selected compounds in relation to liver microsomes of various species

| Compound name | Compound number | Metabolic stability (rat) [1 h, % recovery] | Metabolic stability (human) [1 h, % recovery] |
|---|---|---|---|
| Benzyl {(S)-1-[(R)-6,8-dichloro-3-((S)-2-methyl-1-thiocarbamoylbutyl-carbamoyl)-2,3,4,9-tetrahydro-1H-carbazol-3-ylcarbamoyl]-2-methyl-butyl}carbamate (1 μM) | 7 | 78% | 65% |
| Benzyl [(S)-1-[(R)-3-((S)-carbamoyl-2-methylbutylcarbamoyl)-6,8-dichloro-2,3,4,9-tetrahydro-1H-carbazol-3-ylcarbamoyl]-3-(4-phosphonooxyphenyl)-propyl]carbamate (1 μM) | 11 | n.d. | 77% |
| (R)-8-Chloro-6-fluoro-3-{(S)-2-[2-(2-fluorophenyl)acetylamino]-3-methyl-pentanoylamino}-2,3,4,9-tetrahydro-1H-carbazole-3-carboxylic acid ((S)-2-methyl-1-thiocarbamoylbutyl)amide (10 μM) | 68 | 80% | 75% |
| (R)-3-{(S)-2-[2-(2-Fluorophenyl)-acetylamino]-3-methylpentanoyl-amino}-8-trifluoromethyl-2,3,4,9-tetrahydro-1H-carbazole-3-carboxylic acid ((S)-2-methyl-1-thiocarbamoyl-butyl)amide (10 μM) | 76 | 69% | 84% |
| Benzyl {(S)-1-[(R)-3-((S)-1-carbamoyl-2-methylbutylcarbamoyl)-6,8-dichloro-2,3,4,9-tetrahydro-1H-carbazol-3-ylcarbamoyl]-2-methyl-butyl]carbamate (1 μM) | Example 295 from WO 03/051837 A2 | 0% | 0% |
| Benzyl {(S)-1-[(R)-3-((S)-1-carbamoyl-2-methylbutylcarbamoyl)-8-methoxy-2,3,4,9-tetrahydro-1H-carbazol-3-ylcarbamoyl]-2-methyl-butyl]carbamate (1 μM) | Example 294 from WO 03/051837 A2 | 5% | 0% |

The invention claimed is:

1. A method for the treatment of a pathological condition mediated by a G-protein coupled receptor or of a pathological condition which can be treated by modulation of a G-protein coupled receptor, comprising administering an effective amount of a compound of the formula (I)

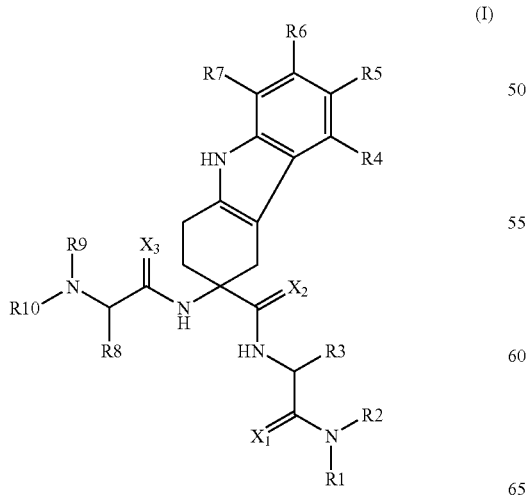

in which:

$X_1$ is S, $X_2$ and $X_3$ are independently of one another O or geminally linked $H_2$, R1 and R2 are independently of one another selected from the group consisting of —H, aryl, alkyl and arylalkyl radicals which are optionally substituted in the alkyl and/or aryl group by up to 3 substituents independently selected from the group consisting of —Hal, —CN and —O-alkyl, where R1 and R2 are in particular hydrogen, R3 is an alkyl, arylalkyl or heteroarylalkyl radical, which are optionally substituted by up to 3 substituents independently selected from the group consisting of
—Hal, —CN, —CO—O—R12, —CO—NR12R12', —OH, —O—R13, —O—CO—R13, —O—SO₂—OR12, —O—SO₂—R12, —SO₂—SO—R12, —SO—R12, —O—PO(OR12)(OR12'), —O—PO(NR12R12')₂, —O—CO—O—R13, —O—CO—NR12R12', —O—CS—NR12R12', —S—R12, —NR12R12', —NH—CO—R13, —NH—SO₂—R12, —NH—CO—O—R13, —NH—CO—NHR12, —NH—C(NH)—NH₂, R4, R5, R6 and R7 are selected independently of one another from the group consisting of H, —Hal, —CN, —CONH₂, —COOH, —CF₃, —O-alkyl, —OCF₃, —NO₂, and alkyl, arylalkyl and heteroarylalkyl radicals;

R9 is a hydrogen atom, an alkyl, an aryl, a heteroaryl, an arylalkyl or a heteroarylalkyl radical;

R10 is a hydrogen atom, or the radical —R11, —CO—R11, —CO—OR11, —CO—NHR11, —C(NH)—NHR11, —SO$_2$—R11, or —SO$_2$—NHR11;

R11 is an alkyl, an aryl, a heteroaryl, an arylalkyl or a heteroarylalkyl radical, which are optionally substituted by one or more substituents independently selected from the group consisting of —Hal, —CN, -alkyl, —CF$_3$, —OCF$_3$, —OH, —O-alkyl, and —O—(CH$_2$CH$_2$—O)$_n$—CH$_3$;

R8 is —C$_1$-C$_6$-alkyl-aryl or —C$_1$-C$_6$-alkyl-heteroaryl, where the aryl or heteroaryl group is substituted by one to three substituents independently selected from the group consisting of —O—(CH$_2$CH$_2$O)$_n$—CH$_3$, —O—CO—R12, —O—CO—(CH$_2$CH$_2$—O)$_n$—CH$_3$, —O—SO$_2$—OR12, —O—SO$_2$—R12, —O—PO(OR12)(OR12'), —O—PO(NR12R12')$_2$, —O—CO—OR13, —O—CO—NR12R12', and —O—CS—NR12R12', or, where, however, at least (i) X$_1$ is S, or (ii) R10 is not H, and R11 is an arylalkyl or heteroarylalkyl radical, which are substituted in the aryl or heteroaryl group by one or more substituents independently selected from the group consisting of Hal, —CN, -alkyl, —CF$_3$, —OCF$_3$, —OH, —O-alkyl, and —O—(CH$_2$CH$_2$—O)$_n$—CH$_3$, R8 also assumes the meanings indicated for R3;

R12 and R12' are independently of one another H, or an alkyl, arylalkyl, aryl, heteroarylalkyl, or heteroaryl radical;

R13 is selected from an alkyl, arylalkyl, aryl, heteroarylalkyl, and heteroaryl radical, or is the group —(CH$_2$CH$_2$—O)$_n$—CH$_3$, and n is an integer from 1 to 10;

or a physiologically tolerated salt of the compound of the formula (I), where the salts are obtainable by neutralizing the bases with inorganic or organic acids or by neutralizing the acids with inorganic or organic bases, where the compound of the formula (I) and its salts may be in the form of their racemates, in the form of the pure enantiomers and/or diastereomers or in the form of mixtures of these enantiomers and/or diastereomers, and/or in the form of the tautomers thereof, to an individual in need thereof, wherein the condition is selected from the group consisting of female sub- or infertility, benign prostate hyperplasia (BPH), endometriosis, uterine fibroids, uterine myomas, endometrium hyperplasia, dysmenorrhea, dysfunctional uterine bleeding, pubertas praecox, hirsutism, polycystic ovary syndrome and prostate cancer.

2. The method as claimed in claim 1, where the G-protein coupled receptor is an LHRH receptor.

3. The method as claimed in claim 1, where the G-protein coupled receptor is a receptor of the neurokinin family.

4. The method as claimed in claim 2, where the compound of the formula (I) and its salts act as an LHRH receptor antagonist.

5. The method as claimed in claim 3, where the compound of the formula (I) and its salts act as an antagonist of the NK$_1$ and/or of the NK$_2$ receptor.

6. The method as claimed in claim 2 for the treatment of female sub- or infertility.

7. The method as claimed in claim 2, where the pathological condition mediated by the LHRH receptor or the pathological condition which can be treated by modulation of the LHRH receptor is selected from the group comprising: benign prostate hyperplasia (BPH), endometriosis, uterine fibroids, uterine myomas, endometrium hyperplasia, dysmenorrhoea, dysfunctional uterine bleeding (menorrhagia, metrorrhagia), pubertas praecox, hirsutism, polycystic ovary syndrome and prostate cancer.

8. The method as claimed in claim 7, where the pathological condition mediated by the LHRH receptor or the pathological condition which can be treated by modulation of the LHRH receptor is prostate cancer.

9. The method as claimed in claim 3, where the G-protein coupled receptor is an NK$_1$ and/or NK$_2$ receptor.

* * * * *

UNITED STATES PATENT AND TRADEMARK OFFICE
CERTIFICATE OF CORRECTION

PATENT NO. : 8,067,456 B2  
APPLICATION NO. : 12/070214  
DATED : November 29, 2011  
INVENTOR(S) : Klaus Paulini et al.

Page 1 of 1

It is certified that error appears in the above-identified patent and that said Letters Patent is hereby corrected as shown below:

On the title page, Item (54) delete "(GPCPS)" and insert --(GPCRS)--.

On the title page, for Item (75), "Inventors," for the last name of the third inventor, please replace "Gunther" with "Günther".

Signed and Sealed this
Third Day of January, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,067,456 B2 | Page 1 of 1 |
| APPLICATION NO. | : 12/070214 | |
| DATED | : November 29, 2011 | |
| INVENTOR(S) | : Klaus Paulini et al. | |

It is certified that error appears in the above-identified patent and that said Letters Patent is hereby corrected as shown below:

On the title page, Item (54) and at Column 1, line 5, in the title, delete "(GPCPS)" and insert --(GPCRS)--.

On the title page, for Item (75), "Inventors," for the last name of the third inventor, please replace "Gunther" with "Günther".

This certificate supersedes the Certificate of Correction issued January 3, 2012.

Signed and Sealed this

Thirty-first Day of January, 2012

David J. Kappos
*Director of the United States Patent and Trademark Office*